United States Patent
Zhen et al.

(10) Patent No.: US 11,923,419 B2
(45) Date of Patent: Mar. 5, 2024

(54) NON-COVALENT MODIFICATION OF GRAPHENE-BASED CHEMICAL SENSORS

(71) Applicant: REGENTS OF THE UNIVERSITY OF MINNESOTA, Minneapolis, MN (US)

(72) Inventors: Xue Zhen, Plymouth Meeting, PA (US); Philippe Pierre Joseph Buhlmann, Minneapolis, MN (US); Steven J. Koester, Edina, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 774 days.

(21) Appl. No.: 16/996,537

(22) Filed: Aug. 18, 2020

(65) Prior Publication Data

US 2021/0057526 A1    Feb. 25, 2021

Related U.S. Application Data

(60) Provisional application No. 62/889,387, filed on Aug. 20, 2019.

(51) Int. Cl.
*H01L 29/16* (2006.01)
*A61B 5/08* (2006.01)
(Continued)

(52) U.S. Cl.
CPC .......... *H01L 29/1606* (2013.01); *A61B 5/082* (2013.01); *A61L 31/024* (2013.01);
(Continued)

(58) Field of Classification Search
CPC .. G01N 27/045; G01N 27/228; G01N 33/497; G01N 2027/222; H01L 29/1606;
(Continued)

(56) References Cited

U.S. PATENT DOCUMENTS

| 8,294,135 B2 | 10/2012 | Lebedev et al. |
| 8,581,262 B2 | 11/2013 | Pan et al. |

(Continued)

FOREIGN PATENT DOCUMENTS

| CA | 2673142 | 4/2008 |
| CA | 2800887 | 12/2011 |

(Continued)

OTHER PUBLICATIONS

"International Search Report and Written Opinion," for PCT Application No. PCT/US2022/019728 dated Jun. 9, 2022 (11 pages).

(Continued)

*Primary Examiner* — Benjamin R Schmitt
(74) *Attorney, Agent, or Firm* — Pauly, DeVries Smith & Deffner LLC

(57) ABSTRACT

Chemical sensors, devices and systems including the same, and related methods are disclosed. In an embodiment, a medical device is included having a graphene varactor including a graphene layer and a self-assembled monolayer disposed on an outer surface of the graphene layer through non-covalent interactions between the self-assembled monolayer and a π-electron system of graphene. The self-assembled monolayer includes one or more pillarenes, substituted pillarenes, calixarenes, substituted calixarenes, peralkylated cyclodextrins, substituted peralkylated cyclodextrins, pyrenes, or substituted pyrenes, or derivatives of each. Other embodiments are also included.

20 Claims, 6 Drawing Sheets

(51) Int. Cl.
  *A61L 31/02* (2006.01)
  *C01B 32/194* (2017.01)
  *G01N 27/04* (2006.01)
  *G01N 27/22* (2006.01)
  *G01N 33/497* (2006.01)
  *H01L 29/93* (2006.01)
  *H01L 21/02* (2006.01)

(52) U.S. Cl.
  CPC ......... *C01B 32/194* (2017.08); *G01N 27/045* (2013.01); *G01N 27/228* (2013.01); *G01N 33/497* (2013.01); *H01L 29/93* (2013.01); *C01B 2204/22* (2013.01); *G01N 2027/222* (2013.01); *H01L 21/02499* (2013.01); *H01L 2229/00* (2013.01)

(58) Field of Classification Search
  CPC .............. H01L 29/93; H01L 21/02499; H01L 2229/00; A61B 5/082; A61L 31/024
  See application file for complete search history.

(56) References Cited

U.S. PATENT DOCUMENTS

| | | |
|---|---|---|
| 8,951,473 B2 | 2/2015 | Wang et al. |
| 8,961,830 B2 | 2/2015 | Reynolds et al. |
| 9,011,779 B1 | 4/2015 | Anglin, Jr. et al. |
| 9,085,715 B2 | 7/2015 | Berthelot et al. |
| 9,267,908 B2 | 2/2016 | Wang et al. |
| 9,366,664 B2 | 6/2016 | Anglin, Jr. et al. |
| 9,410,040 B2 | 8/2016 | Li et al. |
| 9,513,244 B2 | 12/2016 | Koester |
| 9,620,727 B2 | 4/2017 | Laaksonen et al. |
| 9,671,392 B2 | 6/2017 | Jeppsen et al. |
| 9,689,836 B2 | 6/2017 | Makaram et al. |
| 9,775,241 B2 | 9/2017 | Walczak et al. |
| 9,859,034 B2 | 1/2018 | Sjong |
| 11,079,371 B2 | 8/2021 | Zhen et al. |
| 11,156,576 B2 | 10/2021 | Harada et al. |
| 11,293,914 B2 | 4/2022 | Zhen et al. |
| 2009/0104435 A1 | 4/2009 | Hutchison et al. |
| 2012/0058350 A1 | 3/2012 | Long et al. |
| 2012/0184041 A1 | 7/2012 | Carella et al. |
| 2012/0214172 A1 | 8/2012 | Chen et al. |
| 2014/0145735 A1 | 5/2014 | Koester et al. |
| 2015/0298115 A1 | 10/2015 | Campidelli et al. |
| 2015/0338390 A1 | 11/2015 | Anglin et al. |
| 2016/0093806 A1 | 3/2016 | Turchanin |
| 2016/0289769 A1 | 10/2016 | Schwartz et al. |
| 2016/0334386 A1 | 11/2016 | Anglin et al. |
| 2016/0356741 A1 | 12/2016 | Makaram et al. |
| 2017/0212116 A1 | 7/2017 | Braga et al. |
| 2017/0307576 A1 | 10/2017 | Anglin, Jr. et al. |
| 2019/0025237 A1 | 1/2019 | Kelly et al. |
| 2019/0257825 A1 | 8/2019 | Zhen et al. |
| 2019/0331661 A1 | 10/2019 | Zhen et al. |
| 2020/0166435 A1 | 5/2020 | Sherwood et al. |
| 2020/0191737 A1 | 6/2020 | Sherwood et al. |
| 2021/0072208 A1 | 3/2021 | Sherwood et al. |
| 2021/0242685 A1 | 8/2021 | Godridge et al. |
| 2021/0356457 A1 | 11/2021 | Zhen et al. |
| 2021/0369250 A1 | 12/2021 | Buhlmann et al. |
| 2022/0291198 A1 | 9/2022 | Zhen et al. |
| 2022/0304589 A1 | 9/2022 | Troudt et al. |

FOREIGN PATENT DOCUMENTS

| | | | |
|---|---|---|---|
| CN | 102183557 | 9/2011 | |
| CN | 103341350 | 10/2013 | |
| CN | 103926278 | 7/2014 | |
| CN | 103950920 | 7/2014 | |
| CN | 104730121 | 6/2015 | |
| CN | 103852505 | 11/2015 | |
| CN | 105021680 | 11/2015 | |
| CN | 103877574 | 1/2016 | |
| CN | 105688995 | 6/2016 | |
| CN | 107180706 | 9/2017 | |
| CN | 109206628 | 1/2019 | |
| CN | 109422835 | 3/2019 | |
| CN | 111788477 | 10/2020 | |
| CN | 112041672 | 12/2020 | |
| CN | 117083519 | 11/2023 | |
| EP | 3431977 | 1/2019 | |
| EP | 3755995 | 12/2020 | |
| IN | 201627028955 | 10/2016 | |
| JP | H0682455 | 3/1994 | |
| JP | 2012122814 | 6/2012 | |
| JP | 5837058 | 11/2015 | |
| JP | 2020041981 | 3/2020 | |
| KR | 20130133373 | 12/2013 | |
| KR | 20170057001 | 5/2017 | |
| KR | 101797737 | 11/2017 | |
| WO | WO-2010097518 A1 * | 9/2010 | ............. B82Y 10/00 |
| WO | 2011158068 | 12/2011 | |
| WO | 2012135565 | 10/2012 | |
| WO | 2012138632 | 10/2012 | |
| WO | 2015179623 | 11/2015 | |
| WO | 2016145300 | 9/2016 | |
| WO | 2017066583 | 4/2017 | |
| WO | 2017095922 | 6/2017 | |
| WO | 2019164922 | 8/2019 | |
| WO | 2019209918 | 10/2019 | |

OTHER PUBLICATIONS

"First Office Action," for Chinese Patent Application No. 201980014236.1 dated Jan. 20, 2023 (13 pages) with English summary.

"First Office Action," for Chinese Patent Application No. 201980027577.2 dated Feb. 10, 2023 (12 pages) with English summary.

"Non-Final Office Action," for U.S. Appl. No. 17/707,214 dated Mar. 17, 2023 (42 pages).

"Response to Communication Purusant to Article 94(3) EPC," for European Patent Application No. 19709268.7 filed Mar. 22, 2023 (12 pages).

"Second Office Action," for Chinese Patent Application No. 201980014236.1 dated Mar. 29, 2023 (6 pages) with English summary.

Li, C., et al. "The Electrochemical Sensor Based on Electrochemical Oxidation of Nitrite on Metalloporphyrin-Graphene Modified Glassy Carbon Electrode," Royal Society of Chemistry, 2016, 6, 90480 (9 pages).

Wang, Aijian, et al. "Graphene and Carbon-Nanotube Nanohybrids Covalently Functionalized by Porphyrins and Phthalocyanines for Optoelectronic Properties," Advanced Materials, 2018, 30, 1705704 (9 pages).

"Response to Communication Pursuant to Rules 161(1) and 162 EPC," for European Patent Application No. 19733177.0 filed Jun. 4, 2021 (20 pages).

"Response to Examination Report," for Australian Patent Application No. 2019224011 filed Jul. 23, 2021 (22 pages).

"First Examination Report," for Australian Patent Application No. 2019224011 dated Apr. 9, 2021 (4 pages).

Giancane, Gabriele et al., "State of Art in Porphyrin Langmuir-Blodgett Films as Chemical Sensors," Advances in Colloid and Interface Science, 2012, vol. 171-172, pp. 17-35 (Year: 2012), 19 pages.

Hasobe, Taku "Photo—and Electro-Functional Self-Assembled Architectures of Porphyrins," Physics Chemistry Chemical Physics, 2012, 14, pp. 15975-15987 (Year: 2012), 13 pages.

"Non-Final Office Action," for U.S. Appl. No. 16/393,177 dated May 25, 2021 (37 pages).

"Non-Final Office Action," for U.S. Appl. No. 16/280,635 dated Feb. 10, 2021 (40 pages).

"Notice of Allowance," for U.S. Appl. No. 16/280,635 dated Mar. 31, 2021 (14 pages).

(56) References Cited

OTHER PUBLICATIONS

"Response to Communication Pursuant to Rules 161(1) and 162 EPC," for European Patent Application No. 19709268.7 filed Apr. 1, 2021 (12 pages).
"Response to Non-Final Rejection," dated Feb. 10, 2021 for U.S. Appl. No. 16/280,635, submitted via EFS-Web on Mar. 17, 2021, 16 pages.
"Determination of Carbonyl Compounds By High performance Liquid Chromatography (HPLC)," EPA Method 8315A 1996 (34 pages).
"International Preliminary Report on Patentability," for PCT Application No. PCT/US2020/046829 dated Mar. 3, 2022 (9 pages).
Cancilla, Devon A., et al."O-(2,3,4,5,6-Pentafluorophenyl)methylhydroxylamine hydrochloride: a versatile reagent for the determination of carbonyl-containing compounds," Journal of Chromatography, 627 (1992) 1-16 (16 pages).
Chung, PO-REN, et al."Formaldehyde Gas Sensors: A Review," Sensors 2013, 13, 4468-4484 (17 pages).
Fuchs, Patricia, et al."Breath gas aldehydes as biomarkers of lung cancer," Int. J. Cancer 2010, 126 (11), 2663-70 (8 pages).
Hong Chan, Wing, et al."Optodes based on a calixarene ester for the determination of aldehydes via in situ generation of the Girard's reagent P derivative," Analyst 1998, 123 (12), 2851-2856 (6 pages).
Hoshika, Yasuyuki, et al. "Sensitive gas chromatographic determination of lower aliphatic carbonyl compounds as their pentafluorophenylhydrazones," Journal of Chromatography, 152 (1978) 224-227 (4 pages).
Knipp, Ralph J., et al."A versatile probe for chemoselective capture and analysis of carbonyl compounds in exhaled breath," Anal Methods, 2015, 7, 6027 (7 pages).
Kobayashi, Keiko, et al."Gas chromatrographic determination of low-molecular-weight carbonyl compounds in aqueous solution as their O-(2,3,4,5,6-pentafluorobenzyl) oximes," Journal of Chromatography A 1980, 187(2), 413-417 (5 pages).
Li, Junjie, et al."Development of a colorimetric sensor array for the discrimination of aldehydes," Sensors and Actuators B 196 (2014) 10-17 (8 pages).
Li, Mingxiao, et al. "Preconcentration and Analysis of Trace Volatile Carbonyl Compounds," Anal Chem 2012, 84(3), 1288-1293 (6 pages).
Poli, Diana, et al."Determination of aldehydes in exhaled breath of patients with lung cancer by means of on-fiber-derivatisation SPME-GC/MS," Journal of Chromatography B, 878 (2010) 2643-2651 (9 pages).
Vogel, Martin, et al."Hydrazine reagents as derivatizing agents in environmental analysis—a critical review," Fresenius J Anal Chem (2000) 366: 781-791 (11 pages).
"International Search Report and Written Opinion," for PCT Application No. PCT/US2021/033872 dated Sep. 13, 2021 (14 pages).
"Office Action," for Japanese Patent Application No. 2020-566542 dated Aug. 24, 2021 (9 pages) with English Translation.
"Response to Non-Final Rejection," dated May 25, 2021 for U.S. Appl. No. 16/393,177, submitted via EFS-Web on Aug. 19, 2021, 19 pages.
Meng, Zheng, et al. "Electrically-Transduced Chemical Sensors Based on Two-Dimensional Nanomaterials," Chem. Rev. 2019, 119, 478-598 (122 pages).
"First Examination Report," for Australian Patent Application No. 2019260666 dated Oct. 13, 2021 (4 pages).
"Response to Examination Report," for Australian Patent Application No. 2019260666 filed Oct. 29, 2021 (20 pages).
Allen, Matthew J. et al., "Honeycomb Carbon: A Review of Graphene," Chem. Rev. 2010, 110, 132-145 (14 pages).
An, Xiaohong et al., "Stable Aqueous Dispersions of Noncovalently Functionalized Graphene from Graphite and their Multifunctional High-Performance Applications," Nano Lett. 2010, 10, 4295-4301 (7 pages).

Bair, Kenneth W. et al., "(1-Pyrenylmethyl)amino Alcohols, a New Class of Antitumor DNA intercalators. Discovery and Initial Amine Side Chain Structure-Activity Studies," J. Med. Chem. 1990, 33, 2385-2393 (9 pages).
Bard, Allen J. et al., "Electrochemical Methods: Fundamentals and Applications," Wiley New York: 1980; vol. 2 (850 pages).
Biedermann, Frank et al., "Experimental Binding Energies in Supramolecular Complexes," Chem. Rev. 2016, 116(9), 5216-5300 (85 pages).
Bock, Harald et al., "Helicenes from Diarylmaleimides," Organic Letters 2014, 16, 1546-1549 (5 pages).
Boeseken, J. "The Use of Boric Acid for the Determination of the Configuration of Carbohydrates," Adv. Carbohydr. Chem. 1949, 4, 189-210 (22 pages).
Brust, Mathias et al., "Novel Gold-Dithiol Nano-Networks with Non-Metallic Electronic Properties," Adv. Mater. 1995, 7, No. 9 795-797 (3 pages).
Brust, Mathias et al., "Synthesis of Thiol-derivatised Gold Nanoparticles in a Two-phase Liquid-Liquid System," J. Chem. Soc., Chem. Commun., 1994, 801-802 (2 pages).
Cao, Mengmei et al., "Electrochemical and Theoretical Study of Π-Π stacking Interactions between Graphitic Surfaces and Pyrene Derivatives," J. Phys. Chem. C 2014, 118(5), 2650-2659 (10 pages).
Capuano, Rosamaria et al., "Corroles-Porphyrins: A Teamwork for Gas Sensor Arrays," Sensors, 2015, vol. 15, pp. 8121-8130 (10 pages).
Chamberlain, Richard V., II et al., "Electrostatically-induced Inclusion of Anions in Cyclodextrin Monolayers on Electrodes," Langmuir 2000, 1388-1396 (9 pages).
Cheng, Zengguang et al., "Suspended Graphene Sensors with Improved Signal and Reduced Noise," Nano Lett. 2010, 10, 1864-1868 (5 pages).
Connors, Kenneth A. et al., "The Stability of Cyclodextrin Complexes in Solution," Chem. Rev. 1997, 97, 1325-1357 (34 pages).
Deen, David A. et al., "Graphene-Based Quantum Capacitance Wireless Vapor Sensors," IEEE Sensors Journal, vol. 14, No. 5, May 2014, pp. 1459-1466 (8 pages).
Di Natale, Corrado et al., "Lung Cancer Identification by the Analysis of Breath by Means of an Array of Non-Selective Gas Sensors," Biosensors and Bioelectronics 18 (2003) 1209-1218 (10 pages).
Ebrish, M. A. et al., "Operation of Multi-Finger Graphene Quantum Capacitance Varactors using Planarized Local Bottom Gate Electrodes," Applied Physics Letters, vol. 100, No. 14, Apr. 2012 (4 pages).
Ebrish, Mona A. et al., "Effect of Noncovalent Basal Plane Functionalization of the Quantum Capacitance in Graphene," ACS Appl. Mater. Interfaces 2014, 6, 10296-10303 (8 pages).
Elemans, Johannes A. et al., "Molecular Materials by Self-Assembly of Porphyrins, Phthalocyanines, and Perylenes," Adv. Mater. 2006, 18, 1251-1266 (16 pages).
Fogel, Yulia et al., "Graphitic Nanoribons with Dibenzo[e,l]pyrene Repeat Units: Synthesis and Self-Assembly," Macromolecules 2009, 42, 6878-6884 (7 pages).
Gautam, Madhav et al., "Gas sensing properties of graphene synthesized by chemical vapor deposition," Materials and Science Engineering C31 (2011) 1405-1411 (7 pages).
Georgakilas, Vasilios et al., "Functionalization of Graphene: Covalent and Non-Covalent Approaches, Derivatives and Applications," Chem. Rev. 2012, 112(11), 6156-6214 (59 pages).
Georgakilas, Vasilios et al., "Noncovalent Functionalization of Graphene and Graphene Oxide for Energy Materials, Biosensing, Catalytic, and Biomedical Applications," Chem. Rev. 2016, 116, 5464-5519 (56 pages).
Ghosh, Sujoy et al., "Effect of 1-Pyrene Carboxylic-Acid Functionalization of Graphene on Its Capacitive Energy Storage," J. Phys. Chem. C 2012, 116, 20688-20693 (6 pages).
Good, Robert J. "Contact angle, wetting, and adhesion: a critical review," J. Adhesion Sci. Technol. 1992, vol. 6, No. 12, pp. 1269-1302 (34 pages).
Gorodetsky, Alon A. et al., "Electrochemistry Using Self-assembled DNA Monolayers on Highly Oriented Pyrolytic Graphite," Langmuir 2006, 22, 7917-7922 (6 pages).

(56) References Cited

OTHER PUBLICATIONS

Guo, Yujing et al., "Cyclodextrin Functionalized Graphene Nanosheets with High Supramolecular Recognition Capability: synthesis and Host-Guest Inclusion for Enhanced Electrochemical Performance," ACS Nano, 2010, abstract only (2 pages).
Guo, Zanru et al., "Light-Switchable Single-Walled Carbon Nanotubes Based on Host-Guest Chemistry," Adv. Funct. Mater. 2013, 23, 5010-5018 (18 pages).
Hill, Ernie W. et al., "Graphene Sensors," IEEE Sensors Journal, vol. 11, No. 12, Dec. 2011 (10 pages).
Hinnemo, Malkolm et al., "On Monolayer Formation of Pyrenebutyric Acid on Graphene," Langmuir, 2017, vol. 33, No. 14 pp. 3588-3593 (6 pages).
Hsiao, Min-Chien et al., "Preparation and properties of a graphene reinforced nanocomposite conducting plate," J. Mater. Chem., 2010, 20, 8496-8505 (10 pages).
Hsieh, Chien-Te et al., "Field emission from various CuO nanostructures," Applied Physics Letters 2003, vol. 83, No. 6 (3 pages).
Huang, Ke-Jing et al., "Novel electrochemical sensor based on functionalized graphene for simultaneous determination of adenine and guanine in DNA," Colloids and Surfaces B: Biointerfaces 82 (2011) 543-549 (7 pages).
Hunter, Christopher A. et al., "The Nature of Π-Π Interactions," J. Am. Chem. Soc. 1990, 112, 5525-5534 (10 pages).
Iezhokin, I. et al., "Porphyrin molecules boost the sensitivity of epitaxial graphene for NH3 detection," J. Phy.: Condens. Matter 29 (2017) (11 pages).
"International Preliminary Report on Patentability," for PCT Application No. PCT/US2019/018741 dated Sep. 3, 2020 (11 pages).
"International Preliminary Report on Patentability," for PCT Application No. PCT/US2019/028870 dated Nov. 5, 2020 (11 pages).
"International Search Report and Written Opinion," for PCT Application No. PCT/US2019/018741 dated May 6, 2019 (17 pages).
"International Search Report and Written Opinion," for PCT Application No. PCT/US2019/028870 dated Aug. 20, 2019 (17 pages).
"International Search Report and Written Opinion," for PCT Application No. PCT/US2020/046829 dated Nov. 18, 2020 (15 pages).
Jiao, Dezhi et al., "Supramolecular Peptide Amphiphile Vesicles through Host-Guest Complexation," Angew. Chem. Int. Ed. 2012, 51, 9633-9637 (5 pages).
Josef, Szejtli "Introduction and General Overview of Cyclodextrin Chemistry," Chem. Rev. 1998, 98, 1743-1753 (12 pages).
Kang, Xinhuang et al., "Glucose Oxidase-graphene-chitosan modified electrode for direct electrochemistry and glucose sensing," Biosensors and Bioelectronics 25 (2009) 901-905 (5 pages).
Koester, Steven J. "High Quality Factor Graphene Varactors for Wireless Sensing Applications," Applied Physics Letters 99, 163105 (2011), 3 pages.
Kozbial, Andrew et al., "Study on the surface energy of graphene by contact angle measurement," Langmuir 2014, 30 (28), 8598-8606 (28 pages).
Kuila, Tapas et al., "Chemical functionalization of graphene and its applications," Progress in Materials Science 57 (2012) 1061-1105 (45 pages).
Lauffer, Peter et al., "Molecular and electronic structure of PTCDA on bilayer graphene on SiC(0001) studied with scanning tunnerling microscopy," Phys. Stat. Sol. (b) 2008, 245, No. 10, 2064-2067 (4 pages).
Lechner, Christoph et al., "Adhesive Forces Between Aromatic Molecules and Graphene," The Journal of Physical Chemistry C 2014, 118(36), 20970-20981 (12 pages).
Lecourt, Thomas et al., "Triisobutylaluminium and Diisobutylaluminium Hydride as Molecular Scalpels: The Regioselective Stripping of Perbenzylate Sugars and Cyclodextrins," Chem. Eur. J. 2004, 10, 2960-2971 (12 pages).
Li, Errui et al., "Aliphatic Aldehyde Detection and Adsorption by Nonporous Adaptive Pillar[4]arene[1]quinone Crystals with Vapochromic Behavior," ACS Applied Materials & Interfaces, 2017, 10, 23147-23153 (23 pages).

Liu, Sophie F. et al., "Single-walled Carbon Nanotube-Metalloporphyrin Chemiresistive Gas Sensor Arrays for Volatile Organic Compounds," Chemistry of Materials, vol. 27, No. 10 (2015) pp. 3560-3563 (5 pages).
Liu, Yuxin et al., "Biological and Chemical Sensors based on Graphene Materials," Chem. Soc. Rev. 2012, 41 (6), 2283-2307 (27 pages).
Loh, Kian P. et al., "The Chemistry of Graphene," J. Mater. Chem., 2010, 20, 2277-2289 (13 pages).
Long, Brenda et al., "Non-Covalent Functionalization of Graphene Using Self-Assembly of Alkane-Amines," Adv. Funct. Mater. 2012, 22, 717-725 (9 pages).
Lu, Chun-Hua et al., "A Graphene Platform for Sensing Biomolecules," Angew. Chem. Int. Ed. 2009, 48, 4785-4787 (3 pages).
Machado, Roberto F. et al., "Detection of Lung Cancer by Sensor Array Analyses of Exhaled Breath," Am J Respir Crit Care Med, vol. 171, 1286-1291 (2005), 6 pages.
Mann, Jason A. et al., "Improving the Binding Characteristics of Tripodal Compounds on Single Layer Graphene," American Chemical Society 2013, vol. 7, No. 8, 7193-7199 (7 pages).
Manochehry, Sepehr et al., "Optical biosensors utilizing graphene and functional DNA molecules," J. Mater. Res. 2017, 32(15), 2973-2983 (11 pages).
Mao, Shun et al., "Specific Protein Detection Using Thermally Reduced Graphene Oxide Sheet Decorated with Gold Nanoparticle-Antibody Conjugates," Adv. Mater. 2010, 22, 3521-3526 (6 pages).
Nag, Sanada et al., "Ultrasensitive QRS made by supramolecular assembly of functionalized cyclodextrins and graphene for the detection of lung cancer VOC biomarkers," Journals of Materials Chemistry B 2014, 2, pp. 6571-6579 (9 pages).
Ohno, Yasuhide et al., "Electrolyte-Gated Graphene Field-Effect Transistors for Detecting pH and Protein Adsorption," Nano Letters 2009, vol. 9, No. 9, 3318-3322 (5 pages).
Olson, Eric J. et al., "Capacitive Sensing of Intercalated H2O Molecules Using Graphene," ACS Appl. Mater. Interfaces 2015, 7(46), 25804-25812 (29 pages).
Olson, Eric J. et al., "Getting More out of a Job Plot: Determination of Reactant to Product Stoichiometry in Cases of Displacement Reactions and nin Complex Formation," J. Org. Chem. 2011, 76, 8406-8412 (7 pages).
Pathipati, Srinivasa R. et al., "Modulation of charge transport properties of reduced graphene oxide by submonolayer physisorption of an organic dye," Organic Electronics 14 (2013) 1787-1792 (6 pages).
Peng, Gang et al., "Diagnosing lung cancer in exhaled breath using gold nanoparticles," Nature nanotechnology, 2009, 4(10), 669-673 (5 pages).
Peressi, Maria "Surface Functionalization of Graphene," Graphene Chemistry, John Wiley & Sons, Ltd:2013, pp. 233-253 (21 pages).
Poulston, S. et al., "Surface Oxidation and Reduction of CuO and Cu2O Studied Using XPS and XAES," Surface and Interface Analysis, vol. 24, 811-820 (10 pages).
Putta, Chandrababu et al., "Palladium Nanoparticles on Beta-Cyclodextrin Functionalised Graphene Nanosheets: a Supramolecular Based Heterogeneous Catalyst for C-C Coupling Reactions under Green Reaction Conditions," RSC Adv., 2015, 5, 6652-6660 (9 pages).
Rekharsky, Mikhail V. et al., "Complexation Thermodynamics of Cyclodextrins," Chem. Rev. 1998, 98, 1875-1917 (44 pages).
Reuillard, B. et al., "Non-covalent double functionalization of carbon nanotubes with a NADH oxidation Ru(II)-based molecular catalyst and a NAD-dependent glucose dehydrogenase," Chem. Commun. 2014, 50(79), 11731-11734 (5 pages).
Rodner, Marius et al., "Graphene Decorated with Iron Oxide Nanoparticles for Highly Sensitive Interaction with Volatile Organic Compounds," Sensors 2019, 19, 918-026 (9 pages).
Rojas, Maria T. et al., "Supported Monolayers Containing Preformed Binding-Sites—Synthesis and Interfacial Binding-Properties of a Thiolated Beta-Cyclodextrin Derivative," J. Am. Chem. Soc. 1995, 117, 336-343 (8 pages).
Rushi, A.D. et al., "Exercising Substituents in porphyrins for real time selective sensing of volatile organic compounds," Sensors and Actuators B: Chemical, vol. 257, 2018, pp. 389-397 (9 pages).

(56) References Cited

OTHER PUBLICATIONS

Schedin, F. et al., "Detection of Individual Gas Molecules Adsorbed on Graphene," Nat. Mater. 2007, 6(9), 652-655 (11 pages).
Shao, Yuyan "Graphene Based Electrochemical Sensor and Biosensors: A Review," Electroanalysis 2010, 22, No. 10, 1027-1036 (10 pages).
Shao, Yuyan et al., "Nitrogen-doped graphene and its electrochemical applications," J. Mater. Chem., 2010, 20, 7491-7496 (6 pages).
Song, Nan et al., "Applications of pillarenes, an emerging class of synthetic macrocycles," Science China Chemistry, 2014, 57(9), 1185-1198 (15 pages).
Swanson, Emily et al., "Self Assembly of Monolayers on Graphene with Pyrene and Cyclodextrin Derivatives," Research Poster. Elon University, LANDO program, Research Experience for Undergraduates Program of the National Science Foundation, Council of Undergraduate Research Experiences for Undergraduates symposium in Washington, D.C., Oct. 23-24, 2016 (1 page).
Terse-Thakoor, Trupti et al., "Graphene based biosensors for healthcare," J. Mater. Res. 2017, 32(15), 2905-2929 (25 pages).
Turkevich, John et al., "A study of the nucleation and growth processes in the synthesis of colloidal gold," Discuss. Faraday Soc., 1951, 11, 55-75 (23 pages).
Vincent, Mark A. et al., "Accurate Prediction of Adsorption Energies on Graphene, Using a Dispersion-Corrected Semiempirical Method Including Solvation," J. Chem. Inf. Model. 2014, 54, 2225-2260 (6 pages).
Wang, Lihua "A novel [beta]-cyclodextrin Functionalized Reduced Graphene Oxide Electrochemical Sensor for Blood Glucose Detection," International Journal of Electrochemical Science, Dec. 28, 2017 pp. 1594-1602 (9 pages).
Wang, Qing Hua et al., "Room-temperature molecular-resolution characterization of self-assembled organic monolayers on epitaxial graphene," Nature Chemistry 2009 vol. 1 (3), 206-211 (6 pages).
Wayu, Mulugeta B. et al., "Electropolymerization of Beta-Cyclodextrin onto Multi-Walled Carbon Nanotube Composite Films for Enhanced Selective Detection of Uric Acid," Journal of Electroanalytical Chemistry 783 (2016), 192-200 (9 pages).
Xu, Yuxi et al., "Flexible Graphene Films via the Filtration of Water-Soluble Noncovalent Functionalized Graphene Sheets," J. Am. Chem. Soc. 2008, 130, 5856-5857 (2 pages).
Xu, Huifeng et al., "Direct Electrochemistry and electrocatalysis of hemoglobin protein entrapped in graphene and chitosan composite film," Talanta 81 (2010) 334-338 (5 pages).
Yavari, Fazel et al., "Graphene-Based Chemical Sensors," J. Phys. Chem. Lett. 2012, 3, 1746-1753 (8 pages).
Zhang, Yao et al., "Capacitive Sensing of Glucose in Electrolytes using Graphene Quantum Capacitance Varactors," ACS Appl. Mater. Interfaces 2017, 9, 38863-38869 (7 pages).
Zhang, Yao et al., "Glucose Sensing with Graphene Varactors," IEEE Sensors, SENSORS 2016—Proceedings, Orlando, FL 2016 (3 pages).
Zhang, Yiheng et al., "Direct Measurements of the Interaction between Pyrene and Graphite in Aqueous Media by Single Molecule Force Spectroscopy: Understanding the Π-ΠInteractions," Langmuir 2007, 23, 7911-7915 (5 pages).
Zhao, Yan-Li et al., "Noncovalent Functionalization of Single-Walled Carbon Nanotubes," Accounts of Chemical Research 2009, vol. 42, No. 8. 1161-1171 (12 pages).
Zhen, Xue et al., "Noncovalent Monolayer Modification of Graphene Using Pyrene and Cyclodextrin Receptors for Chemical Sensing," ACS Applied Nano Materials 2018, vol. 1, No. 6 pp. 2718-2726 (9 pages).
Zhu, Congzhi et al., "Mingling Electronic Chemical Sensors with Supramolecular Host-Guest Chemistry," Current Organic Chemistry, 2014, 18, 1957-1964 (8 pages).
Zhu, Yanwu et al., "Graphene and Graphene Oxide: Synthesis, Properties, and Applications," Adv. Mater. 2010, 22, 3906-3924 (19 pages).
"Notice of Allowance," for U.S. Appl. No. 16/393,177 dated Dec. 15, 2021 (21 pages).
"Office Action," for Japanese Patent Application No. 2020-558952 dated Dec. 7, 2021 (6 pages) with English Translation.
"Communication Pursuant to Article 94(3) EPC," for European Patent Application No. 19709268.7 dated Sep. 13, 2022 (5 pages).
"International Preliminary Report on Patentability," for PCT Application No. PCT/US2021/033872 dated Dec. 8, 2022 (7 pages).
"Response to Communication Pursuant to Rules 161(1) and 162 EPC," for European Patent Application No. 20764525.0 filed Oct. 5, 2022 (27 pages).
"Communication Pursuant to Article 94(3) EPC," for European Patent Application No. 20764525.0 dated Aug. 16, 2023 (6 pages).
"Notice of Allowance," for U.S. Appl. No. 17/707,214 dated Aug. 29, 2023 (18 pages).
"Second Office Action," for Chinese Patent Application No. 201980027577.2 dated Aug. 18, 2023 (4 pages) with English Summary.
"Non-Final Office Action," for U.S. Appl. No. 17/387,503 dated Aug. 16, 2023 (51 pages).
"Office Action," for Japanese Patent Application No. 2022-511117 dated May 23, 2023 (12 pages), with English translation.
"Response to Non-Final Rejection," dated Mar. 17, 2023 for U.S. Appl. No. 17/707,214, submitted via EFS-Web on Jun. 13, 2023, 8 pages.
Seo, Sohyeon, et al. "A Molecular Approach to an Electrostatic Hydrogen Evolution Reaction on Single-Layer Graphene," Nanoscale 9.11 (2017): 3969-3979 (11 pages).
"First Office Action," for Chinese Patent Application No. 202080058470.4 dated Sep. 12, 2023 (14 pages) with English Summary.
"International Preliminary Report on Patentability," for PCT Application No. PCT/US2022/019728 dated Sep. 28, 2023 (7 pages).
"Office Action," for Japanese Patent Application No. 2022-570412 dated Oct. 31, 2023 (6 pages) with English Summary.
"Response to Communication Pursuant to Article 94(3) EPC," for European Patent Application No. 20764525.0 filed Dec. 5, 2023 (121 pages).
"Response to Non-Final Rejection," dated Aug. 16, 2023, for U.S. Appl. No. 17/387,503, submitted via EFS-Web on Nov. 7, 2023, 11 pages.

\* cited by examiner

NON-COVALENT MODIFICATION OF GRAPHENE-BASED CHEMICAL SENSORS

This application claims the benefit of U.S. Provisional Application No. 62/889,387, filed Aug. 20, 2019, the content of which is herein incorporated by reference in its entirety.

FIELD

Embodiments herein relate to chemical sensors, devices and systems including the same, and related methods. More specifically, embodiments herein relate to chemical sensors based on the non-covalent surface modification of graphene.

BACKGROUND

The accurate detection of diseases can allow clinicians to provide appropriate therapeutic interventions. The early detection of diseases can lead to better treatment outcomes. Diseases can be detected using many different techniques including analyzing tissue samples, analyzing various bodily fluids, diagnostic scans, genetic sequencing, and the like.

Some disease states result in the production of specific chemical compounds. In some cases, volatile organic compounds (VOCs) released into a gaseous sample of a patient can be hallmarks of certain diseases. The detection of these compounds or differential sensing of the same can allow for the early detection of particular disease states.

SUMMARY

In a first aspect, a medical device is included having a graphene varactor including a graphene layer and a self-assembled monolayer disposed on an outer surface of the graphene layer through non-covalent interactions between the self-assembled monolayer and a π-electron system of graphene. The self-assembled monolayer can include one or more pillarenes, substituted pillarenes, calixarenes, substituted calixarenes, peralkylated cyclodextrins, substituted peralkylated cyclodextrins, pyrenes, or substituted pyrenes, or derivatives thereof.

In a second aspect, in addition to one or more of the preceding or following aspects, or in the alternative to some aspects, the self-assembled monolayer provides a Langmuir theta value of at least 0.9.

In a third aspect, in addition to one or more of the preceding or following aspects, or in the alternative to some aspects, the self-assembled monolayer provides a Langmuir theta value of at least 0.98.

In a fourth aspect, in addition to one or more of the preceding or following aspects, or in the alternative to some aspects, the self-assembled monolayer provides coverage over the graphene from 50% to 150% by surface area.

In a fifth aspect, in addition to one or more of the preceding or following aspects, or in the alternative to some aspects, can include a plurality of graphene varactors configured in an array on the medical device.

In a sixth aspect, in addition to one or more of the preceding or following aspects, or in the alternative to some aspects, the self-assembled monolayer can include substituted pillarenes of the formula:

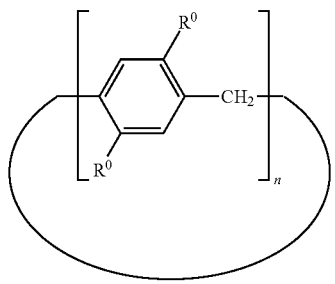

where each $R^0$ can independently include: $-R^1$, $-OR^1$, or $-SR^1$; and where each $R^1$ can independently include: $-H$; $-OH$; $=O$; any linear, branched, or cyclic $C_1$-$C_{20}$ alkyl, $C_1$-$C_{20}$ alkenyl, $C_1$-$C_{20}$ alkynyl, $C_1$-$C_{20}$ heteroalkyl, $C_1$-$C_{20}$ heteroalkenyl, $C_1$-$C_{20}$ heteroalkynyl, $C_1$-$C_{20}$ haloalkyl groups, $C_1$-$C_{20}$ haloalkenyl groups, $C_1$-$C_{20}$ haloalkynyl groups, $C_1$-$C_{20}$ halogenated heteroalkyl groups, $C_1$-$C_{20}$ halogenated heteroalkenyl groups, $C_1$-$C_{20}$ halogenated heteroalkynyl groups, or any combinations thereof, an aryl, heteroaryl, substituted aryl, substituted heteroaryl aryl, halogenated aryl, substituted halogenated aryl, a benzyl or a substituted benzyl, a biphenyl or substituted biphenyl, an aryloxy, arylthio, arylamine, or any substitutions thereof, $-R^2OH$, $-R^2C(O)OH$, $-R^2C(O)OR^2$, $-R^2OR^2$, $-R^2SR^2$, $-R^2CHO$, $-R^2X$ where X is a halogen atom, $-R^2C(O)NH_2$, $-R^2C(O)NR^2$, $-R^2NH_3^+$, $-R^2NH_2$, $-R^2NO^2$, $-R^2NHR^2$, $-R^2NR^2R^2$, $-R^2N_3$, $-R^2OPO(OH)_2$, $-R^2OSO(OH)_2$, or any derivatives or combinations thereof; where each $R^2$ can independently include any identical or different, linear, branched, or cyclic $C_1$-$C_{20}$ alkyl, $C_1$-$C_{20}$ alkenyl, $C_1$-$C_{20}$ alkynyl, $C_1$-$C_{20}$ heteroalkyl, $C_1$-$C_{20}$ heteroalkenyl, $C_1$-$C_{20}$ heteroalkynyl, $C_1$-$C_{20}$ haloalkyl groups, $C_1$-$C_{20}$ haloalkenyl groups, $C_1$-$C_{20}$ haloalkynyl groups, $C_1$-$C_{20}$ halogenated heteroalkyl groups, $C_1$-$C_{20}$ halogenated heteroalkenyl groups, $C_1$-$C_{20}$ halogenated heteroalkynyl groups, or any substitutions or combinations thereof, and where n is an integer from at least 5 to 15.

In a seventh aspect, in addition to one or more of the preceding or following aspects, or in the alternative to some aspects, where at least some of the $R^0$ substituents differ from the other $R^0$ substituents.

In an eighth aspect, in addition to one or more of the preceding or following aspects, or in the alternative to some aspects, the self-assembled monolayer can include substituted pillarenes of the formula:

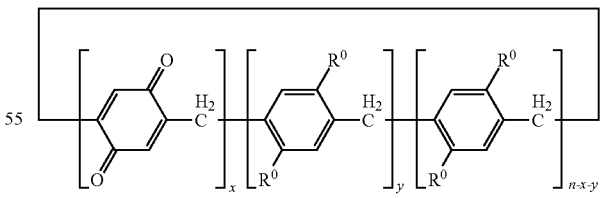

where each $R^0$ can independently include: $-R^1$, $-OR^1$, or $-SR^1$; and where each $R^1$ can independently include: $-H$; $-OH$; $=O$; any linear, branched, or cyclic $C_1$-$C_{20}$ alkyl, $C_1$-$C_{20}$ alkenyl, $C_1$-$C_{20}$ alkynyl, $C_1$-$C_{20}$ heteroalkyl, $C_1$-$C_{20}$ heteroalkenyl, $C_1$-$C_{20}$ heteroalkynyl, $C_1$-$C_{20}$ haloalkyl groups, $C_1$-$C_{20}$ haloalkenyl groups, $C_1$-$C_{20}$ haloalkynyl groups, $C_1$-$C_{20}$ halogenated heteroalkyl groups, $C_1$-$C_{20}$ halogenated heteroalkenyl groups, $C_1$-$C_{20}$ halogenated heteroalkynyl groups, or any combinations thereof, an aryl, heteroaryl, substituted aryl, substituted heteroaryl aryl, halogenated aryl, substituted halogenated aryl, a benzyl or a substituted benzyl, a biphenyl or substituted biphenyl, an aryloxy, arylthio, arylamine, or any substitutions thereof, —$R^2OH$, —$R^2C(O)OH$, —$R^2C(O)OR^2$, —$R^2OR^2$, —$R^2SR^2$, —$R^2CHO$, —$R^2X$ where X is a halogen atom, —$R^2C(O)NH_2$, —$R^2C(O)NR^2$, —$R^2NH_3^+$, —$R^2NH_2$, —$R^2NO_2$, —$R^2NHR^2$, —$R^2NR^2R^2$, —$R^2N_3$, —$R^2OPO(OH)_2$, —$R^2OSO(OH)_2$, or any derivatives or combinations thereof; where each $R^2$ can independently include any identical or different, linear, branched, or cyclic $C_1$-$C_{20}$ alkyl, $C_1$-$C_{20}$ alkenyl, $C_1$-$C_{20}$ alkynyl, $C_1$-$C_{20}$ heteroalkyl, $C_1$-$C_{20}$ heteroalkenyl, $C_1$-$C_{20}$ heteroalkynyl, $C_1$-$C_{20}$ haloalkyl groups, $C_1$-$C_{20}$ haloalkenyl groups, $C_1$-$C_{20}$ haloalkynyl groups, $C_1$-$C_{20}$ halogenated heteroalkyl groups, $C_1$-$C_{20}$ halogenated heteroalkenyl groups, $C_1$-$C_{20}$ halogenated heteroalkynyl groups, or any substitutions or combinations thereof, and where x is an integer from at least 0 to 15, y is an integer from at least 0 to 15, and n is an integer from at least 5 to 15.

In a ninth aspect, in addition to one or more of the preceding or following aspects, or in the alternative to some aspects, the self-assembled monolayer can include substituted calixarenes can include any of:

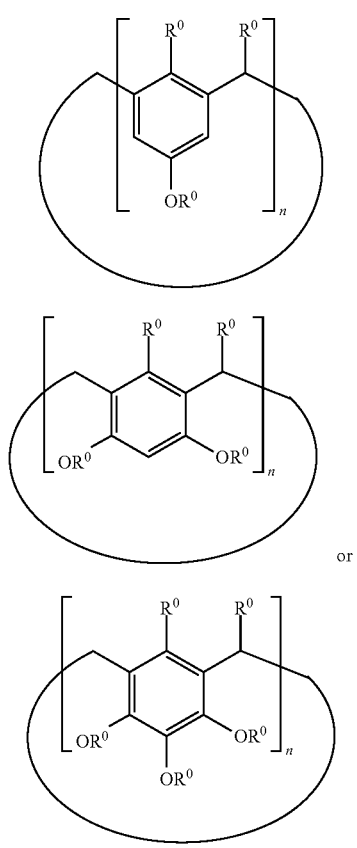

where each $R^0$ can independently include: —$R^1$, —$OR^1$, or —$SR^1$; and where each $R^1$ can independently include: —H; —OH; any linear, branched, or cyclic $C_1$-$C_{20}$ alkyl, $C_1$-$C_{20}$ alkenyl, $C_1$-$C_{20}$ alkynyl, $C_1$-$C_{20}$ heteroalkyl, $C_1$-$C_{20}$ heteroalkenyl, $C_1$-$C_{20}$ heteroalkynyl, $C_1$-$C_{20}$ haloalkyl groups, $C_1$-$C_{20}$ haloalkenyl groups, $C_1$-$C_{20}$ haloalkynyl groups, $C_1$-$C_{20}$ halogenated heteroalkyl groups, $C_1$-$C_{20}$ halogenated heteroalkenyl groups, $C_1$-$C_{20}$ halogenated heteroalkynyl groups, or any combinations thereof, an aryl, heteroaryl, substituted aryl, substituted heteroaryl aryl, halogenated aryl, substituted halogenated aryl, a biphenyl or substituted biphenyl, an aryloxy, arylthio, arylamine, or any substitutions thereof, —$R^2OH$, —$R^2C(O)OH$, —$R^2C(O)OR^2$, —$R^2OR^2$, —$R^2SR^2$, —$R^2CHO$, —$R^2X$ where X is a halogen atom, —$R^2C(O)NH_2$, —$R^2C(O)NR^2$, —$R^2NH_3^+$, —$R^2NH_2$, —$R^2NO_2$, —$R^2NHR^2$, —$R^2NR^2R^2$, —$R^2N_3$, —$R^2OPO(OH)_2$, —$R^2OSO(OH)_2$, or any derivatives or combinations thereof; where each $R^2$ can independently include any identical or different, linear, branched, or cyclic $C_1$-$C_{20}$ alkyl, $C_1$-$C_{20}$ alkenyl, $C_1$-$C_{20}$ alkynyl, $C_1$-$C_{20}$ heteroalkyl, $C_1$-$C_{20}$ heteroalkenyl, $C_1$-$C_{20}$ heteroalkynyl, $C_1$-$C_{20}$ haloalkyl groups, $C_1$-$C_{20}$ haloalkenyl groups, $C_1$-$C_{20}$ haloalkynyl groups, $C_1$-$C_{20}$ halogenated heteroalkyl groups, $C_1$-$C_{20}$ halogenated heteroalkenyl groups, $C_1$-$C_{20}$ halogenated heteroalkynyl groups, or any substitutions or combinations thereof, and where n is an integer from at least 3 to 15.

In a tenth aspect, in addition to one or more of the preceding or following aspects, or in the alternative to some aspects, the self-assembled monolayer can include substituted peralkylated cyclodextrins of the formula:

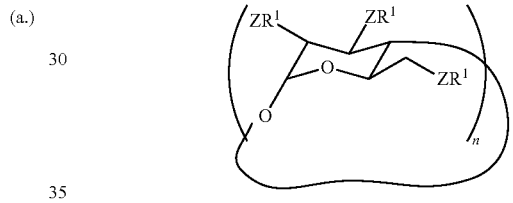

where each Z can independently include: —S or —O; and where each $R^1$ can independently include: —H; —OH; any linear, branched, or cyclic $C_1$-$C_{20}$ alkyl, $C_1$-$C_{20}$ alkenyl, $C_1$-$C_{20}$ alkynyl, $C_1$-$C_{20}$ heteroalkyl, $C_1$-$C_{20}$ heteroalkenyl, $C_1$-$C_{20}$ heteroalkynyl, $C_1$-$C_{20}$ haloalkyl groups, $C_1$-$C_{20}$ haloalkenyl groups, $C_1$-$C_{20}$ haloalkynyl groups, $C_1$-$C_{20}$ halogenated heteroalkyl groups, $C_1$-$C_{20}$ halogenated heteroalkenyl groups, $C_1$-$C_{20}$ halogenated heteroalkynyl groups, or any combinations thereof, an aryl, heteroaryl, substituted aryl, substituted heteroaryl aryl, halogenated aryl, substituted halogenated aryl, a benzyl or a substituted benzyl, a biphenyl or substituted biphenyl, an aryloxy, arylthio, arylamine, or any substitutions thereof; —$R^2OH$, —$R^2C(O)OH$, —$R^2C(O)OR^2$, —$R^2OR^2$, —$R^2SR^2$, —$R^2CHO$, —$R^2X$ where X is a halogen atom, —$R^2C(O)NH_2$, —$R^2C(O)NR^2$, —$R^2NH_3^+$, —$R^2NH_2$, —$R^2NO_2$, —$R^2NHR^2$, —$R^2NR^2R^2$, —$R^2N_3$, —$R^2OPO(OH)_2$, —$R^2OSO(OH)_2$, or any derivatives or combinations thereof; where each $R^2$ can independently include any identical or different, linear, branched, or cyclic $C_1$-$C_{20}$ alkyl, $C_1$-$C_{20}$ alkenyl, $C_1$-$C_{20}$ alkynyl, $C_1$-$C_{20}$ heteroalkyl, $C_1$-$C_{20}$ heteroalkenyl, $C_1$-$C_{20}$ heteroalkynyl, $C_1$-$C_{20}$ haloalkyl groups, $C_1$-$C_{20}$ haloalkenyl groups, $C_1$-$C_{20}$ haloalkynyl groups, $C_1$-$C_{20}$ halogenated heteroalkyl groups, $C_1$-$C_{20}$ halogenated heteroalkenyl groups, $C_1$-$C_{20}$ halogenated heteroalkynyl groups, or any substitutions or combinations thereof, and where n is an integer from at least 5 to 10.

In an eleventh aspect, a method of modifying a surface of graphene is provided. The method can include forming a self-assembled monolayer disposed on an outer surface of a graphene layer through non-covalent interactions between the self-assembled monolayer and a π-electron system of graphene. The self-assembled monolayer can include one or more pillarenes, substituted pillarenes, calixarenes, substituted calixarenes, peralkylated cyclodextrins, substituted peralkylated cyclodextrins, pyrenes, or substituted pyrenes, or derivatives thereof. The method can include quantifying an extent of surface coverage of the self-assembled monolayer using contact angle goniometry, Raman spectroscopy, or X-Ray photoelectron spectroscopy.

In a twelfth aspect, in addition to one or more of the preceding or following aspects, or in the alternative to some aspects, the method further can include selecting derivatized graphene layers that exhibit a Langmuir theta value of at least 0.9.

In a thirteenth aspect, in addition to one or more of the preceding or following aspects, or in the alternative to some aspects, the method further can include selecting derivatized graphene layers that exhibit a Langmuir theta value of at least 0.98.

In a fourteenth aspect, in addition to one or more of the preceding or following aspects, or in the alternative to some aspects, the self-assembled monolayer suitable for use with the methods herein can include substituted pillarenes of the formula:

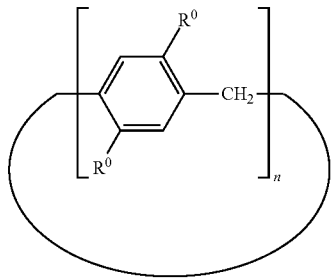

where each $R^0$ can independently include: $-R^1$, $-OR^1$, or $-SR^1$; and where each $R^1$ can independently include: $-H$; $-OH$; $=O$; any linear, branched, or cyclic $C_1$-$C_{20}$ alkyl, $C_1$-$C_{20}$ alkenyl, $C_1$-$C_{20}$ alkynyl, $C_1$-$C_{20}$ heteroalkyl, $C_1$-$C_{20}$ heteroalkenyl, $C_1$-$C_{20}$ heteroalkynyl, $C_1$-$C_{20}$ haloalkyl groups, $C_1$-$C_{20}$ haloalkenyl groups, $C_1$-$C_{20}$ haloalkynyl groups, $C_1$-$C_{20}$ halogenated heteroalkyl groups, $C_1$-$C_{20}$ halogenated heteroalkenyl groups, $C_1$-$C_{20}$ halogenated heteroalkynyl groups, or any combinations thereof, an aryl, heteroaryl, substituted aryl, substituted heteroaryl aryl, halogenated aryl, substituted halogenated aryl, a benzyl or a substituted benzyl, a biphenyl or substituted biphenyl, an aryloxy, arylthio, arylamine, or any substitutions thereof, $-R^2OH$, $-R^2C(O)OH$, $-R^2C(O)OR^2$, $-R^2OR^2$, $-R^2SR^2$, $-R^2CHO$, $-R^2X$ where X is a halogen atom, $-R^2C(O)NH^2$, $-R^2C(O)NR^2$, $-R^2NH_3^+$, $-R^2NH^2$, $-R^2NO^2$, $-R^2NHR^2$, $-R^2NR^2R^2$, $-R^2N_3$, $-R^2OPO(OH)^2$, $-R^2OSO(OH)^2$, or any derivatives or combinations thereof, where each $R^2$ can independently include any identical or different, linear, branched, or cyclic $C_1$-$C_{20}$ alkyl, $C_1$-$C_{20}$ alkenyl, $C_1$-$C_{20}$ alkynyl, $C_1$-$C_{20}$ heteroalkyl, $C_1$-$C_{20}$ heteroalkenyl, $C_1$-$C_{20}$ heteroalkynyl, $C_1$-$C_{20}$ haloalkyl groups, $C_1$-$C_{20}$ haloalkenyl groups, $C_1$-$C_{20}$ haloalkynyl groups, $C_1$-$C_{20}$ halogenated heteroalkyl groups, $C_1$-$C_{20}$ halogenated heteroalkenyl groups, $C_1$-$C_{20}$ halogenated heteroalkynyl groups, or any substitutions or combinations thereof, and where n is an integer from at least 5 to 15.

In a fifteenth aspect, in addition to one or more of the preceding or following aspects, or in the alternative to some aspects, where the self-assembled monolayer includes substituted pillarenes of the formula:

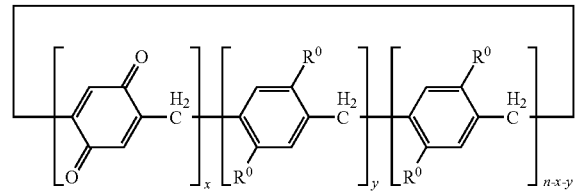

where each $R^0$ can independently include: $-R^1$, $-OR^1$, or $-SR^1$; and where each R can independently include: $-H$; $-OH$; any linear, branched, or cyclic $C_1$-$C_{20}$ alkyl, $C_1$-$C_{20}$ alkenyl, $C_1$-$C_{20}$ alkynyl, $C_1$-$C_{20}$ heteroalkyl, $C_1$-$C_{20}$ heteroalkenyl, $C_1$-$C_{20}$ heteroalkynyl, $C_1$-$C_{20}$ haloalkyl groups, $C_1$-$C_{20}$ haloalkenyl groups, $C_1$-$C_{20}$ haloalkynyl groups, $C_1$-$C_{20}$ halogenated heteroalkyl groups, $C_1$-$C_{20}$ halogenated heteroalkenyl groups, $C_1$-$C_{20}$ halogenated heteroalkynyl groups, or any combinations thereof, an aryl, heteroaryl, substituted aryl, substituted heteroaryl aryl, halogenated aryl, substituted halogenated aryl, a benzyl or a substituted benzyl, a biphenyl or substituted biphenyl, an aryloxy, arylthio, arylamine, or any substitutions thereof, $-R^2OH$, $-R^2C(O)OH$, $-R^2C(O)OR^2$, $-R^2OR^2$, $-R^2SR^2$, $-R^2CHO$, $-R^2X$ where X is a halogen atom, $-R^2C(O)NH_2$, $-R^2C(O)NR^2$, $-R^2NH_3^+$, $-R^2NH_2$, $-R^2NO_2$, $-R^2NR^2$, $-R^2NR^2R^2$, $-R^2N_3$, $-R^2OPO(OH)_2$, $-R^2OSO(OH)_2$, or any derivatives or combinations thereof; where each $R^2$ can independently include any identical or different, linear, branched, or cyclic $C_1$-$C_{20}$ alkyl, $C_1$-$C_{20}$ alkenyl, $C_1$-$C_{20}$ alkynyl, $C_1$-$C_{20}$ heteroalkyl, $C_1$-$C_{20}$ heteroalkenyl, $C_1$-$C_{20}$ heteroalkynyl, $C_1$-$C_{20}$ haloalkyl groups, $C_1$-$C_{20}$ haloalkenyl groups, $C_1$-$C_{20}$ haloalkynyl groups, $C_1$-$C_{20}$ halogenated heteroalkyl groups, $C_1$-$C_{20}$ halogenated heteroalkenyl groups, $C_1$-$C_{20}$ halogenated heteroalkynyl groups, or any substitutions or combinations thereof, and where x is an integer from at least 0 to 15, y is an integer from at least 0 to 15, and n is an integer from at least 5 to 15.

In a sixteenth aspect, in addition to one or more of the preceding or following aspects, or in the alternative to some aspects, where the self-assembled monolayer includes substituted calixarenes can include any of:

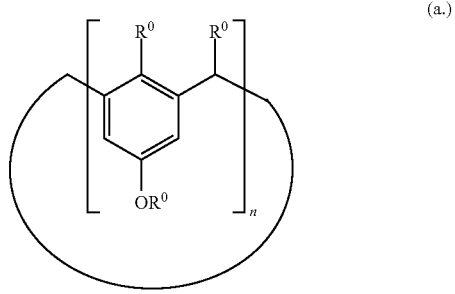

(a.)

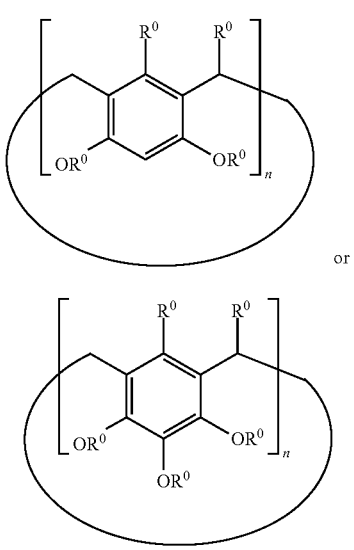

where each $R^0$ can independently include: —$R^1$, —$OR^1$, or —$SR^1$; and where each $R^1$ can independently include: —H; —OH; any linear, branched, or cyclic $C_1$-$C_{20}$ alkyl, $C_1$-$C_{20}$ alkenyl, $C_1$-$C_{20}$ alkynyl, $C_1$-$C_{20}$ heteroalkyl, $C_1$-$C_{20}$ heteroalkenyl, $C_1$-$C_{20}$ heteroalkynyl, $C_1$-$C_{20}$ haloalkyl groups, $C_1$-$C_{20}$ haloalkenyl groups, $C_1$-$C_{20}$ haloalkynyl groups, $C_1$-$C_{20}$ halogenated heteroalkyl groups, $C_1$-$C_{20}$ halogenated heteroalkenyl groups, $C_1$-$C_{20}$ halogenated heteroalkynyl groups, or any combinations thereof, an aryl, heteroaryl, substituted aryl, substituted heteroaryl aryl, halogenated aryl, substituted halogenated aryl, a benzyl or a substituted benzyl, a biphenyl or substituted biphenyl, an aryloxy, arylthio, arylamine, or any substitutions thereof, —$R^2OH$, —$R^2C(O)OH$, —$R^2C(O)OR^2$, —$R^2OR^2$, —$R^2SR^2$, —$R^2CHO$, —$R^2X$ where X is a halogen atom, —$R^2C(O)NH_2$, —$R^2C(O)NR^2$, —$R^2NH_3^+$, —$R^2NH_2$, —$R^2NO_2$, —$R^2NHR^2$, —$R^2NR^2R^2$, —$R^2N_3$, —$R^2OPO(OH)_2$, —$R^2OSO(OH)_2$, or any derivatives or combinations thereof; where each $R^2$ can independently include any identical or different, linear, branched, or cyclic $C_1$-$C_{20}$ alkyl, $C_1$-$C_{20}$ alkenyl, $C_1$-$C_{20}$ alkynyl, $C_1$-$C_{20}$ heteroalkyl, $C_1$-$C_{20}$ heteroalkenyl, $C_1$-$C_{20}$ heteroalkynyl, $C_1$-$C_{20}$ haloalkyl groups, $C_1$-$C_{20}$ haloalkenyl groups, $C_1$-$C_{20}$ haloalkynyl groups, $C_1$-$C_{20}$ halogenated heteroalkyl groups, $C_1$-$C_{20}$ halogenated heteroalkenyl groups, $C_1$-$C_{20}$ halogenated heteroalkynyl groups, or any substitutions or combinations thereof, and where n is an integer from at least 3 to 15.

In a seventeenth aspect, in addition to one or more of the preceding or following aspects, or in the alternative to some aspects, where the self-assembled monolayer includes substituted peralkylated cyclodextrins can include:

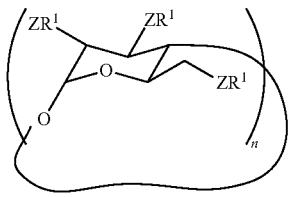

where each $R^0$ can independently include: —$R^1$, —$OR^1$, or —$SR^1$; and where each $R^1$ can independently include: —H; any linear, branched, or cyclic $C_1$-$C_{20}$ alkyl, $C_1$-$C_{20}$ alkenyl, $C_1$-$C_{20}$ alkynyl, $C_1$-$C_{20}$ heteroalkyl, $C_1$-$C_{20}$ heteroalkenyl, $C_1$-$C_{20}$ heteroalkynyl, $C_1$-$C_{20}$ haloalkyl groups, $C_1$-$C_{20}$ haloalkenyl groups, $C_1$-$C_{20}$ haloalkynyl groups, $C_1$-$C_{20}$ halogenated heteroalkyl groups, $C_1$-$C_{20}$ halogenated heteroalkenyl groups, $C_1$-$C_{20}$ halogenated heteroalkynyl groups, or any combinations thereof, an aryl, heteroaryl, substituted aryl, substituted heteroaryl aryl, halogenated aryl, substituted halogenated aryl, a benzyl or a substituted benzyl, a biphenyl or substituted biphenyl, an aryloxy, arylthio, arylamine, or any substitutions thereof, —$R^2OH$, —$R^2C(O)OH$, —$R^2C(O)OR^2$, —$R^2OR^2$, —$R^2SR^2$, —$R^2CHO$, —$R^2X$ where X is a halogen atom, —$R^2C(O)NH_2$, —$R^2C(O)NR^2$, —$R^2NH_3^+$, —$R^2NH_2$, —$R^2NO_2$, —$R^2NHR^2$, —$R^2NR^2R^2$, —$R^2N_3$, —$R^2OPO(OH)_2$, —$R^2OSO(OH)_2$, or any derivatives or combinations thereof; where each $R^2$ can independently include any identical or different, linear, branched, or cyclic $C_1$-$C_{20}$ alkyl, $C_1$-$C_{20}$ alkenyl, $C_1$-$C_{20}$ alkynyl, $C_1$-$C_{20}$ heteroalkyl, $C_1$-$C_{20}$ heteroalkenyl, $C_1$-$C_{20}$ heteroalkynyl, $C_1$-$C_{20}$ haloalkyl groups, $C_1$-$C_{20}$ haloalkenyl groups, $C_1$-$C_{20}$ haloalkynyl groups, $C_1$-$C_{20}$ halogenated heteroalkyl groups, $C_1$-$C_{20}$ halogenated heteroalkenyl groups, $C_1$-$C_{20}$ halogenated heteroalkynyl groups, or any substitutions or combinations thereof, and where n is an integer from at least 5 to 10.

In an eighteenth aspect, a method for detecting an analyte is included. The method can include collecting a gaseous sample and contacting the gaseous sample with one or more graphene varactors. Each of the one or more graphene varactors can include a graphene layer and a self-assembled monolayer disposed on an outer surface of the graphene layer through non-covalent interactions between the self-assembled monolayer and a π-electron system of graphene. The self-assembled monolayer can include at least one selected from the group consisting of pillarenes, substituted pillarenes, calixarenes, substituted calixarenes, peralkylated cyclodextrins, substituted peralkylated cyclodextrins, pyrenes, or substituted pyrenes, or derivatives thereof.

In a nineteenth aspect, in addition to one or more of the preceding or following aspects, or in the alternative to some aspects, the method further can include measuring a differential response in an electrical property of the one or more graphene varactors due to binding of one or more analytes present in the gaseous sample.

In a twentieth aspect, in addition to one or more of the preceding or following aspects, or in the alternative to some aspects, the electrical property can be selected from the group consisting of capacitance or resistance.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE FIGURES

Aspects may be more completely understood in connection with the following figures (FIGS.), in which.

Figure 1:
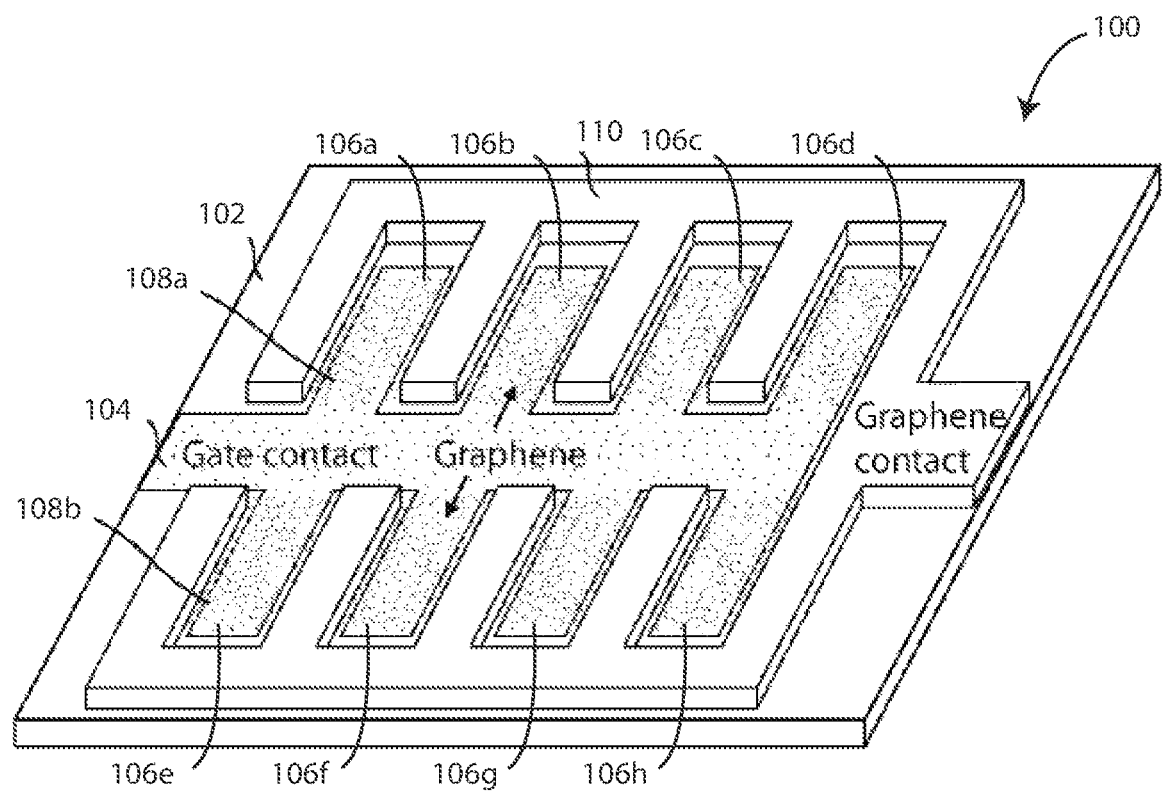
FIG. 1 is a schematic perspective view of a graphene varactor in accordance with various embodiments herein.

While embodiments are susceptible to various modifications and alternative forms, specifics thereof have been shown by way of example and drawings, and will be described in detail. It should be understood, however, that the scope herein is not limited to the particular aspects described. On the contrary, the intention is to cover modifications, equivalents, and alternatives falling within the spirit and scope herein.

DETAILED DESCRIPTION

Embodiments herein relate to chemical sensors, medical devices and systems including the same, and related methods for detecting chemical compounds in gaseous samples, such as, but not limited to, the breath of a patient. In some embodiments, the chemical sensors herein can be based on the non-covalent surface modification of graphene with various surface receptors, including pillarenes, substituted pillarenes, calixarenes, substituted calixarenes, peralkylated cyclodextrins, substituted peralkylated cyclodextrins, pyrenes, or substituted pyrenes. As used herein, the term "pillarene" can be used interchangeably with the term "pillararene."

Graphene is a form of carbon containing a single layer of carbon atoms in a hexagonal lattice. Graphene has a high strength and stability due to its tightly packed $sp^2$ hybridized orbitals, where each carbon atom forms one sigma ($\sigma$) bond each with its three neighboring carbon atoms and has one p orbital projected out of the hexagonal plane. The p orbitals of the hexagonal lattice can hybridize to form a $\pi$ band on the surface of graphene that is suitable for non-covalent electrostatic interactions, including $\pi$-$\pi$ stacking interactions with other molecules.

Pillarenes are a group of heterocyclic macrocycles having 5 to 15 modified hydroquinone subunits, each connected by a methylene (—$CH_2$—) bridge. The basic core structure of a pillarene is as follows:

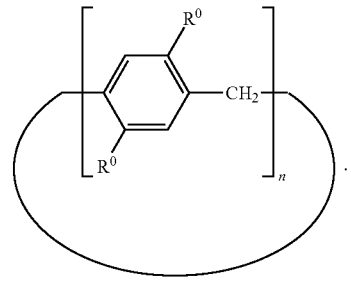

The hydroquinone subunits of the pillarenes create a symmetrical pillar-like structure defining a central cavity. Because the central cavity can capture analytes of interest for chemical sensing, the pillarenes are an emerging class of macrocycles used in host-guest chemistry.

Calixarenes are a group of heterocyclic macrocycles having from 3 to 15 aromatic components derived from compounds such as phenol, where each component is connected by a substituted or unsubstituted methylene (—$CH_2$—) bridge. One exemplary structure of a calixarene is as follows:

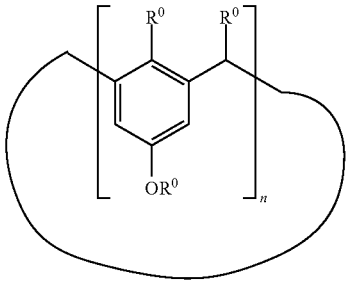

The subunits of the calixarenes can create a cup-like shape defining a central cavity. Because the central cavity can capture analytes of interest for chemical sensing, the calixarenes are an emerging class of macrocycles used in host-guest chemistry.

Cyclodextrins are a group of cyclic oligosaccharides having from 5 to 10 glucose subunits linked by 1,4 glycosidic bonds, including the $\alpha$-, $\beta$- and $\gamma$-peralkylated cyclodextrins and derivatives thereof. The basic core structure of a peralkylated cyclodextrin is as follows:

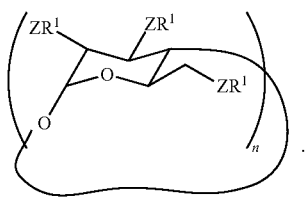

The glucose subunits of cyclodextrins can create a toroid structure having one large opening and one small opening expose to its environment. The interior cavity defined by the toroid structure of the cyclodextrins can allow the cyclodextrins to form complexes with other molecules for use in host-guest chemistry.

Without wishing to be bound by any particular theory, it is believed that host-guest chemistry describes the complex or complexes that can be formed by two or more molecules, where the two or more molecules are held together by intermolecular forces other than covalent bonds. Pillarenes, calixarenes, and cyclodextrins can be functionalized onto graphene through non-covalent π-π stacking interactions or non-covalent —CH-π stacking interactions, owing to the electron-rich aromatic rings and one or more alkyloxy groups attached to the aromatic rings.

Without wishing to be bound by any particular theory, it is believed that hydrogen atoms within hydrocarbon groups (e.g., alkyl chains) can interact with the π electron system on the surface of graphene through electrostatic interactions. Hydrogen atoms have low electronegativity, and as such, they carry a partial positive charge. The partial positive charge on the hydrogen atoms of alkyl chains can participate in electrostatic interactions with the π electron system of the π band on the surface of graphene. The alkyl chains can adsorb onto the graphene surface in an all trans conformation along the carbon-carbon backbone, such that the carbon atoms fall into one plane that is either perpendicular or parallel to the graphene surface.

By way of example, the trans conformation of an alkyl chain having a perpendicular orientation of its carbon-carbon backbone along the surface of graphene creates a configuration where every second —CH$_2$— group of the alkyl chain has its hydrogen atoms pointing towards the graphene. As such, alkyl chains can orient themselves with respect to the graphene surface so that the —CH$_2$— hydrogens of alternate —CH$_2$— groups are disposed the same distance from the graphene surface and the hydrogen-graphene interactions are maximized. Thus, the alkyl chain can interact with the surface of graphene along the length of the alkyl chain. It is also believed that the hydrogen atoms of alkenyl chains and alkynyl chains, and derivatives thereof, can similarly interact with the graphene surface.

The non-covalent functionalization of graphene with a self-assembled monolayer of receptor molecules, including pillarenes, calixarenes, or peralkylated cyclodextrins substituted with, for example, hydrocarbon groups, does not significantly affect the atomic structure of graphene, and provides a stable graphene-based sensor with high sensitivity towards a number of volatile organic compounds (VOCs) in the parts-per-billion (ppb) or parts-per-million (ppm) levels. As such, the embodiments herein can be used to detect VOCs and/or differential binding patterns of the same that, in turn, can be used to identify disease states.

Referring now to FIG. 1, a schematic view of a graphene-based variable capacitor (or graphene varactor) 100 is shown in accordance with the embodiments herein. It will be appreciated that graphene varactors can be prepared in various ways with various geometries, and that the graphene varactor shown in FIG. 1 is just one example in accordance with the embodiments herein.

Graphene varactor 100 can include an insulator layer 102, a gate electrode 104 (or "gate contact"), a dielectric layer (not shown in FIG. 1), one or more graphene layers, such as graphene layers 108a and 108b, and a contact electrode 110 (or "graphene contact"). In some embodiments, the graphene layer(s) 108a-b can be contiguous, while in other embodiments the graphene layer(s) 108a-b can be non-contiguous. Gate electrode 104 can be deposited within one or more depressions formed in insulator layer 102. Insulator layer 102 can be formed from an insulative material such as silicon dioxide, formed on a silicon substrate (wafer), and the like. Gate electrode 104 can be formed by an electrically conductive material such as chromium, copper, gold, silver, nickel, tungsten, aluminum, titanium, palladium, platinum, iridium, and any combinations or alloys thereof, which can be deposited on top of or embedded within the insulator layer 102. The dielectric layer can be disposed on a surface of the insulator layer 102 and the gate electrode 104. The graphene layer(s) 108a-b can be disposed on the dielectric layer. The dielectric layer will be discussed in more detail below in reference to FIG. 2.

Graphene varactor 100 includes eight gate electrode fingers 106a-106h. It will be appreciated that while graphene varactor 100 shows eight gate electrode fingers 106a-106h, any number of gate electrode finger configurations can be contemplated. In some embodiments, an individual graphene varactor can include fewer than eight gate electrode fingers. In some embodiments, an individual graphene varactor can include more than eight gate electrode fingers. In other embodiments, an individual graphene varactor can include two gate electrode fingers. In some embodiments, an individual graphene varactor can include 1, 2, 3, 4, 5, 6, 7, 8, 9, 10, or more gate electrode fingers.

Graphene varactor 100 can include one or more contact electrodes 110 disposed on portions of the graphene layers 108a and 108b. Contact electrode 110 can be formed from an electrically conductive material such as chromium, copper, gold, silver, nickel, tungsten, aluminum, titanium, palladium, platinum, iridium, and any combinations or alloys thereof. Further aspects of exemplary graphene varactors can be found in U.S. Pat. No. 9,513,244, the content of which is herein incorporated by reference in its entirety. The graphene varactors described herein can include those in which a single graphene layer has been surface-modified through non-covalent interactions between graphene and molecules substituted with hydrocarbon groups. In some embodiments, the surface of a single graphene layer can be surface-modified through non-covalent electrostatic interactions between graphene and any one of a number of pillarenes, substituted pillarenes, or derivatives thereof. In some embodiments, the surface of a single graphene layer can be surface-modified through non-covalent electrostatic interactions between graphene and any one of a number of calixarenes, substituted calixarenes, or derivatives thereof. In some embodiments, the surface of a single graphene layer can be surface-modified through non-covalent electrostatic interactions between graphene and any one of a number of peralkylated cyclodextrins or substituted peralkylated cyclodextrins, or derivatives thereof. In other embodiments, the surface of a single graphene layer can be surface-modified through non-covalent π-π stacking interactions between graphene and any one of a number of pillarenes, substituted pillarenes, calixarenes, substituted calixarenes, peralkylated cyclodextrins, substituted peralkylated cyclodextrins, pyrenes, or substituted pyrenes, or derivatives thereof. Details regarding the graphene varactors, pillarenes, substituted pillarenes, calixarenes, substituted calixarenes, peralkylated cyclodextrins, substituted peralkylated cyclodextrins, pyrenes, or substituted pyrenes suitable for use herein will be discussed more fully below.

It will be appreciated that in various embodiments herein, graphene can be substituted with other similar single-layer structural materials, including for example, borophene or other structural analogues of graphene. Borophene is a single layer of boron atoms arranged in various crystalline configurations.

Figure 2:
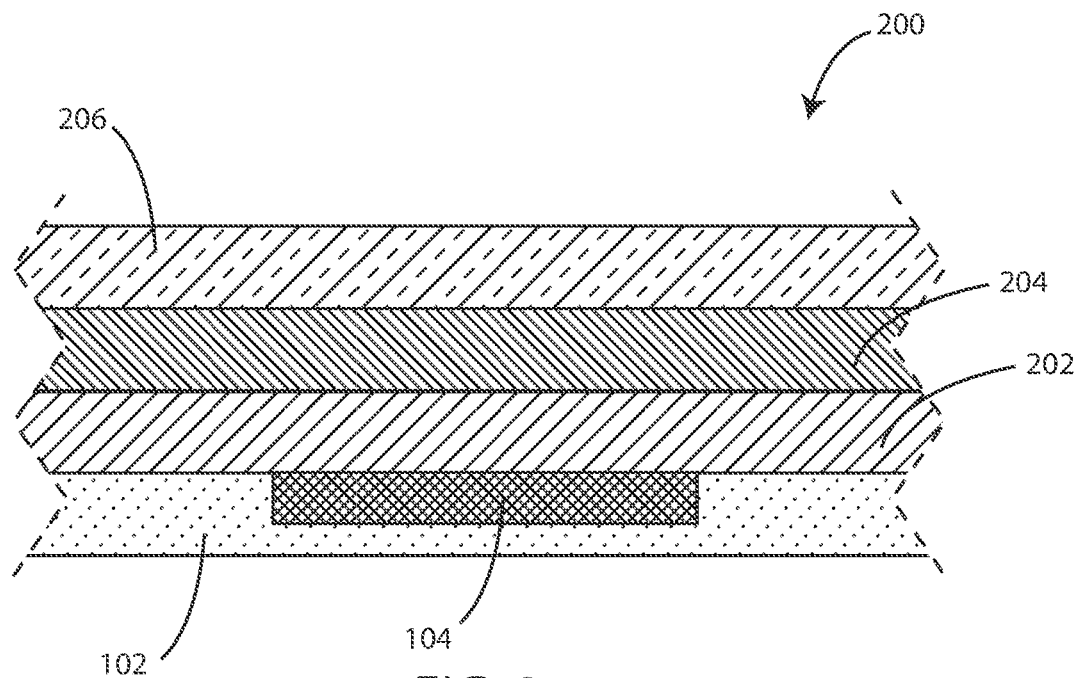
FIG. 2 is a schematic cross-sectional view of a portion of a graphene varactor in accordance with various embodiments herein.

Referring now to FIG. 2, a schematic cross-sectional view of a portion of a graphene varactor 200 is shown in accordance with various embodiments herein. The graphene varactor 200 can include an insulator layer 102 and a gate electrode 104 recessed into the insulator layer 102. The gate electrode 104 can be formed by depositing an electrically conductive material in the depression in the insulator layer 102, as discussed above in reference to FIG. 1. A dielectric layer 202 can be formed on a surface of the insulator layer 102 and the gate electrode 104. In some examples, the dielectric layer 202 can be formed of a material, such as, silicon dioxide, aluminum oxide, hafnium dioxide, zirconium dioxide, hafnium silicate, or zirconium silicate.

The graphene varactor 200 can include a single graphene layer 204 that can be disposed on a surface of the dielectric layer 202. The graphene layer 204 can be surface-modified with a self-assembled monolayer 206. The self-assembled monolayer 206 can be formed of a homogenous population of pillarenes, substituted pillarenes, or derivatives thereof disposed on an outer surface of the graphene layer 204 through non-covalent interactions. In some embodiments, the self-assembled monolayer 206 can be formed of a homogenous population of calixarenes, substituted calixarenes, or derivatives thereof. In other embodiments, the self-assembled monolayer 206 can be formed of a homogenous population of peralkylated cyclodextrins, substituted peralkylated cyclodextrins, or derivatives thereof. Exemplary pillarenes, substituted pillarenes, calixarenes, substituted calixarenes, peralkylated cyclodextrins, substituted peralkylated cyclodextrins, pyrenes, or substituted pyrenes, or derivatives of any of the foregoing, are described more fully below. The self-assembled monolayer 206 can provide at least 90% surface coverage (by area) of the graphene layer 204. In some embodiments, the self-assembled monolayer 206 can provide at least 95% surface coverage of the graphene layer 204. In other embodiments, the self-assembled monolayer 206 can provide at least 98% surface coverage of the graphene layer 204.

In some embodiments, the self-assembled monolayer can provide at least 50%, 60%, 70%, 80%, 81%, 82%, 83%, 84%, 85%, 86%, 87%, 88%, 89%, 90%, 91% 92%, 93%, 94%, 95%, 96%, 97%, 98%, 99% or 100% surface coverage (by area) of the graphene layer. It will be appreciated that the self-assembled monolayer can provide surface coverage falling within a range wherein any of the forgoing percentages can serve as the lower or upper bound of the range, provided that the lower bound of the range is a value less than the upper bound of the range.

In some embodiments, it will be appreciated that the self-assembly of pillarenes, substituted pillarenes, calixarenes, substituted calixarenes, peralkylated cyclodextrins, substituted peralkylated cyclodextrins, pyrenes, or substituted pyrenes, or derivatives thereof, on the surface of the graphene layer can include the self-assembly into more than a monolayer, such as a multilayer. Multilayers can be detected and quantified by techniques such as scanning tunneling microscopy (STM) and other scanning probe microscopies. References herein to a percentage of coverage greater than 100% shall refer to the circumstance where a portion of the surface area is covered by more than a monolayer, such as covered by two, three or potentially more layers of the compound used. Thus, a reference to 105% coverage herein shall indicate that approximately 5% of the surface area includes more than monolayer coverage over the graphene layer. In some embodiments, graphene surfaces can include 101%, 102%, 103%, 104%, 105%, 110%, 120%, 130%, 140%, 150%, or 175% surface coverage of the graphene layer. It will be appreciated that multilayer surface coverage of the graphene layer can fall within a range of surface coverages, wherein any of the forgoing percentages can serve as the lower or upper bound of the range, provided that the lower bound of the range is a value less than the upper bound of the range. For example, ranges of coverage can include, but are not limited to, 50% to 150% by surface area, 80% to 120% by surface area, 90% to 110%, or 99% to 120% by surface area.

In some embodiments, the self-assembled monolayers suitable for use herein can provide coverage of the graphene surface with a monolayer as quantified by the Langmuir theta value of at least some minimum threshold value, but avoid covering the majority of the surface of the graphene with a multilayer thicker than a monolayer. Details about the Langmuir theta values and determination of thereof for a particular self-assembled monolayer using Langmuir adsorption theory is described more fully below. In some embodiments, the self-assembled monolayers suitable for use herein provide a Langmuir theta value of at least 0.95. In some embodiments, the self-assembled monolayers suitable for use herein provide a Langmuir theta value of at least 0.98. In some embodiments, the self-assembled monolayers can provide a Langmuir theta value of at least 0.85, 0.86, 0.87, 0.88, 0.89, 0.90, 0.91, 0.92, 0.93, 0.94, 0.95, 0.96, 0.97, 0.98, 0.99, or 1.0. It will be appreciated that the self-assembled monolayer can provide a range of Langmuir theta values, wherein any of the forgoing Langmuir theta values can serve as the lower or upper bound of the range, provided that the lower bound of the range is a value less than the upper bound of the range.

Figure 3:
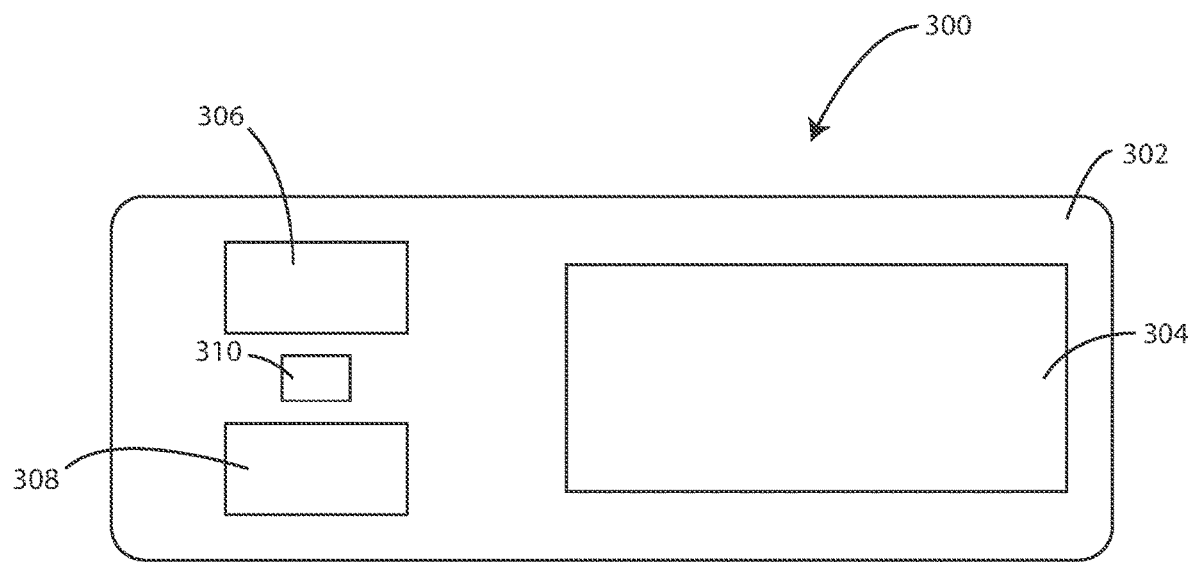
FIG. 3 is a schematic top plan view of a chemical sensor element in accordance with various embodiments herein.

Referring now to FIG. 3, a schematic top plan view of a chemical sensor element 300 is shown in accordance with various embodiments herein. The chemical sensor element 300 can include a substrate 302. It will be appreciated that the substrate can be formed from many different materials. By way of example, the substrate can be formed from silicon, glass, quartz, sapphire, polymers, metals, glasses, ceramics, cellulosic materials, composites, metal oxides, and the like. The thickness of the substrate can vary. In some embodiments, the substrate has sufficient structural integrity to be handled without undue flexure that could damage components thereon. In some embodiments, the substrate can have a thickness of about 0.05 mm to about 5 mm. The length and width of the substrate can also vary. In some embodiments, the length (or major axis) can be from about 0.2 cm to about 10 cm. In some embodiments, the length (or major axis) can be from about 20 µm to about 1 cm. In some embodiments, the width (perpendicular to the major axis) can be from about 0.2 cm to about 8 cm. In some embodiments, the width (perpendicular to the major axis) can be from about 20 µm to about 0.8 cm. In some embodiments, the graphene-based chemical sensor can be disposable.

A first measurement zone 304 can be disposed on the substrate 302. In some embodiments, the first measurement zone 304 can define a portion of a first gas flow path. The first measurement zone (or gas sample zone) 304 can include a plurality of discrete graphene-based variable capacitors (or graphene varactors) that can sense analytes in a gaseous sample, such as a breath sample. A second measurement zone (or environment sample zone) 306, separate from the first measurement zone 304, can also be disposed on the substrate 302. The second measurement zone 306 can also include a plurality of discrete graphene varactors. In some embodiments, the second measurement zone 306 can include the same (in type and/or number) discrete graphene varactors that are within the first measurement zone 304. In some embodiments, the second measurement zone 306 can include only a subset of the discrete graphene varactors that are within the first measurement zone 304. In operation, the data gathered from the first measurement zone, which can be reflective of the gaseous sample analyzed, can be corrected or normalized based on the data gathered from the second measurement zone, which can be reflective of analytes present in the environment.

In some embodiments, a third measurement zone (drift control or witness zone) 308 can also be disposed on the substrate. The third measurement zone 308 can include a plurality of discrete graphene varactors. In some embodiments, the third measurement zone 308 can include the same (in type and/or number) discrete graphene varactors that are within the first measurement zone 304. In some embodiments, the third measurement zone 308 can include only a subset of the discrete graphene varactors that are within the first measurement zone 304. In some embodiments, the third measurement zone 308 can include discrete graphene varactors that are different than those of the first measurement zone 304 and the second measurement zone 306. Aspects of the third measurement zone are described in greater detail below.

The first measurement zone, the second measurement zone, and the third measurement zone can be the same size or can be of different sizes. The chemical sensor element 300 can also include a component 310 to store reference data. The component 310 to store reference data can be an electronic data storage device, an optical data storage device, a printed data storage device (such as a printed code), or the like. The reference data can include, but is not limited to, data regarding the third measurement zone (described in greater detail below).

In some embodiments, chemical sensor elements embodied herein can include electrical contacts (not shown) that can be used to provide power to components on the chemical sensor element 300 and/or can be used to read data regarding the measurement zones and/or data from the stored in component 310. However, in other embodiments there are no external electrical contacts on the chemical sensor element 300.

It will be appreciated that many different circuit designs can be used to gather data and/or signals from chemical sensor elements herein including both direct-contact circuit designs as well as passive wireless sensing circuit designs. Some exemplary measurement circuits are described in U.S. Publ. Appl. No. 2019/0025237, the content of which is herein incorporated by reference.

Figure 5:
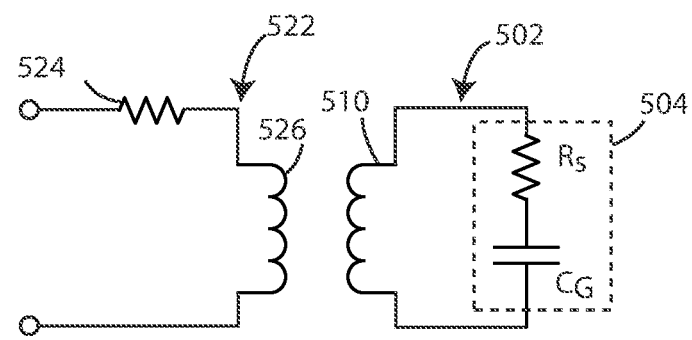
FIG. 5 is a circuit diagram of a passive sensor circuit and a portion of a reading circuit in accordance with various embodiments herein.

It will be appreciated that the chemical sensor elements embodied herein can include those that are compatible with passive wireless sensing. A schematic diagram of a passive sensor circuit 502 and a portion of a reading circuit 522 is shown in FIG. 5 and discussed in more detail below. In the passive wireless sensing arrangement, the graphene varactor(s) can be integrated with an inductor such that one terminal of the graphene varactor contacts one end of the inductor, and a second terminal of the graphene varactor contacts a second terminal of the inductor. In some embodiments, the inductor can be located on the same substrate as the graphene varactor, while in other embodiments, the inductor could be located in an off-chip location.

Figure 4:
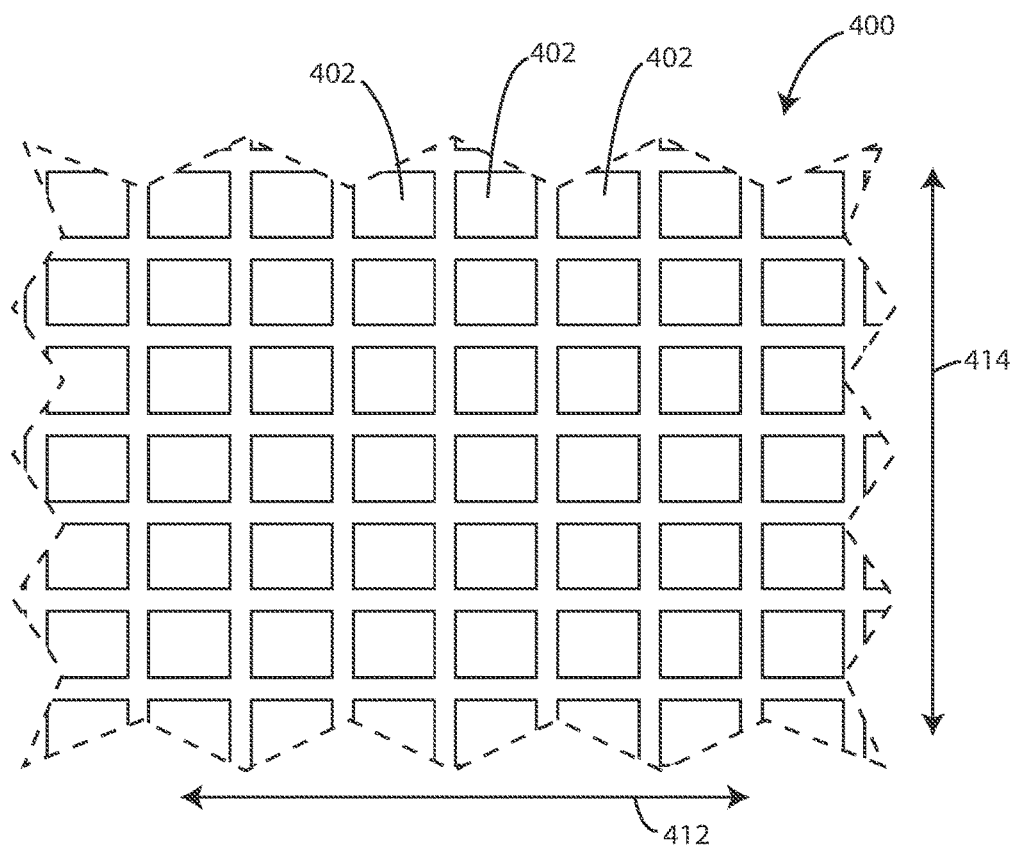
FIG. 4 is a schematic diagram of a portion of a measurement zone in accordance with various embodiments herein.

Referring now to FIG. 4, a schematic diagram of a portion of a measurement zone 400 is shown in accordance with various embodiments herein. A plurality of discrete graphene varactors 402 can be disposed within the measurement zone 400 in an array. In some embodiments, a chemical sensor element can include a plurality of graphene varactors configured in an array within a measurement zone. In some embodiments, the plurality of graphene varactors can be identical, while in other embodiments the plurality of graphene varactors can be different from one another.

In some embodiments, the discrete graphene varactors can be heterogeneous in that they are all different from one another in terms of their binding behavior specificity with regard to a particular analyte. In some embodiments, some discrete graphene varactors can be duplicated for validation purposes, but are otherwise heterogeneous from other discrete graphene varactors. Yet in other embodiments, the discrete graphene varactors can be homogeneous. While the discrete graphene varactors 402 of FIG. 4 are shown as boxes organized into a grid, it will be appreciated that the discrete graphene varactors can take on many different shapes (including, but not limited to, various polygons, circles, ovals, irregular shapes, and the like) and, in turn, the groups of discrete graphene varactors can be arranged into many different patterns (including, but not limited to, star patterns, zig-zag patterns, radial patterns, symbolic patterns, and the like).

In some embodiments, the order of specific discrete graphene varactors 402 across the length 412 and width 414 of the measurement zone can be substantially random. In other embodiments, the order can be specific. For example, in some embodiments, a measurement zone can be ordered so that the specific discrete graphene varactors 402 for analytes having a lower molecular weight are located farther away from the incoming gas flow relative to specific discrete graphene varactors 402 for analytes having a higher molecular weight which are located closer to the incoming gas flow. As such, chromatographic effects which may serve to provide separation between chemical compounds of different molecular weight can be taken advantage of to provide for optimal binding of chemical compounds to corresponding discrete graphene varactors.

The number of discrete graphene varactors within a particular measurement zone can be from about 1 to about 100,000. In some embodiments, the number of discrete graphene varactors can be from about 1 to about 10,000. In some embodiments, the number of discrete graphene varactors can be from about 1 to about 1,000. In some embodiments, the number of discrete graphene varactors can be from about 2 to about 500. In some embodiments, the number of discrete graphene varactors can be from about 10 to about 500. In some embodiments, the number of discrete graphene varactors can be from about 50 to about 500. In some embodiments, the number of discrete graphene varactors can be from about 1 to about 250. In some embodiments, the number of discrete graphene varactors can be from about 1 to about 50.

Each of the discrete graphene varactors suitable for use herein can include at least a portion of one or more electrical circuits. By way of example, in some embodiments, each of the discrete graphene varactors can include one or more passive electrical circuits. In some embodiments, the graphene varactors can be included such that they are integrated directly on an electronic circuit. In some embodiments, the graphene varactors can be included such that they are wafer bonded to the circuit. In some embodiments, the graphene varactors can include integrated readout electronics, such as a readout integrated circuit (ROIC). The electrical properties of the electrical circuit, including resistance or capacitance, can change upon binding, such as specific and/or non-specific binding, with a component from a gas sample.

Referring now to FIG. 5, a schematic diagram of a passive sensor circuit 502 and a portion of a reading circuit 522 is shown in accordance with various aspects herein. In some embodiments, the passive sensor circuit 502 can include a metal-oxide-graphene varactor 504 (wherein RS represents the series resistance and CG represents the varactor capacitor) coupled to an inductor 510. Graphene varactors can be prepared in various ways and with various geometries. By way of example, in some aspects, a gate electrode can be recessed into an insulator layer as shown as gate electrode 104 in FIG. 1. A gate electrode can be formed by etching a depression into the insulator layer and then depositing an electrically conductive material in the depression to form the gate electrode. A dielectric layer can be formed on a surface of the insulator layer and the gate electrode. In some examples, the dielectric layer can be formed of a metal oxide such as, aluminum oxide, hafnium dioxide, zirconium dioxide, silicon dioxide, or of another material such as hafnium silicate or zirconium silicate. A surface-modified graphene layer can be disposed on the dielectric layer. Contact electrodes can also be disposed on a surface of the surface-modified graphene layer, also shown in FIG. 1 as contact electrode 110.

Further aspects of exemplary graphene varactor construction can be found in U.S. Pat. No. 9,513,244, the content of which is herein incorporated by reference in its entirety.

In various embodiments, the functionalized graphene layer (e.g., functionalized to include analyte binding receptors), which is part of the graphene varactor and thus part of a sensor circuit, such as a passive sensor circuit, is exposed to the gas sample flowing over the surface of the measurement zone. The passive sensor circuit 502 can also include an inductor 510. In some embodiments, only a single varactor is included with each passive sensor circuit 502. In other embodiments, multiple varactors are included, such as in parallel, with each passive sensor circuit 502.

In the passive sensor circuit 502, the capacitance of the electrical circuit changes upon binding of an analyte in the gas sample and the graphene varactor. The passive sensor circuit 502 can function as an LRC resonator circuit, wherein the resonant frequency of the LRC resonator circuit changes upon binding with a component from a gas sample.

The reading circuit 522 can be used to detect the electrical properties of the passive sensor circuit 502. By way of example, the reading circuit 522 can be used to detect the resonant frequency of the LRC resonator circuit and/or changes in the same. In some embodiments, the reading circuit 522 can include a reading coil having a resistance 524 and an inductance 526. When the sensor-side LRC circuit is at its resonant frequency, a plot of the phase of the impedance of the reading circuit versus the frequency has a minimum (or phase dip frequency). Sensing can occur when the varactor capacitance varies in response to binding of analytes, which changes the resonant frequency, and/or the value of the phase dip frequency.

Figure 6:
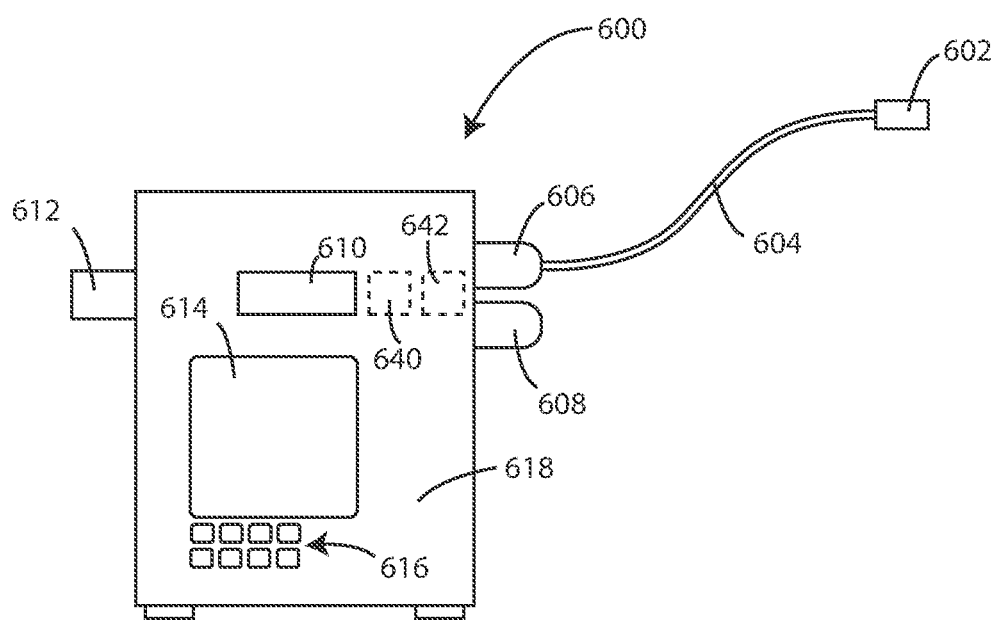
FIG. 6 is a schematic view of a system for sensing gaseous analytes in accordance with various embodiments herein.

Referring now to FIG. 6, a schematic view of a system 600 for sensing gaseous analytes in accordance with various embodiments herein is shown. The system 600 can include a housing 618. The system 600 can include a mouthpiece 602 into which a subject to be evaluated can blow a breath sample. The gaseous breath sample can pass through an inflow conduit 604 and pass through an evaluation sample (patient sample) input port 606. The system 600 can also include a control sample (environment) input port 608. The system 600 can also include a sensor element chamber 610, into which disposable sensor elements can be placed. The system 600 can also include a display screen 614 and a user input device 616, such as a keyboard. The system can also include a gas outflow port 612. The system 600 can also include flow sensors in fluid communication with the gas flow associated with one or more of the evaluation sample input port 606 and control sample input port 608. It will be appreciated that many different types of flow sensors can be used. In some embodiments, a hot-wire anemometer can be used to measure the flow of air. In some embodiments, the system can include a $CO_2$ sensor in fluid communication with the gas flow associated with one or more of the evaluation sample input port 606 and control sample input port 608.

In various embodiments, the system 600 can also include other functional components. By way of example, the system 600 can include a humidity control module 640 and/or a temperature control module 642. The humidity control module can be in fluid communication with the gas flow associated with one or more of the evaluation sample input port 606 and control sample input port 608 in order to adjust the humidity of one or both gas flow streams in order to make the relative humidity of the two streams substantially the same in order to prevent an adverse impact on the readings obtained by the system. The temperature control module can be in fluid communication with the gas flow associated with one or more of the evaluation sample input port 606 and control sample input port 608 in order to adjust the temperature of one or both gas flow streams in order to make the temperature of the two streams substantially the same in order to prevent an adverse impact on the readings obtained by the system. By way of example, the air flowing into the control sample input port can be brought up to 37 degrees Celsius or higher in order to match or exceed the temperature of air coming from a patient. The humidity control module and the temperature control module can be upstream from the input ports, within the input ports, or downstream from the input ports in the housing 618 of the system 600. In some embodiments, the humidity control module 640 and the temperature control module 642 can be integrated.

In some embodiments (not shown), the control sample input port 608 of system 600 can also be connected to a mouthpiece 602. In some embodiments, the mouthpiece 602 can include a switching airflow valve such that when the patient is drawing in breath, air flows from the control sample input port 608 to the mouthpiece, and the system is configured so that this causes ambient air to flow across the appropriate control measurement zone (such as the second measurement zone). Then when the patient exhales, the switching airflow valve can switch so that a breath sample from the patient flows from the mouthpiece 602 through the inflow conduit 604 and into the evaluation sample input port 606 and across the appropriate sample (patient sample) measurement zone (such as the first measurement zone) on the disposable sensor element.

In an embodiment, a method of making a chemical sensor element is included. The method can include depositing one or more measurement zones onto a substrate. The method can further include depositing a plurality of discrete graphene varactors within the measurement zones on the substrate. The method can include generating one or more discrete graphene varactors by modifying a surface of a graphene layer with pillarenes, substituted pillarenes, calixarenes, substituted calixarenes, peralkylated cyclodextrins, substituted peralkylated cyclodextrins, pyrenes, or substituted pyrenes, or derivatives thereof to form a self-assembled monolayer on an outer surface of the graphene layer through non-covalent interactions. The method can include quantifying the extent of surface coverage of the self-assembled monolayer using contact angle goniometry, Raman spectroscopy, or X-Ray photoelectron spectroscopy. The method can include selecting derivatized graphene layers that exhibit a Langmuir theta value of at least 0.9, as will be discussed more fully below. In some embodiments, the method can include selecting derivatized graphene layers that exhibit a Langmuir theta value of at least 0.98. The method can further include depositing a component to store reference data onto the substrate. In some embodiments, the measurement zones can all be placed on the same side of the substrate. In other embodiments, the measurement zones can be placed onto different sides of the substrate.

In an embodiment, a method of assaying one or more gas samples is included. The method can include inserting a chemical sensor element into a sensing machine. The chemical sensor element can include a substrate and a first measurement zone comprising a plurality of discrete graphene varactors. The first measurement zone can define a portion of a first gas flow path. The chemical sensor element can further include a second measurement zone separate from the first measurement zone. The second measurement zone can also include a plurality of discrete graphene varactors. The second measurement zone can be disposed outside of the first gas flow path.

The method can further include prompting a subject to blow air into the sensing machine to follow the first gas flow path. In some embodiments, the $CO_2$ content of the air from the subject is monitored and sampling with the disposable sensor element is conducted during the plateau of $CO_2$ content, as it is believed that the air originating from the alveoli of the patient has the richest content of chemical compounds for analysis, such as volatile organic compounds. In some embodiments, the method can include monitoring the total mass flow of the breath sample and the control (or environmental) air sample using flow sensors. The method can further include interrogating the discrete graphene varactors to determine their analyte binding status. The method can further include discarding the disposable sensor element upon completion of sampling.

Figure 7:
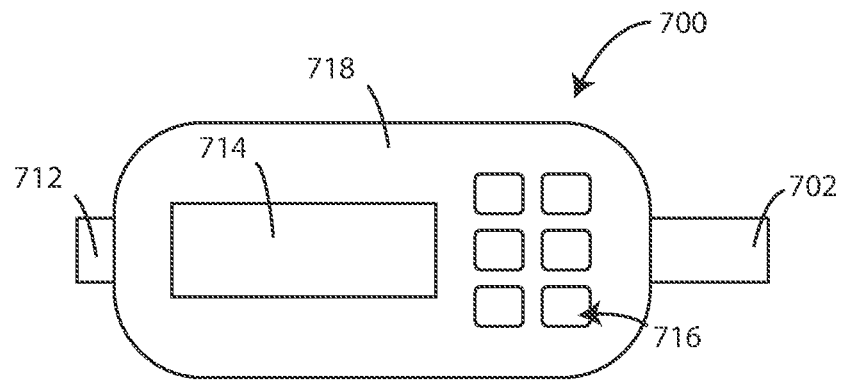
FIG. 7 is a schematic view of a system for sensing gaseous analytes in accordance with various embodiments herein.

Referring now to FIG. 7, a schematic view of a system 700 for sensing gaseous analytes in accordance with various embodiments herein is shown. In this embodiment, the system is in a hand-held format. The system 700 can include a housing 718. The system 700 can include a mouthpiece 702 into which a subject to be evaluated can blow a breath sample. The system 700 can also include a display screen 714 and a user input device 716, such as a keyboard. The system can also include a gas outflow port 712. The system can also include various other components such as those described with reference to FIG. 6 above.

In some embodiments, one of the measurement zones can be configured to indicate changes (or drift) in the chemical sensor element that could occur as a result of aging and exposure to varying conditions (such as heat exposure, light exposure, molecular oxygen exposure, humidity exposure, etc.) during storage and handling prior to use. In some embodiments, the third measurement zone can be configured for this purpose.

Figure 8:
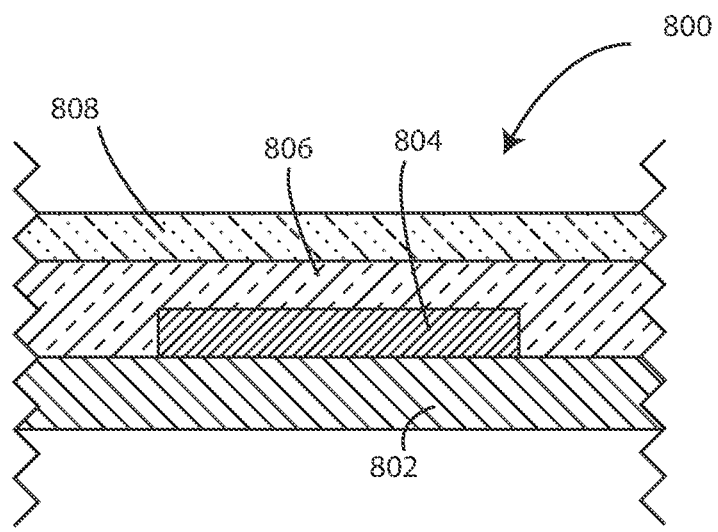
FIG. 8 is a schematic cross-sectional view of a portion of a chemical sensor element in accordance with various embodiments herein.

Referring now to FIG. 8, a schematic cross-sectional view is shown of a portion of a chemical sensor element 800 in accordance with various embodiments herein. The chemical sensor element 800 can include a substrate 802 and a discrete graphene varactor 804 disposed thereon that is part of a measurement zone. Optionally, in some embodiments the discrete graphene varactor 804 can be encapsulated by an inert material 806, such as nitrogen gas, or an inert liquid or solid. In this manner, the discrete graphene varactor 804 for the third measurement zone can be shielded from contact with gas samples and can therefore be used as a control or reference to specifically control for sensor drift which may occur between the time of manufacturing and the time of use of the disposable sensor element. In some embodiments, such as in the case of the use of an inert gas or liquid, the discrete binding detector can also include a barrier layer 808, which can be a layer of a polymeric material, a foil, or the like. In some cases, the barrier layer 808 can be removed just prior to use.

In an embodiment, a method for detecting one or more analytes is included. The method can include collecting a gaseous sample. In some embodiments, the gaseous sample is from a patient. In some embodiments the gaseous sample can include exhaled breath. In other embodiments, the gaseous sample can include breath removed from the lungs of a patient via a catheter or other similar extraction device. In some embodiments, the extraction device can include an endoscope, a bronchoscope, or tracheoscope. The method can also include contacting a graphene varactor with the gaseous sample, where the graphene varactor includes a graphene layer and a self-assembled monolayer disposed on an outer surface of the graphene layer through non-covalent interactions. In some embodiments, the self-assembled monolayer can provide a Langmuir theta value of at least 0.9. In some embodiments, the method can include selecting derivatized graphene layers that exhibit a Langmuir theta value of at least 0.98. Langmuir theta values will be discussed more fully below. In some embodiments, the method can include measuring a differential response in a capacitance of the graphene reactor due to the binding of one or more analytes present in the gaseous sample, which in turn can be used to identify disease states. In some embodiments, the method can include a self-assembled monolayer selected from at least one pillarenes, substituted pillarenes, calixarenes, substituted calixarenes, peralkylated cyclodextrins, substituted peralkylated cyclodextrins, pyrenes, or substituted pyrenes, or derivatives thereof.

Graphene Varactors

The graphene varactors described herein can be used to sense one or more analytes in a gaseous sample, such as, for example, the breath of a patient. Graphene varactors embodied herein can exhibit a high sensitivity for volatile organic compounds (VOCs) found in gaseous samples at or near parts-per-million (ppm) or parts-per-billion (ppb) levels. The adsorption of VOCs onto the surface of graphene varactors can change the resistance, capacitance, or quantum capacitance of such devices, and can be used to detect the VOCs and/or patterns of binding by the same that, in turn, can be used to identify disease states such as cancer, cardiac diseases, infections, multiple sclerosis, Alzheimer's disease, Parkinson's disease, and the like. The graphene varactors can be used to detect individual analytes in gas mixtures, as well as patterns of responses in highly complex mixtures. In some embodiments, one or more graphene varactors can be included to detect the same analyte in a gaseous sample. In some embodiments, one or more graphene varactors can be included to detect different analytes in a gaseous sample. In some embodiments, one or more graphene varactors can be included to detect a multitude of analytes in a gaseous sample.

An exemplary graphene varactor can include a graphene layer and a self-assembled monolayer disposed on an outer surface of the graphene layer, interacting with the latter through non-covalent interactions, as shown and discussed above in reference to FIG. 2. The self-assembled monolayers suitable for use herein can provide a Langmuir theta value of at least 0.9. Determination of the Langmuir theta value for a particular self-assembled monolayer using Langmuir adsorption theory is described more fully below. In some embodiments, the self-assembled monolayers suitable for use herein provide a Langmuir theta value of at least 0.95. In some embodiments, the self-assembled monolayers suitable for use herein provide a Langmuir theta value of at least 0.98.

The graphene varactors described herein can include those in which a single graphene layer has been surface-modified through non-covalent interactions with one or more receptor molecules including pillarenes, substituted pillarenes, calixarenes, substituted calixarenes, peralkylated cyclodextrins, substituted peralkylated cyclodextrins, pyrenes, or substituted pyrenes, or derivatives thereof, as described elsewhere herein. Substituted pillarenes, substituted calixarenes, substituted peralkylated cyclodextrins, or substituted pyrenes can be substituted with any number of functional groups described herein, including, but not limited to alkyl groups, alkenyl groups, alkynyl groups, heteroalkyl groups, heteroalkenyl groups, heteroalkynyl groups, haloalkyl groups, haloalkenyl groups, haloalkynyl groups, halogenated heteroalkyl groups, halogenated heteroalkenyl groups, halogenated heteroalkynyl groups, aryl groups, substituted aryl groups, heteroaryl groups, substituted heteroaryl groups, aryloxy groups, substituted aryloxy groups, arylthio, substituted arylthio groups, aryl amine groups, substituted aryl amine groups, halogenated aryl groups, substituted halogenated aryl groups, biphenyl groups, and/or substituted biphenyl groups.

As used herein, the term "alkyl" refers to any linear, branched, or cyclic hydrocarbon functional group containing anywhere from 1 to 20 carbon atoms (i.e., $C_1$-$C_{20}$ alkyl). In some embodiments, the alkyl groups herein can contain any linear, branched, or cyclic hydrocarbon functional group containing anywhere from 6 to 18 carbon atoms (i.e., $C_6$-$C_{18}$ alkyl). In other embodiments, the alkyl groups herein can contain any linear, branched, or cyclic hydrocarbon functional group containing anywhere from 10 to 16 carbon atoms (i.e., $C_{10}$-$C_{16}$ alkyl). The alkyl groups described herein have the general formula $C_nH_{2n+1}$, unless otherwise indicated.

As used herein, the term "alkenyl" refers to any linear, branched, or cyclic hydrocarbon functional group containing anywhere from 1 to 20 carbon atoms, wherein the alkenyl group contains at least one carbon-carbon double bond (i.e., $C_1$-$C_{20}$ alkenyl). In some embodiments, the alkenyl groups herein can contain any linear, branched, or cyclic hydrocarbon functional group containing anywhere from 6 to 18 carbon atoms, wherein the alkenyl group contains at least one carbon-carbon double bond (i.e., $C_6$-$C_{18}$ alkenyl). In other embodiments, the alkenyl groups herein can contain any linear, branched, or cyclic hydrocarbon functional group containing anywhere from 10 to 16 carbon atoms, wherein the alkenyl group contains at least one carbon-carbon double bond (i.e., $C_{10}$-$C_{16}$ alkenyl). The alkenyl groups described herein have the general formula $C_nH_{(2n+1-2x)}$, where x is the number of double bonds present in the alkenyl group, unless otherwise indicated.

As used herein, the term "alkynyl" refers to any linear, branched, or cyclic hydrocarbon functional group containing anywhere from 1 to 20 carbon atoms, including one or more carbon-carbon triple bonds (i.e., $C_1$-$C_{20}$ alkynyl). In some embodiments, the alkynyl groups herein can contain any linear, branched, or cyclic hydrocarbon functional group containing anywhere from 6 to 18 carbon atoms, including one or more carbon-carbon triple bonds (i.e., $C_6$-$C_{18}$ alkynyl). In other embodiments, the alkynyl groups herein can contain any linear, branched, or cyclic hydrocarbon functional group containing anywhere from 10 to 16 carbon atoms, including one or more carbon-carbon triple bonds (i.e., $C_{10}$-$C_{16}$ alkynyl).

As used herein, the term "heteroalkyl" refers to any linear, branched, or cyclic hydrocarbon functional group containing anywhere from 1 to 20 carbon atoms, and one or more heteroatoms, including, but not limited to, N, O, P, S, Si, Se, and B, or any combination thereof (i.e., $C_1$-$C_{20}$ heteroalkyl). In some embodiments, the heteroalkyl groups herein can contain any linear, branched, or cyclic hydrocarbon functional group containing anywhere from 6 to 18 carbon atoms and one or more heteroatoms, including, but not limited to, N, O, P, S, Si, Se, and B, or any combination thereof (i.e., $C_6$-$C_{18}$ heteroalkyl). In other embodiments, the heteroalkyl groups herein can contain any linear, branched, or cyclic hydrocarbon functional group containing anywhere from 10 to 16 carbon atoms and one or more heteroatoms, including, but not limited to, N, O, P, S, Si, Se, and B, or any combination thereof (i.e., $C_{10}$-$C_{16}$ heteroalkyl). In some embodiments, the heteroalkyl groups herein can have the general formula —RZ, —RZR, —ZRZR, or —RZRZR, where R can include, but not be limited to, any identical or different, linear, branched, or cyclic, $C_1$-$C_{20}$ alkyl, or a combination thereof, and Z can include one or more heteroatoms including, but not limited to, N, O, P, S, Si, Se, and B, or any combination thereof.

In some embodiments, the heteroalkyl group can include, but not be limited to, alkoxy groups, alkyl amide groups, alkyl thioether groups, alkyl ester groups, alkyl sulfonate groups, alkyl phosphate groups, and the like. Examples of heteroalkyl groups suitable for use herein can include, but not be limited to, those selected from —ROH, —RC(O)OH, —RC(O)OR, —ROR, —RSR, —RCHO, —RX, —RC(O)NH$_2$, —RC(O)NR, —RNH$_3^+$, —RNH$_2$, —RNO$_2$, —RNHR, —RNRR, —RB(OH)$_2$, —RSO$_3^-$, —RPO$_4^{2-}$, or any combination thereof, where R can include, but not be limited to, any identical or different, linear, branched, or cyclic, $C_1$-$C_{20}$ alkyl, $C_1$-$C_{20}$ heteroalkyl, provided that at least one heteroatom including, but not limited to, N, O, P, S, Si, Se, and B, is present in at least one R group, or a combination thereof, and X can be a halogen including F, Cl, Br, I, or At.

As used herein, the term "heteroalkenyl" refers to any linear, branched, or cyclic hydrocarbon functional group containing anywhere from 1 to 20 carbon atoms, including one or more carbon-carbon double bonds, and one or more heteroatoms including, but not limited to, N, O, P, S, Si, Se, and B, or any combination thereof (i.e., $C_1$-$C_{20}$ heteroalkenyl). In some embodiments, the heteroalkenyl groups herein can contain any linear, branched, or cyclic hydrocarbon functional group containing anywhere from 6 to 18 carbon atoms, including one or more carbon-carbon double bonds, and one or more heteroatoms, including, but not limited to, N, O, P, S, Si, Se, and B, or any combination thereof (i.e., $C_6$-$C_{18}$ heteroalkenyl). In other embodiments, the heteroalkenyl groups herein can contain any linear, branched, or cyclic hydrocarbon functional group containing anywhere from 10 to 16 carbon atoms, including one or more carbon-carbon double bonds, and one or more heteroatoms, including, but not limited to, N, O, P, S, Si, Se, and B, or any combination thereof (i.e., $C_{10}$-$C_{16}$ heteroalkenyl). In some embodiments, the heteroalkenyl groups herein can have the general formula —RZ, —RZR, —ZRZR, or —RZRZR, where R can include, but not be limited to, any identical or different, linear, branched, or cyclic, $C_1$-$C_{20}$ alkyl or $C_1$-$C_{20}$ alkenyl, provided that at least one carbon-carbon double bond is present in at least one R group, or a combination thereof, and Z can include one or more heteroatoms including, but not limited to, N, O, P, S, Si, Se, and B, or any combination thereof.

In some embodiments, the heteroalkenyl group can include, but not be limited to, alkenoxy groups, alkenyl amines, alkenyl thioester groups, alkenyl ester groups, alkenyl sulfonate groups, alkenyl phosphate groups, and the like. Examples of heteroalkenyl groups suitable for use herein can include, but not be limited to, those selected from —ROH, —RC(O)OH, —RC(O)OR, —ROR, —RSR, —RCHO, —RX, —RC(O)NH$_2$, —RC(O)NR, —RNH$_3^+$, —RNH$_2$, —RNO$_2$, —RNHR, —RNRR, —RB(OH)$_2$, —RSO$_3^-$, —RPO$_4^{2-}$, or any combination thereof; where R can include, but not be limited to, any identical or different, linear, branched, or cyclic, $C_1$-$C_{20}$ alkyl, or $C_1$-$C_{20}$ alkenyl, provided that at least one or more carbon-carbon double bonds and one or more heteroatoms including, but not limited to, N, O, P, S, Si, Se, and B, or any combination thereof, are present in at least one R group; or a combination thereof, and X can be a halogen including F, Cl, Br, I, or At.

As used herein, the term "heteroalkynyl" refers to any linear, branched, or cyclic hydrocarbon functional group containing anywhere from 1 to 20 carbon atoms, including one or more carbon-carbon triple bonds, and one or more heteroatoms including, but not limited to, N, O, P, S, Si, Se, and B, or any combination thereof (i.e., $C_1$-$C_{20}$ heteroalkynyl). In some embodiments, the heteroalkynyl groups herein can contain any linear, branched, or cyclic hydrocarbon functional group containing anywhere from 6 to 18 carbon atoms, including one or more carbon-carbon triple bonds, and one or more heteroatoms, including, but not limited to, N, O, P, S, Si, Se, and B, or any combination thereof (i.e., $C_6$-$C_{18}$ heteroalkynyl). In other embodiments, the heteroalkynyl groups herein can contain any linear, branched, or cyclic hydrocarbon functional group containing anywhere from 10 to 16 carbon atoms, including one or more carbon-carbon triple bonds, and one or more heteroatoms, including, but not limited to, N, O, P, S, Si, Se, and B, or any combination thereof (i.e., $C_{10}$-$C_{16}$ heteroalkynyl). In some embodiments, the heteroalkynyl groups herein can have the general formula —RZ, —RZR, —ZRZR, or —RZRZR, where R can include, but not be limited to, any identical or different, linear, branched, or cyclic, $C_1$-$C_{20}$ alkyl, $C_1$-$C_{20}$ alkenyl, or $C_1$-$C_{20}$ alkynyl, provided that at least one carbon-carbon triple bond is present in at least one R group or a combination thereof, and Z can include one or more heteroatoms including, but not limited to, N, O, P, S, Si, Se, and B, or any combination thereof.

In some embodiments, the heteroalkynyl group can include, but not be limited to, alkynyloxy groups, alkynyl amines, alkynyl thioester groups, alkynyl ester groups, alkenyl sulfonate groups, alkenyl phosphate groups, and the like. Examples of heteroalkynyl groups suitable for use herein can include, but not be limited to, those selected from —ROH, —RC(O)OH, —RC(O)OR, —ROR, —RSR, —RCHO, —RX, —RC(O)NH$_2$, —RC(O)NR, —RNH$_3^*$, —RNH$_2$, —RNO$_2$, —RNHR, —RNRR, —RB(OH)$_2$, —RSO$_3$—, —RPO$_4^{2-}$, or any combination thereof; where R can include, but not be limited to, any identical or different, linear, branched, or cyclic, $C_1$-$C_{20}$ alkyl, $C_1$-$C_{20}$ alkenyl, or $C_1$-$C_{20}$ alkynyl, provided that at least one or more carbon-carbon triple bonds and one or more heteroatoms including, but not limited to, N, O, P, S, Si, Se, and B, or any combination thereof, are present in at least one R group; or a combination thereof, and X can be a halogen including F, Cl, Br, I, or At.

As used herein, the term "haloalkyl" refers to any linear, branched, or cyclic alkyl groups containing anywhere from 1 to 20 carbon atoms (i.e., $C_1$-$C_{20}$) having one or more hydrogen atoms replaced by a halogen atom including at least one of F, Cl, Br, I, At (i.e., $C_1$-$C_{20}$ haloalkyl). In some embodiments, the haloalkyl groups herein can contain any linear, branched, or cyclic alkyl group containing anywhere from 6 to 18 carbon atoms having one or more hydrogen atoms replaced by a halogen atom including at least one of F, Cl, Br, I, or At (i.e., $C_6$-$C_{18}$ haloalkyl). In other embodiments, the haloalkyl groups herein can contain any linear, branched, or cyclic alkyl group containing anywhere from 10 to 16 carbon atoms having one or more hydrogen atoms replaced by a halogen atom including at least one of F, Cl, Br, I, or At (i.e., $C_{10}$-$C_{16}$ haloalkyl). In some embodiments, the haloalkyl can include a monohaloalkyl containing only one halogen atom in place of a hydrogen atom. In other embodiments, the haloalkyl can include a polyhaloalkyl containing more than one halogen atom in place of a hydrogen atom, provided at least one hydrogen atom remains. In yet other embodiments, the haloalkyl can include a perhaloalkyl containing a halogen atom in place of every hydrogen atom of the corresponding alkyl.

As used herein, the term "haloalkenyl" refers to any linear, branched, or cyclic alkenyl group containing anywhere from 1 to 20 carbon atoms (i.e., $C_1$-$C_2$) having one or more hydrogen atoms replaced by a halogen atom including at least one of F, Cl, Br, I, or At, and wherein the haloalkenyl group contains at least one carbon-carbon double bond (i.e., $C_1$-$C_{20}$ haloalkenyl). In some embodiments, the haloalkenyl groups herein can contain any linear, branched, or cyclic alkenyl group containing anywhere from 6 to 18 carbon atoms, having one or more hydrogen atoms replaced by a halogen atom including at least one of F, Cl, Br, I, or At, and wherein the haloalkenyl group contains at least one carbon-carbon double bond (i.e., $C_6$-$C_{18}$ haloalkenyl). In other embodiments, the haloalkenyl groups herein can contain any linear, branched, or cyclic alkenyl group containing anywhere from 10 to 16 carbon atoms, having one or more hydrogen atoms replaced by a halogen atom including at least one of F, Cl, Br, I, or At, and wherein the haloalkenyl group contains at least one carbon-carbon double bond (i.e., $C_{10}$-$C_{16}$ haloalkenyl).

As used herein, the term "haloalkynyl" refers to any linear, branched, or cyclic alkynyl group containing anywhere from 1 to 20 carbon atoms (i.e., $C_1$-$C_2$) having one or more hydrogen atoms replaced by a halogen atom including at least one of F, Cl, Br, I, or At, and wherein the haloalkynyl group contains at least one carbon-carbon triple bond (i.e., $C_1$-$C_{20}$ haloalkynyl). In some embodiments, the haloalkynyl groups herein can contain any linear, branched, or cyclic alkynyl group containing anywhere from 6 to 18 carbon atoms, having one or more hydrogen atoms replaced by a halogen atom including at least one of F, Cl, Br, I, or At, and wherein the haloalkynyl group contains one or more carbon-carbon triple bonds (i.e., $C_6$-$C_{18}$ haloalkynyl). In other embodiments, the haloalkynyl groups herein can contain any linear, branched, or cyclic alkynyl group containing anywhere from 10 to 16 carbon atoms, having one or more hydrogen atoms replaced by a halogen atom including at least one of F, Cl, Br, I, or At, and wherein the haloalkynyl group contains one or more carbon-carbon triple bonds (i.e., $C_{10}$-$C_{16}$ haloalkynyl).

As used herein, the term "halogenated heteroalkyl" refers to any heteroalkyl group as described herein, containing anywhere from 1 to 20 carbon atoms (i.e., $C_1$-$C_{20}$) and having one or more hydrogen atoms replaced by a halogen atom, including at least one of F, Cl, Br, I, or At (i.e., $C_1$-$C_{20}$ halogenated heteroalkyl). In some embodiments, the halogenated heteroalkyl groups herein can include any heteroalkyl group as described herein, containing anywhere from 6 to 18 carbon atoms (i.e., $C_6$-$C_{18}$) and having one or more hydrogen atoms replaced by a halogen atom, including at least one of F, Cl, Br, I, or At (i.e., $C_6$-$C_{18}$ halogenated heteroalkyl). In other embodiments, the halogenated heteroalkyl groups herein can include any heteroalkyl group as described herein, containing anywhere from 10 to 16 carbon atoms (i.e., $C_{10}$-$C_{16}$) and having one or more hydrogen atoms replaced by a halogen atom, including at least one of F, Cl, Br, I, or At (i.e., $C_{10}$-$C_{16}$ halogenated heteroalkyl).

As used herein, the term "halogenated heteroalkenyl" refers to any heteroalkenyl group as described herein, containing anywhere from 1 to 20 carbon atoms (i.e., $C_1$-$C_{20}$) and having one or more hydrogen atoms replaced by a halogen atom, including at least one of F, Cl, Br, I, or At (i.e., $C_1$-$C_{20}$ halogenated heteroalkenyl). In some embodiments, the halogenated heteroalkenyl groups herein can include any heteroalkenyl group as described herein, containing anywhere from 6 to 18 carbon atoms (i.e., $C_6$-$C_{18}$) and having one or more hydrogen atoms replaced by a halogen atom, including at least one of F, Cl, Br, I, or At (i.e., $C_6$-$C_{18}$ halogenated heteroalkenyl). In other embodiments, the halogenated heteroalkenyl groups herein can include any heteroalkenyl group as described herein, containing anywhere from 10 to 16 carbon atoms (i.e., $C_{10}$-$C_{16}$) and having one or more hydrogen atoms replaced by a halogen atom, including at least one of F, Cl, Br, I, or At (i.e., $C_1$-$C_{16}$ halogenated heteroalkenyl).

As used herein, the term "halogenated heteroalkynyl" refers to any heteroalkynyl group as described herein, containing anywhere from 1 to 20 carbon atoms (i.e., $C_1$-$C_{20}$) and having one or more hydrogen atoms replaced by a halogen atom, including at least one of F, Cl, Br, I, or At (i.e., $C_1$-$C_{20}$ halogenated heteroalkynyl). In some embodiments, the halogenated heteroalkynyl groups herein can include any heteroalkynyl group as described herein, containing anywhere from 6 to 18 carbon atoms (i.e., $C_6$-$C_{18}$) and having one or more hydrogen atoms replaced by a halogen atom, including at least one of F, Cl, Br, I, or At (i.e., $C_6$-$C_{18}$ halogenated heteroalkynyl). In other embodiments, the halogenated heteroalkynyl groups herein can include any heteroalkynyl group as described herein, containing anywhere from 10 to 16 carbon atoms (i.e., $C_{10}$-$C_{16}$) and having one or more hydrogen atoms replaced by a halogen atom, including at least one of F, Cl, Br, I, or At (i.e., $C_{10}$-$C_{16}$ halogenated heteroalkynyl).

As used herein, the term "aryl" refers to any aromatic hydrocarbon functional group containing a $C_5$- to $C_8$-membered aromatic ring, such as, for example, cyclopentadiene, benzene, and derivatives thereof. The corresponding aromatic radicals to the examples provided include, for example, cyclopentadienyl and phenyl radicals, and derivatives thereof. In some embodiments, the aryl functional groups herein can be further substituted to form substituted aryl functional groups. As used herein, the term "substituted aryl" refers to any aromatic hydrocarbon functional group containing a $C_5$- to $C_8$-membered aromatic ring, which itself can be substituted with one or more alkyl, alkenyl, alkynyl, heteroalkyl, heteroalkenyl, or heteroalkynyl functional groups, or any combination thereof, as described herein.

In some embodiments, the aryl functional groups herein can include one or more heteroatoms to form heteroaryl functional groups. Suitable heteroatoms for use herein can include, but not be limited to, N, O, P, S, Si, Se, and B. As used herein, the term "heteroaryl" refers to any aryl functional group, as defined herein, where one or more carbon atoms of the $C_5$- to $C_8$-membered aromatic ring has been replaced with one or more heteroatoms or combinations of heteroatoms. Examples of heteroaryl functional groups can include, but not be limited to radicals of, pyrrole, thiophene, furan, imidazole, pyridine, and pyrimidine. The heteroaryl functional groups herein can be further substituted to form substituted heteroaryl functional groups. As used herein, the term "substituted heteroaryl" refers to any heteroaryl functional group, as described herein, which is further substituted with one or more alkyl, alkenyl, alkynyl, heteroalkyl, heteroalkenyl, or heteroalkynyl functional groups, or any combination thereof, as described herein.

In some embodiments, the aryl functional groups herein can be substituted to form aryloxy functional groups. As used herein, the term "aryloxy" can include a functional group of the general formula Aryl-O—, where the aryl functional group can include a $C_5$- to $C_8$-membered aromatic ring. In some embodiments, the aryloxy group can include a phenoxy functional group of the formula $C_6H_5O$—. In some embodiments, the aryloxy functional group can be further substituted. As used herein, the term "substituted aryloxy" can include any aryloxy functional group, as defined herein, which is further substituted with one or more alkyl, alkenyl, alkynyl, heteroalkyl, heteroalkenyl, or heteroalkynyl functional groups, or any combination thereof, as described herein.

In some embodiments, the aryl functional groups herein can be substituted to form arylthio functional groups. As used herein, the term "arylthio" can include a functional group of the general formula Aryl-S—, where the aryl functional group can include a $C_5$- to $C_8$-membered aromatic ring. In some embodiments, the arylthio functional group can include a phenylsulfanyl functional group of the formula $C_6H_5S$—. In some embodiments, the arylthio functional group can be further substituted. As used herein, the term "substituted arylthio" can include any arylthio functional group, as defined herein, which is further substituted with one or more alkyl, alkenyl, alkynyl, heteroalkyl, heteroalkenyl, or heteroalkynyl functional groups, or any combination thereof, as described herein.

In some embodiments, the aryl functional groups herein can be substituted to form arylamine functional groups. As used herein, the term "arylamine" can include a functional group of the general formula Aryl-$NH_n$, where the aryl functional group can include a $C_5$- to $C_8$-membered aromatic ring, and n can be from 0 to 3, providing that when n=0, 1, or 2, a non-H substitution is present on the N atom, which can include, but is not to be limited to, one or more alkyl, alkenyl, alkynyl, heteroalkyl, heteroalkenyl, or heteroalkynyl functional groups, or any combination thereof, as described herein.

In some embodiments, the arylamine functional group can include a $\lambda^1$-azanylbenzene functional group of the formula $C_6H_5N$. In some embodiments, the arylamine functional group can be further substituted. As used herein, the term "substituted arylamine" can include any arylamine functional group, as defined herein, which is further substituted with one or more alkyl, alkenyl, alkynyl, heteroalkyl, heteroalkenyl, or heteroalkynyl functional groups, or any combination thereof, as described herein.

As used herein, the term "halogenated aryl" refers to an aryl group as described herein including any aromatic group containing a $C_5$- to $C_8$-membered aromatic ring, such as, for example, cyclopentadiene, benzene, and derivatives thereof, or the corresponding aromatic radicals to the examples provided including, for example, cyclopentadienyl and phenyl radicals, and derivatives thereof; where one or more hydrogen atoms of the aryl group or corresponding aromatic radical is replaced by a halogen atom, including at least one of F, Cl, Br, I, or At. In some embodiments, the halogenated aryl group can include a chlorophenyl group. In other embodiments, the halogenated aryl group can include a perfluorphenyl group.

In some embodiments, the halogenated aryl functional groups herein can be further substituted to form substituted halogenated aryl functional groups. As used herein, the term "substituted halogenated aryl" refers to any halogenated aryl group as described herein, which itself can be substituted with one or more alkyl, alkenyl, alkynyl, heteroalkyl, heteroalkenyl, heteroalkynyl, haloalkyl, haloalkenyl, haloalkynyl, halogenated heteroalkyl, halogenated heteroalkenyl, halogenated heteroalkynyl, functional groups, or any combination thereof, as described herein.

As used herein, the term "biphenyl" refers to an aromatic hydrocarbon functional group with the molecular formula $(C_6H_5)_2$, and when bound to a porphyrin or metalloporphyrin has one less hydrogen at the site of covalent attachment to the porphyrin or metalloporphyrin ring structure. In some embodiments, the biphenyl functional group can be substituted to form a substituted biphenyl functional group. As used herein, the term "substituted biphenyl" refers to a biphenyl functional group, as described, which itself is substituted with one or more alkyl, alkenyl, alkynyl, heteroalkyl, heteroalkenyl, or heteroalkynyl functional groups, or any combination thereof, as described herein.

Receptor Molecules for Functionalization of Graphene

The receptor molecules suitable for functionalization of graphene can include any of the pillarenes, substituted pillarenes, calixarenes, substituted calixarenes, peralkylated cyclodextrins, substituted peralkylated cyclodextrins, pyrenes, or substituted pyrenes, as described herein.

Pillarenes

Pillarenes suitable for use herein include those that are substituted or unsubstituted. Pillarenes are a group of heterocyclic macrocycles having 5 to 15 modified hydroquinone subunits, each connected by a methylene ($-CH_2-$) bridge. Without wishing to be bound by any particular theory, it is believed that the hydroquinone subunits of the pillarenes create a symmetrical pillar-like structure defining a central cavity. Because the central cavity can capture analytes of interest for chemical sensing, the pillarenes are an emerging class of macrocycles used in host-guest chemistry. The pillarenes can include those that are substituted at various positions about the benzene ring, including those that are 1,4-disubstituted, 1,2-disubstituted, or 1,5-disubstituted. The basic core structure of a pillarene is as follows:

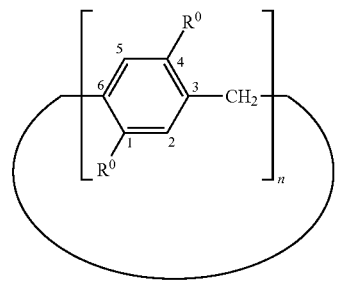

where n is an integer from at least 5 to 15 and where each $R^0$ can independently include $-R^1$, $-OR^1$, or $-SR^1$. Each $R^1$ can independently include: $-H$; $-OH$; $=O$; any linear, branched, or cyclic $C_1$-$C_{20}$ alkyl, $C_1$-$C_{20}$ alkenyl, $C_1$-$C_{20}$ alkynyl, $C_1$-$C_{20}$ heteroalkyl, $C_1$-$C_{20}$ heteroalkenyl, $C_1$-$C_{20}$ heteroalkynyl, $C_1$-$C_{20}$ haloalkyl, $C_1$-$C_{20}$ haloalkenyl, $C_1$-$C_{20}$ haloalkynyl, $C_1$-$C_{20}$ halogenated heteroalkyl, $C_1$-$C_{20}$ halogenated heteroalkenyl, $C_1$-$C_{20}$ halogenated heteroalkynyl, or any combinations thereof; an aryl, heteroaryl, substituted aryl, substituted heteroaryl aryl, halogenated aryl, substituted halogenated aryl, a benzyl or a substituted benzyl, a biphenyl or substituted biphenyl, an aryloxy, arylthio, arylamine, or any substitutions thereof, $-R^2OH$, $-R^2C(O)OH$, $-R^2C(O)OR^2$, $-R^2OR^2$, $-R^2SR^2$, $-R^2CHO$, $-R^2X$ where X is a halogen atom, $-R^2C(O)NH_2$, $-R^2C(O)NR^2$, $-R^2NH_3^+$, $-R^2NH_2$, $-R^2NO_2$, $-R^2NHR^2$, $-R^2NR^2R^2$, $-R^2N_3$, $-R^2OPO(OH)_2$, $-R^2OSO(OH)_2$, or any derivatives or combinations thereof. Each $R^2$ can independently include any identical or different, linear, branched, or cyclic $C_1$-$C_{20}$ alkyl, $C_1$-$C_{20}$ alkenyl, $C_1$-$C_{20}$ alkynyl, $C_1$-$C_{20}$ heteroalkyl, $C_1$-$C_{20}$ heteroalkenyl, $C_1$-$C_{20}$ heteroalkynyl, $C_1$-$C_{20}$ haloalkyl, $C_1$-$C_{20}$ haloalkenyl, $C_1$-$C_{20}$ haloalkynyl, $C_1$-$C_{20}$ halogenated heteroalkyl groups, $C_1$-$C_{20}$ halogenated heteroalkenyl groups, $C_1$-$C_{20}$ halogenated heteroalkynyl groups, or any substitutions or combinations thereof.

In some embodiments, each $R^1$ can independently include any substitutions, any derivatives, or any combinations of any of the forgoing. In various embodiments where an acidic functional group is listed, such as for example $-R^2C(O)OH$, $-R^2OPO(OH)_2$, and $-R^2OSO(OH)_2$, it is to be understood that the corresponding sodium salts, potassium salts, and the like are also contemplated herein. In embodiments where $R^0$ is $-R^1$, $R^1$ can independently include $-X$ such that X is any halogen atom including at least one of F, Cl, Br, I, or At. In some embodiments, at least some of the $R^0$ substituents differ from the other $R^0$ substituents. In other embodiments, the $R^0$ substituents can all be the same.

In some embodiments, the pillarenes suitable for use herein can include those of the general formula:

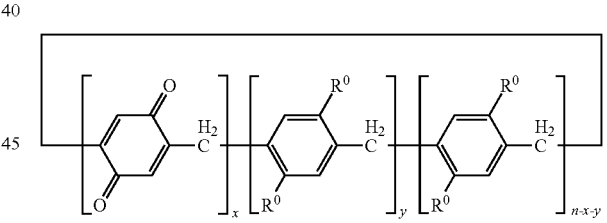

where each $R^0$ can independently include $-R^1$, $-OR^1$, or $-SR^1$, and where x is an integer from at least 0 to 15, y is an integer from at least 0 to 15, and n is an integer from at least 5 to 15. Each $R^1$ can independently include $-H$; $-OH$; $=O$; any linear, branched, or cyclic $C_1$-$C_{20}$ alkyl, $C_1$-$C_{20}$ alkenyl, $C_1$-$C_{20}$ alkynyl, $C_1$-$C_{20}$ heteroalkyl, $C_1$-$C_{20}$ heteroalkenyl, $C_1$-$C_{20}$ heteroalkynyl, $C_1$-$C_{20}$ haloalkyl, $C_1$-$C_{20}$ haloalkenyl, $C_1$-$C_{20}$ haloalkynyl, $C_1$-$C_{20}$ halogenated heteroalkyl groups, $C_1$-$C_{20}$ halogenated heteroalkenyl groups, $C_1$-$C_{20}$ halogenated heteroalkynyl groups, or any combinations thereof; an aryl, heteroaryl, substituted aryl, substituted heteroaryl aryl, halogenated aryl, substituted halogenated aryl, a benzyl or a substituted benzyl, a biphenyl or substituted biphenyl, an aryloxy, arylthio, arylamine, or any substitutions thereof, $-R^2OH$, $-R^2C(O)OH$, $-R^2C(O)OR^2$, $-R^2OR^2$, $-R^2SR^2$, $-R^2CHO$, $-R^2X$ wherein X is a halogen atom, $-R^2C(O)NH_2$, $-R^2C(O)NR^2$, $-R^2NH_3^+$, $-R^2NH_2$, $-R^2NO_2$, $-R^2NHR^2$, $-R^2NR^2R^2$, —$R^2N_3$, —$R^2OPO(OH)_2$, —$R^2OSO(OH)_2$, or any derivatives or combinations thereof. Each $R^2$ can independently include any identical or different, linear, branched, or cyclic $C_1$-$C_{20}$ alkyl, $C_1$-$C_{20}$ alkenyl, $C_1$-$C_{20}$ alkynyl, $C_1$-$C_{20}$ heteroalkyl, $C_1$-$C_{20}$ heteroalkenyl, $C_1$-$C_{20}$ heteroalkynyl, $C_1$-$C_{20}$ haloalkyl, $C_1$-$C_{20}$ haloalkenyl, $C_1$-$C_{20}$ haloalkynyl, $C_1$-$C_{20}$ halogenated heteroalkyl groups, $C_1$-$C_{20}$ halogenated heteroalkenyl groups, $C_1$-$C_{20}$ halogenated heteroalkynyl groups, or any substitutions or combinations thereof.

In some embodiments, each $R^1$ can independently include any substitutions, any derivatives, or any combinations of any of the forgoing. In various embodiments where an acidic functional group is listed, such as for example —$R^2C(O)OH$, —$R^2OPO(OH)_2$, and —$R^2OSO(OH)_2$, it is to be understood that the corresponding sodium salts, potassium salts, and the like are also contemplated herein. In embodiments where $R^0$ is —$R^1$, $R^1$ can independently include —X such that X is any halogen atom including at least one of F, Cl, Br, I, or At. In some embodiments, at least some of the $R^0$ substituents differ from the other $R^0$ substituents. In other embodiments, the $R^0$ substituents can all be the same.

In various embodiments, pillarenes suitable for use herein can include those such as dimethoxypillar[5]arene or dimethoxypillar[4]arene[1]quinone. In some embodiments, the pillarene suitable for use herein includes dimethoxypillar[5]arene of the chemical structure:

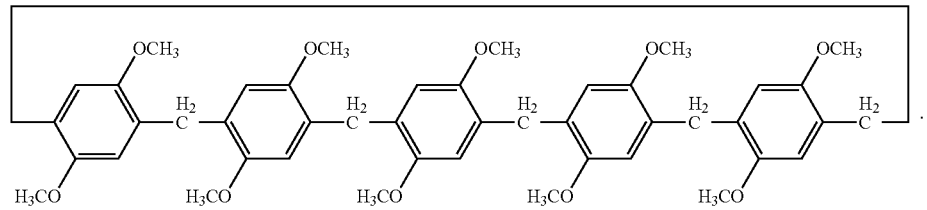 [SMILES: COc1cc2c(OC)cc1CCCCCc1cc(OC)c(cc1OC)Cc1cc(OC)c(cc1OC)Cc1cc(OC)c(cc1OC)Cc1cc(OC)c(cc1OC)C2]

In other embodiments, the pillarene suitable for use herein includes dimethoxypillar[4]arene[1]quinone of the chemical structure:

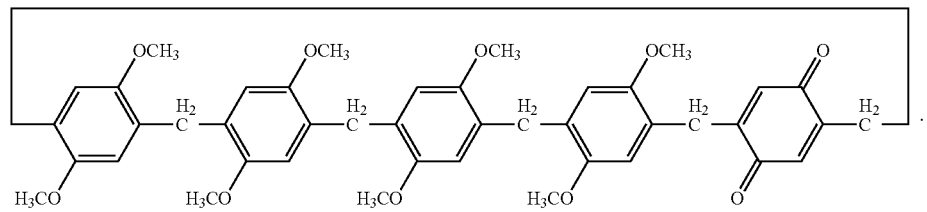 [SMILES: COc1cc2c(OC)cc1CCCCCC1=CC(=O)C(=CC1=O)Cc1cc(OC)c(cc1OC)Cc1cc(OC)c(cc1OC)Cc1cc(OC)c(cc1OC)C2]

Calixarenes

Calixarenes are a group of heterocyclic macrocycles having from 3 to 15 aromatic components derived from compounds such as phenol, where each component is connected by a substituted or unsubstituted methylene (—$CH_2$—) bridge. Without wishing to be bound by any particular theory, it is believed that the subunits of the calixarenes can create a cup-like shape defining a central cavity. Because the central cavity can capture analytes of interest for chemical sensing, the calixarenes are an emerging class of macrocycles used in host-guest chemistry. Calixarenes suitable for use herein include those that are substituted or unsubstituted. Some exemplary structures of a calixarenes include:

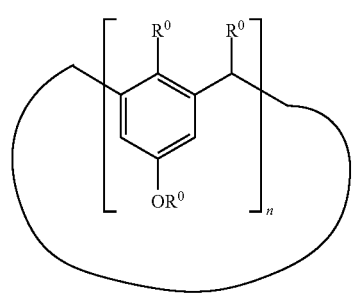

(a.)

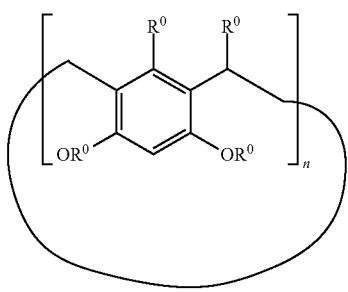

(b.)

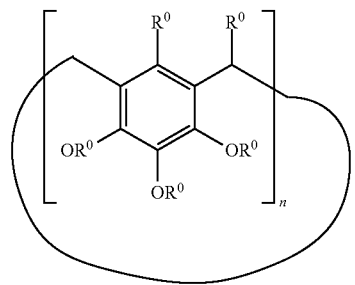

(c.)

where n is an integer from at least 3 to 15 and each $R^0$ can independently include —$R^1$, —OR, or —$SR^1$. Each $R^1$ can independently include —H; —OH; any linear, branched, or cyclic $C_1$-$C_{20}$ alkyl, $C_1$-$C_{20}$ alkenyl, $C_1$-$C_{20}$ alkynyl, $C_1$-$C_{20}$ heteroalkyl, $C_1$-$C_{20}$ heteroalkenyl, $C_1$-$C_{20}$ heteroalkynyl, $C_1$-$C_{20}$ haloalkyl, $C_1$-$C_{20}$ haloalkenyl, $C_1$-$C_{20}$ haloalkynyl, $C_1$-$C_{20}$ halogenated heteroalkyl groups, $C_1$-$C_{20}$ halogenated heteroalkenyl groups, $C_1$-$C_{20}$ halogenated heteroalkynyl groups, or any combinations thereof, an aryl, heteroaryl, substituted aryl, substituted heteroaryl aryl, halogenated aryl, substituted halogenated aryl, a benzyl or a substituted benzyl, a biphenyl or substituted biphenyl, an aryloxy, arylthio, arylamine, or any substitutions thereof, —$R^2$OH, —$R^2$C(O)OH, —$R^2$C(O)O$R^2$, —$R^2$O$R^2$, —$R^2$S$R^2$, —$R^2$CHO, —$R^2$X wherein X is a halogen atom, —$R^2$C(O)NH$_2$, —$R^2$C(O)N$R^2$, —$R^2$NH$_3^+$, —$R^2$NH$_2$, —$R^2$NO$_2$, —$R^2$NH$R^2$, —$R^2$N$R^2$$R^2$, —$R^2$N$_3$, —$R^2$OPO(OH)$_2$, —$R^2$OSO(OH)$_2$, or any derivatives or combinations thereof. Each $R^2$ can independently include any identical or different, linear, branched, or cyclic $C_1$-$C_{20}$ alkyl, $C_1$-$C_{20}$ alkenyl, $C_1$-$C_{20}$ alkynyl, $C_1$-$C_{20}$ heteroalkyl, $C_1$-$C_{20}$ heteroalkenyl, $C_1$-$C_{20}$ heteroalkynyl, $C_1$-$C_{20}$ haloalkyl, $C_1$-$C_{20}$ haloalkenyl, $C_1$-$C_{20}$ haloalkynyl, $C_1$-$C_{20}$ halogenated heteroalkyl groups, $C_1$-$C_{20}$ halogenated heteroalkenyl groups, $C_1$-$C_{20}$ halogenated heteroalkynyl groups, or any substitutions or combinations thereof.

In some embodiments, each $R^1$ can independently include any substitutions, any derivatives, or any combinations of any of the forgoing. In various embodiments where an acidic functional group is listed, such as for example —$R^2$C(O)OH, —$R^2$OPO(OH)$_2$, and —$R^2$OSO(OH)$_2$, it is to be understood that the corresponding sodium salts, potassium salts, and the like are also contemplated herein. In embodiments where $R^0$ is —$R^1$, $R^1$ can independently include —X such that X is any halogen atom including at least one of F, Cl, Br, I, or At. In some embodiments, at least some of the $R^0$ substituents differ from the other $R^0$ substituents. In other embodiments, the $R^0$ substituents can all be the same.

Peralkylated Cyclodextrins

Various peralkylated cyclodextrins can be suitable for use in modifying modify a surface of graphene as described herein. Peralkylated cyclodextrins suitable for use herein include those that are substituted or unsubstituted. In some embodiments, the peralkylated cyclodextrins can include, but are not limited to α-, β- and γ-cyclodextrins and derivatives thereof. In some embodiments, the peralkylated cyclodextrins and their derivatives can include, but not be limited to those having the formula:

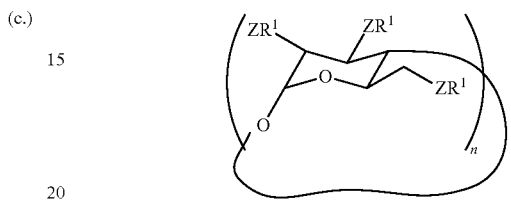

where n can be any integer from 5 to 10, or any integer from 6 to 8, and where Z can be —S or —O. Each $R^1$ can independently include: —H; any linear, branched, or cyclic $C_1$-$C_{20}$ alkyl, $C_1$-$C_{20}$ alkenyl, $C_1$-$C_{20}$ alkynyl, $C_1$-$C_{20}$ heteroalkyl, $C_1$-$C_{20}$ heteroalkenyl, $C_1$-$C_{20}$ heteroalkynyl, $C_1$-$C_{20}$ haloalkyl, $C_1$-$C_{20}$ haloalkenyl, $C_1$-$C_{20}$ haloalkynyl, $C_1$-$C_{20}$ halogenated heteroalkyl groups, $C_1$-$C_{20}$ halogenated heteroalkenyl groups, $C_1$-$C_{20}$ halogenated heteroalkynyl groups, or any combination thereof; an aryl, heteroaryl, substituted aryl, substituted heteroaryl aryl, halogenated aryl, substituted halogenated aryl, a benzyl or a substituted benzyl, a biphenyl or substituted biphenyl, an aryloxy, arylthio, or arylamine; —$R^2$OH, —$R^2$C(O)OH, —$R^2$C(O)O$R^2$, —$R^2$O$R^2$, —$R^2$S$R^2$, —$R^2$CHO, —$R^2$X where X is a halogen atom, —$R^2$C(O)NH$_2$, —$R^2$C(O)N$R^2$, —$R^2$NH$_3^+$, —$R^2$NH$_2$, —$R^2$NO$_2$, —$R^2$NH$R^2$, —$R^2$N$R^2$$R^2$, —$R^2$N$_3$, —$R^2$OPO(OH)$_2$, —$R^2$OSO(OH)$_2$, or any derivatives or combinations thereof. Each $R^2$ can independently include any identical or different, linear, branched, or cyclic $C_1$-$C_{20}$ alkyl, $C_1$-$C_{20}$ alkenyl, $C_1$-$C_{20}$ alkynyl, $C_1$-$C_{20}$ heteroalkyl, $C_1$-$C_{20}$ heteroalkenyl, $C_1$-$C_{20}$ heteroalkynyl, $C_1$-$C_{20}$ haloalkyl, $C_1$-$C_{20}$ haloalkenyl, $C_1$-$C_{20}$ haloalkynyl, $C_1$-$C_{20}$ halogenated heteroalkyl groups, $C_1$-$C_{20}$ halogenated heteroalkenyl groups, $C_1$-$C_{20}$ halogenated heteroalkynyl groups, or a combination thereof. In some embodiments, each $R^1$ can independently include any substitutions, any derivatives, or any combinations of any of the forgoing. In some embodiments, each $R^1$ can independently include any substitutions, any derivatives, or any combinations of any of the forgoing.

In various embodiments where an acidic functional group is listed, such as for example —$R^2$C(O)OH, —$R^2$OPO(OH)$_2$, and —$R^2$OSO(OH)$_2$, it is to be understood that the corresponding sodium salts, potassium salts, and the like are also contemplated herein. In some embodiments, the presence of one or more hydroxyl groups or amino groups can contribute to hydrogen bonding between the cyclodextrin molecules and the graphene layer. In various embodiments where Z$R^1$ can be replaced with —X such that X is any halogen atom including at least one of F, Cl, Br, I, or At.

In some embodiments, the peralkylated cyclodextrin suitable for use herein includes can include heptakis (2,3,6-tri-O-methyl)-β-cyclodextrin (herein "β-CDMe$_{21}$") having the chemical structure:

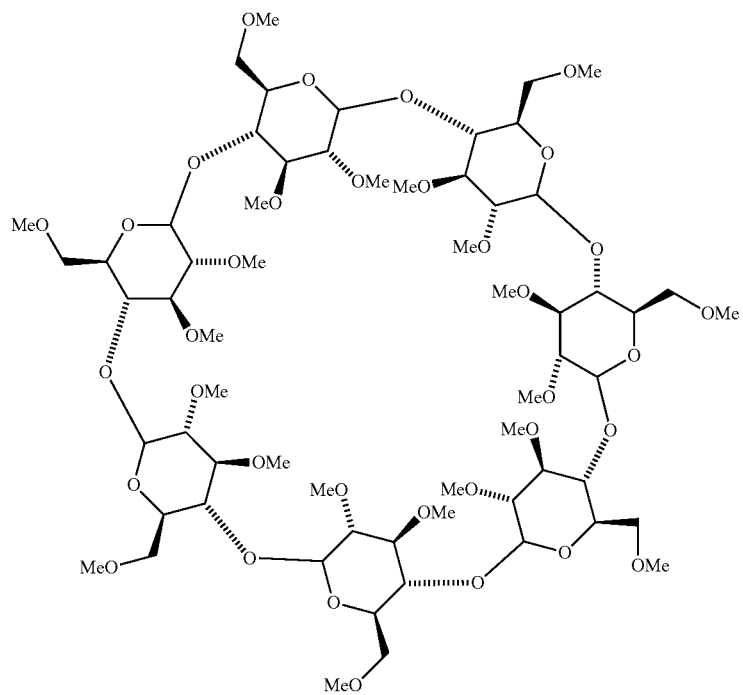

Polycyclic Aromatic Hydrocarbons

Various polycyclic aromatic hydrocarbon compounds can be suitable for use in modifying modify a surface of graphene as described herein. Polycyclic aromatic hydrocarbon compounds suitable for use herein include those that are substituted or unsubstituted. As described herein, a polycyclic aromatic hydrocarbon can be described by the formula:

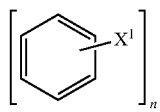

where n is an integer from at least 3 to 20 and each X can be any substitution, independently including, but not limited to, —$R^1$, —$OR^1$, or —$SR^1$. Each $R^1$ can independently include: —H, —OH, —C(O)OH, —C(O)O$R^2$, —O$R^2$, —S$R^2$, —CHO, —X where X is a halogen atom, —C(O)NH$_2$, —C(O)N$R^2$, —NH$_3^+$, —NH$_2$, —NO$_2$, —NH$R^2$, —N$R^2R^2$, —N$_3$, —B(OH)$_2$, —OPO(OH)$_2$, —OSO(OH)$_2$, any linear, branched, or cyclic $C_1$-$C_{20}$ alkyl, $C_1$-$C_{20}$ alkenyl, $C_1$-$C_{20}$ alkynyl, $C_1$-$C_{20}$ heteroalkyl, $C_1$-$C_{20}$ heteroalkenyl, $C_1$-$C_{20}$ heteroalkynyl, $C_1$-$C_{20}$ haloalkyl, $C_1$-$C_{20}$ haloalkenyl, $C_1$-$C_{20}$ haloalkynyl, $C_1$-$C_{20}$ halogenated heteroalkyl, $C_1$-$C_{20}$ halogenated heteroalkenyl, $C_1$-$C_{20}$ halogenated heteroalkynyl, or any combinations thereof; an aryl, heteroaryl, substituted aryl, substituted heteroaryl aryl, halogenated aryl, substituted halogenated aryl, a benzyl or a substituted benzyl, a biphenyl or substituted biphenyl, an aryloxy, arylthio, arylamine, or any substitutions thereof, —$R^2$OH, —$R^2$C(O)OH, —$R^2$C(O)O$R^2$, —$R^2$O$R^2$, —$R^2$S$R^2$, —$R^2$CHO, —$R^2$X where X is a halogen atom, —$R^2$C(O)NH$_2$, —$R^2$C(O)N$R^2$, —$R^2$NH$_3^+$, —$R^2$NH$_2$, —$R^2$NO$_2$, —$R^2$NH$R^2$, —$R^2$N$R^2R^2$, —$R^2$N$_3$, —$R^2$B(OH)$_2$, —$R^2$OPO(OH)$_2$, —$R^2$OSO(OH)$_2$, or any derivatives or combinations thereof. Each $R^2$ can independently include any identical or different, linear, branched, or cyclic $C_1$-$C_{20}$ alkyl, $C_1$-$C_{20}$ alkenyl, $C_1$-$C_{20}$ alkynyl, $C_1$-$C_{20}$ heteroalkyl, $C_1$-$C_{20}$ heteroalkenyl, $C_1$-$C_{20}$ heteroalkynyl, $C_1$-$C_{20}$ haloalkyl, $C_1$-$C_{20}$ haloalkenyl, $C_1$-$C_{20}$ haloalkynyl, $C_1$-$C_{20}$ halogenated heteroalkyl groups, $C_1$-$C_{20}$ halogenated heteroalkenyl groups, $C_1$-$C_{20}$ halogenated heteroalkynyl groups, or any substitutions or combinations thereof.

In some embodiments, each $R^1$ can independently include any substitutions, any derivatives, or any combinations of any of the forgoing. In various embodiments where an acidic functional group is listed, such as for example —$R^2$B(OH)$_2$, —$R^2$C(O)OH, —$R^2$OPO(OH)$_2$, and —$R^2$OSO(OH)$_2$, it is to be understood that the corresponding sodium salts, potassium salts, and the like are also contemplated herein. In embodiments where X is —$R^1$, $R^1$ can independently include —X such that X is any halogen atom including at least one of F, Cl, Br, I, or At.

In some embodiments, the polycyclic aromatic hydrocarbon can include pyrenes, substituted pyrenes, and pyrene derivatives described by the formula:

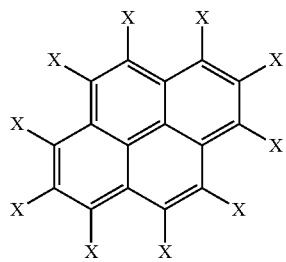

where X can be any substitution, including, but not limited to, $R^1$, —$OR^1$, or $SR^1$. Each $R^1$ can independently include: —H, —OH, —C(O)OH, —C(O)O$R^2$, —O$R^2$, —S$R^2$, —CHO, —X where X is a halogen atom, —C(O)NH$_2$, —C(O)NR², —NH₃⁺, —NH₂, —NO₂, —NHR², —NR²R², —N₃, —B(OH)₂, —OPO(OH)₂, —OSO(OH)₂, any linear, branched, or cyclic $C_1$-$C_{20}$ alkyl, $C_1$-$C_{20}$ alkenyl, $C_1$-$C_{20}$ alkynyl, $C_1$-$C_{20}$ heteroalkyl, $C_1$-$C_{20}$ heteroalkenyl, $C_1$-$C_{20}$ heteroalkynyl, $C_1$-$C_{20}$ haloalkyl, $C_1$-$C_{20}$ haloalkenyl, $C_1$-$C_{20}$ haloalkynyl, $C_1$-$C_{20}$ halogenated heteroalkyl, $C_1$-$C_{20}$ halogenated heteroalkenyl, $C_1$-$C_{20}$ halogenated heteroalkynyl, or any combinations thereof; an aryl, heteroaryl, substituted aryl, substituted heteroaryl aryl, halogenated aryl, substituted halogenated aryl, a benzyl or a substituted benzyl, a biphenyl or substituted biphenyl, an aryloxy, arylthio, arylamine, or any substitutions thereof, —R²OH, —R²C(O)OH, —R²C(O)OR², —R²OR², —R²SR², —R²CHO, —R²X where X is a halogen atom, —R²C(O)NH₂, —R²C(O)NR², —R²NH₃, —R²NH₂, —R²NO₂, —R²NHR², —R²NR²R², —R²N₃, —R²B(OH)₂, —R²OPO(OH)₂, —R²OSO(OH)₂, or any derivatives or combinations thereof. Each R² can independently include any identical or different, linear, branched, or cyclic $C_1$-$C_{20}$ alkyl, $C_1$-$C_{20}$ alkenyl, $C_1$-$C_{20}$ alkynyl, $C_1$-$C_{20}$ heteroalkyl, $C_1$-$C_{20}$ heteroalkenyl, $C_1$-$C_{20}$ heteroalkynyl, $C_1$-$C_{20}$ haloalkyl, $C_1$-$C_{20}$ haloalkenyl, $C_1$-$C_{20}$ haloalkynyl, $C_1$-$C_{20}$ halogenated heteroalkyl groups, $C_1$-$C_{20}$ halogenated heteroalkenyl groups, $C_1$-$C_{20}$ halogenated heteroalkynyl groups, or any substitutions or combinations thereof.

In some embodiments, each R¹ can independently include any substitutions, any derivatives, or any combinations of any of the forgoing. In various embodiments where an acidic functional group is listed, such as for example —R²B(OH)₂, —R²C(O)OH, —R²OPO(OH)₂, and —R²OSO(OH)₂, it is to be understood that the corresponding sodium salts, potassium salts, and the like are also contemplated herein. In embodiments where X is —R¹, R¹ can independently include —X such that X is any halogen atom including at least one of F, Cl, Br, I, or At.

In some embodiments, the polycyclic aromatic hydrocarbon can include those having the formula pyrenyl-(CH₂)ₙ—SO₃X, where n is a number between 0 and 10 and X is H or a metal cation including, but not to be limited to, Na, K, Li, Rb, Cs, Mg, Ca, or Sr. As used herein, the term "pyrenyl" refers to a pyrene group.

In some embodiments, the polycyclic aromatic hydrocarbon can include 1-pyrene sulfonic acid described by the formula:

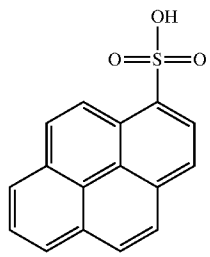 [SMILES: O=S(=O)(O)c1ccc2ccc3cccc4ccc1c2c34]

Langmuir Adsorption Theory

Without wishing to be bound by any particular theory, it is believed that according to Langmuir adsorption theory, monolayer modification of graphene can be controlled by varying the concentration of the adsorbate in the bulk of the self-assembly solution according to:

$$\theta = \frac{K*C}{1+K*C} \quad (1)$$

where θ is the fractional surface coverage, C is the concentration of the adsorbate in the bulk of the self-assembly solution, and K is the equilibrium constant for adsorption of the adsorbate to graphene. Experimentally, the surface coverage can be expressed by the change in contact angle between bare graphene and modified graphene according to:

$$\theta = \frac{\Phi(i) - \Phi(\text{bare})}{\Phi(\text{sat.}) - \Phi(\text{bare})} \quad (2)$$

where Φ(i) is the contact angle of the modified graphene as a function of the concentration in the self-assembly solution, Φ(bare) is the contact angle of bare graphene, and Φ(sat.) is the contact angle of graphene modified with a complete monolayer of receptor molecules (i.e., 100% surface coverage or θ=1.0), where the receptor molecules can include one or more of a pillarene, substituted pillarene, calixarene, substituted calixarene, peralkylated cyclodextrin, or substituted peralkylated cyclodextrin and their derivatives. Insertion of θ from eq. (2) into eq. (1) and solving for Φ(i) gives eq. (3)

$$\Phi(i) = \Phi(\text{bare}) + \frac{K*C[\Phi(\text{sat.})-\Phi(\text{bare})]}{1+K*C} \quad (3)$$

Thus, the experimentally observed Φ(i) values can be fitted as a function of receptor concentration in the self-assembly solution, using the two fitting parameters K and Φ(sat.). Once these two parameters have been determined, relative surface coverages at different self-assembly concentrations can be predicted from eq. (1), using K.

Data can be fitted with the Langmuir adsorption model to determine the equilibrium constants for surface adsorption and the concentrations of self-assembly solutions needed to form dense monolayers having 90% or greater surface coverage (i.e., θ>0.9) on graphene. In some embodiments, a surface coverage of at least 90% or greater is desired. In some embodiments, a surface coverage of at least 95% or greater is desired. In some embodiments, a surface coverage of at least 98% or greater is desired.

Figure 9:
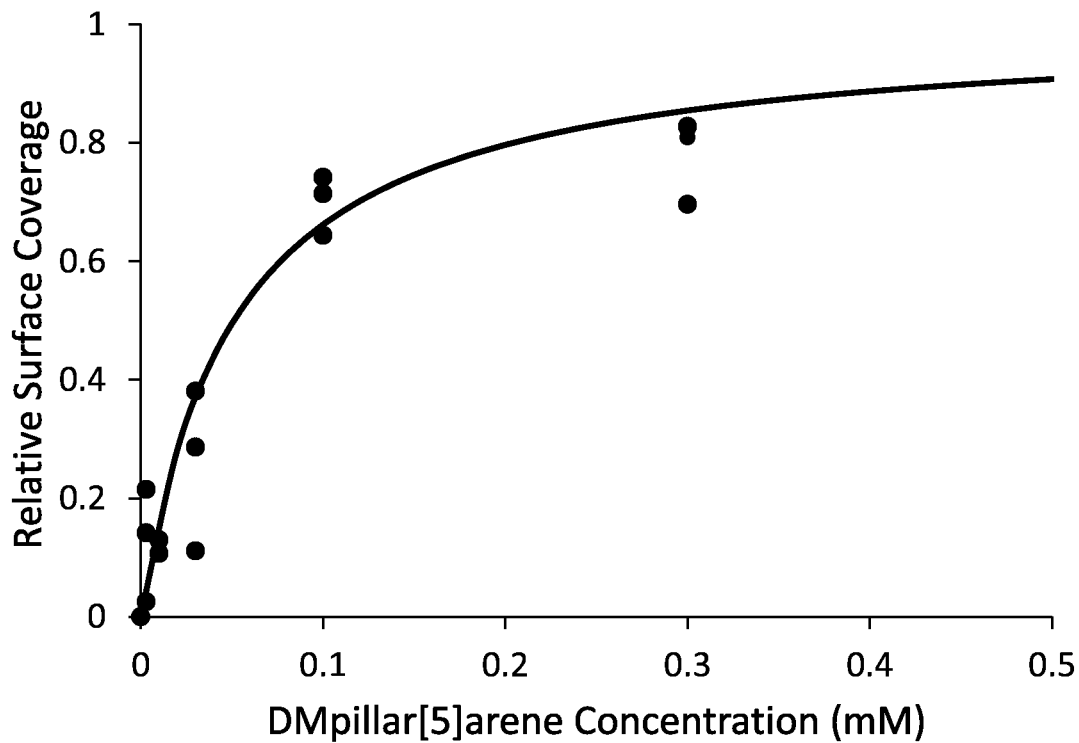
FIG. 9 is a representative plot of relative surface coverage as a function of concentration in accordance with various embodiments herein.
Figure 10:
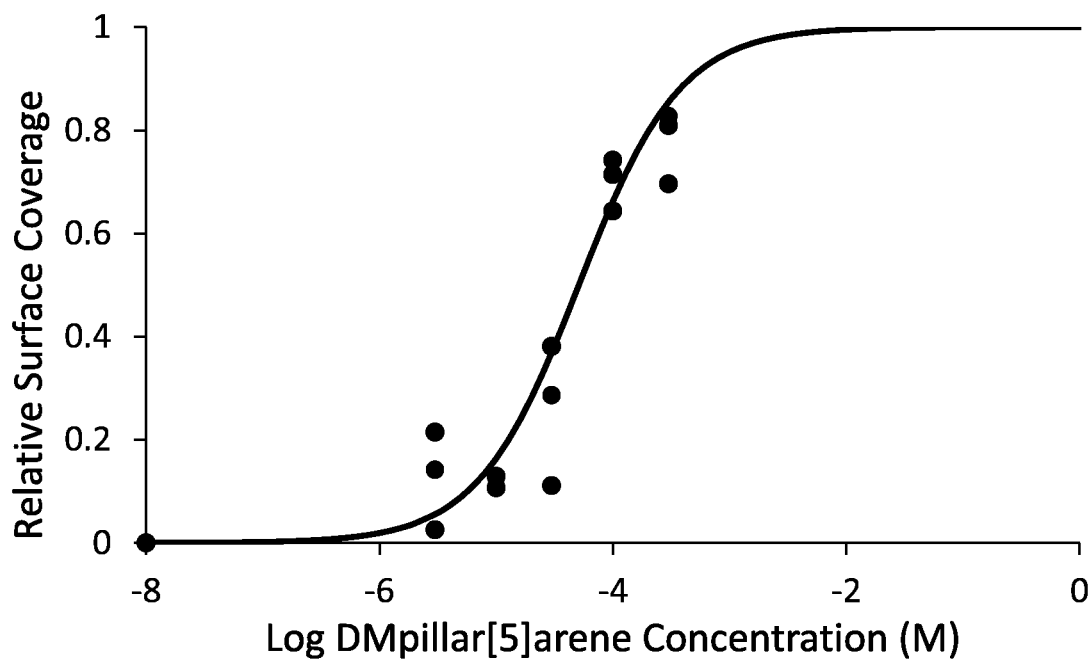
FIG. 10 is a representative plot of relative surface coverage as a function of the logarithm of concentration presented in FIG. 10, in accordance with various embodiments herein.

A representative Langmuir adsorption isotherm for the adsorption of a substituted pillararene to graphene is shown in FIG. 9 and described more fully in Examples 1-3 below. The data show the relative monolayer coverage (dots) along with a fit based on Langmuir adsorption theory (solid line) for the adsorption of dimethoxypillar[5]arene (herein "DMpillar[5]arene") to graphene, as determined by XPS measurements. The relative surface coverage for the adsorption of DMpillar[5]arene to graphene as a function of the logarithm of the DMpillar[5]arene concentration in the self-assembly solution is shown in FIG. 10.

In the above example, the Langmuir model is used to determine K from the elemental compositions of the bare graphene and modified graphene surfaces obtained using X-ray photoelectron spectroscopy (XPS). Instead of using XPS data, data obtained with infrared spectroscopy or Raman spectroscopy, or contact angle goniometry can also be used.

X-Ray Photoelectron Spectroscopy

X-ray photoelectron spectroscopy (XPS) is a highly sensitive spectroscopic technique that can quantitatively measure the elemental composition of a surface of a material. The process of XPS involves irradiation of a surface with X-rays under a vacuum, while measuring the kinetic energy and electron release within the top 0 to 10 nm of a material. Without wishing to be bound by any particular theory, it is believed that XPS can be used to confirm the presence of a self-assembled monolayer formed on the surface of graphene.

The surface concentrations of the types of atoms that the monolayer, graphene, and the underlying substrate consist of (as determined from XPS) depends on the Langmuir theta value of the monolayer or, in other words, the surface density of the monolayer molecules on the graphene. For example, the surface concentrations of carbon, oxygen, and copper (i.e., C %, O %, and Cu %, as determined from XPS) for the monolayers of any given cyclodextrin on a copper substrate depends on the concentration of that cyclodextrin in the self-assembly solution. Due to experimental error, a slightly different value of the equilibrium constant, K, for surface adsorption will result when either the C %, O %, or Cu % data are fitted separately. However, because the C %, O %, or Cu % data characterize the same equilibrium, there is only one true value for K. Therefore, the XPS data can not only be fitted separately for the C %, O %, and Cu % data but also as one combined set of data. Fitting of the combined data for several types of atoms that the monolayer, graphene, and the underlying substrate consist of gives more accurate estimates of the true value of K. For this purpose, the following equation can be used, where each data point consists of a vector comprising (i) an index, (ii) the concentration of the self-assembly solution, and (iii) the carbon, oxygen, or copper concentration as determined by XPS.

$$KroneckerDelta[1 - index] *$$
$$\left\{ C\ \%(bare) + \frac{K * Conc * [C\ \%(sat.) - C\ \%(bare)]}{1 + K * Conc} \right\} +$$
$$KroneckerDelta[2 - index] *$$
$$\left\{ O\ \%(bare) + \frac{K * Conc * [O\ \%(sat.) - O\ \%(bare)]}{1 + K * Conc} \right\} +$$
$$KroneckerDelta[3 - index] *$$
$$\left\{ Cu\ \%(bare) + \frac{K * Conc * [Cu\ \%(sat.) - Cu\ \%(bare)]}{1 + K * Conc} \right\}$$

The index 1 was used for the C % data, 2 for the O % data, and 3 for the Cu % data. The output of the Kronecker delta for the input of 0 is 1, and it is 0 for any other input. This fitting procedure provides in one step the maximum surface concentrations of carbon, oxygen, and copper (i.e., C % (sat.), O % (sat.), and Cu % (sat.), respectively) along with one single value for K for all three adsorption isotherms.

In the example above, the K value is fitted from 3 adsorption isotherms, that is, the surface concentrations of 3 types of atoms. The same type of fit may also be performed for adsorption isotherms of 1, 2, 3, 4, 5, 6, 7, 8, 9, 10, or more different types of atoms.

The equilibrium constant K, as determined by the fit of the XPS data, can be used in the Langmuir adsorption model to determine the θ value for graphene surfaces modified with various molecules forming monolayers on graphene, such as pillarenes, substituted pillarenes, calixarenes, substituted calixarenes, and their derivatives. A representative Langmuir adsorption isotherm for the adsorption of graphene modified with dimethoxypillar[5]arene is shown in FIG. 9 and described in more detail in Examples 1-3.

Contact Angle Goniometry

Contact angle goniometry can be used to determine the wettability of a solid surface by a liquid. Wettability, or wetting, can result from the intermolecular forces at the contact area between a liquid and a solid surface. The degree of wetting can be described by the value of the contact angle θ formed between the area of contact between the liquid and the solid surface and a line tangent to the liquid-vapor interface. When a surface of a solid is hydrophilic and water is used as the test liquid, (i.e., a high degree of wettability), the value for Φ can fall within a range of 0 to 90 degrees. When a surface of a solid is moderately hydrophilic to hydrophobic, (i.e., a medium degree of wettability), the value for Φ for water as the test liquid can fall within a range of 85 to 105 degrees. When the surface of a solid is highly hydrophobic, (i.e., a low degree of wettability), the value for Φ with water as the test liquid can fall within a range of 90 to 180 degrees. Thus, a change in contact angle can be reflective of a change in the surface chemistry of a substrate.

Graphene surfaces and modifications made to graphene surfaces can be characterized using contact angle goniometry. Contact angle goniometry can provide quantitative information regarding the degree of modification of the graphene surface. Contact angle measurements are highly sensitive to the functional groups present on sample surfaces and can be used to determine the formation and extent of surface coverage of self-assembled monolayers. A change in the contact angle from a bare graphene surface as compared to one that has been immersed into a self-assembly solution containing π-electron-rich molecules, can be used to confirm the formation of the self-assembled monolayer on the surface of the graphene.

The types of solvents suitable for use in determining contact angle measurements, also called wetting solutions, are those that maximize the difference between the contact angle of the solution on bare graphene and the contact angle on the modified graphene, thereby improving data accuracy for measurements of binding isotherms. In some embodiments, the wetting solutions can include, but are not limited to, deionized (DI) water, NaOH aqueous solution, borate buffer (pH 9.0), other pH buffers, $CF_3CH_2OH$, and the like. In some embodiments, the wetting solutions are polar. In some embodiments, the wetting solutions are non-polar.

Methods

The pillarenes, substituted pillarenes, calixarenes, substituted calixarenes, peralkylated cyclodextrins, substituted peralkylated cyclodextrins, pyrenes, or substituted pyrenes herein can be used in one or more methods for modifying a surface of graphene. In one embodiment, a method can include forming a self-assembled monolayer disposed on an outer surface of a graphene layer through non-covalent interactions between the self-assembled monolayer and a π-electron system of graphene. The method can include a self-assembled monolayer including one or more pillarenes, substituted pillarenes, calixarenes, or substituted calixarenes, or derivatives thereof, as described elsewhere herein. The method can include quantifying the extent of surface coverage of the self-assembled monolayer using contact angle goniometry, Raman spectroscopy, or X-Ray photoelectron spectroscopy. In some embodiments, that non-covalent interactions can include electrostatic interactions. In other embodiments, the non-covalent interactions can include π-π stacking interactions.

In some embodiments, the method can include selecting derivatized graphene layers that exhibit a Langmuir theta value of at least 0.9. In other embodiments, the method includes selecting derivatized graphene layers that exhibit a Langmuir theta value of at least 0.98.

The pillarenes, substituted pillarenes, calixarenes, substituted calixarenes, peralkylated cyclodextrins, substituted peralkylated cyclodextrins, pyrenes, or substituted pyrenes herein can be used in one or more methods for modifying a surface of graphene. In one embodiment, a method can include detecting an analyte. The method can include collecting a gaseous sample and contacting the gaseous sample with one or more graphene varactors. The one or more graphene varactors can include a graphene layer, and a self-assembled monolayer disposed on an outer surface of the graphene layer through non-covalent interactions between the self-assembled monolayer and a π-electron system of graphene. The self-assembled monolayer can include at least one selected from the group including of pillarenes, substituted pillarenes, calixarenes, substituted calixarenes, peralkylated cyclodextrins, substituted peralkylated cyclodextrins, pyrenes, or substituted pyrenes, or derivatives thereof, as described elsewhere herein. The method can further include measuring a differential response in an electrical property of the one or more graphene varactors due to the binding of one or more analytes present in the gaseous sample, where the electrical property can be selected from the group including of capacitance or resistance Aspects may be better understood with reference to the following examples. These examples are intended to be representative of specific embodiments, but are not intended as limiting the overall scope of embodiments herein.

EXAMPLES

Example 1: Experimental Materials

Dimethoxypillar[5]arene (herein "DMpillar[5]arene") was purchased from Tokyo Chemical Industry (Cambridge, MA). Monolayer graphene on Cu foil was purchased from Graphenea (Donostia, Spain). Heptakis(2,3,6-tri-O-methyl)-β-cyclodextrin (herein "β-CDMe$_2$"), hexane and acetonitrile was purchased from Sigma-Aldrich (St. Louis, MO). The chemical structure of DMpillar[5]arene is as follows:

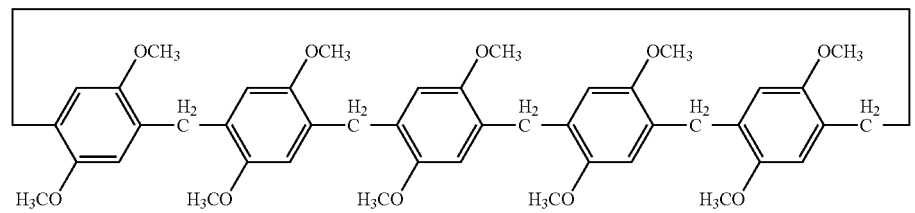 [SMILES: COc1cc2c(OC)cc1CCCCCc1cc(OC)c(cc1OC)Cc1cc(OC)c(cc1OC)Cc1cc(OC)c(cc1OC)Cc1cc(OC)c(cc1OC)C2]

The chemical structure of β-CDMe$_{21}$ is as follows:

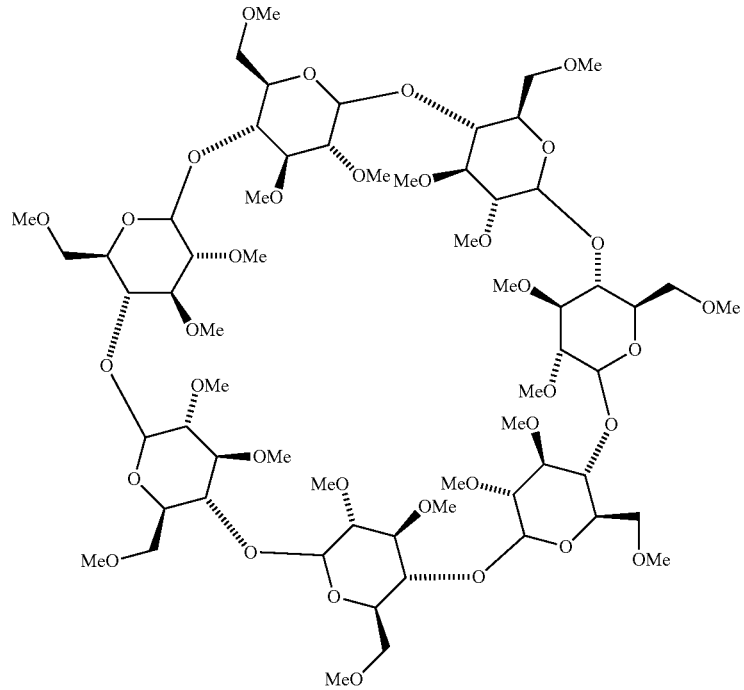

Example 2: Graphene Surface Modification Through Self-Assembly of DMPillar[5]Arene Acetonitrile was used as the self-assembly solvent. Graphene substrates were immersed overnight into DMpillar[5]arene solutions at various concentrations, including 0 millimolar (mM), 0.0030 mM, 0.010 mM, 0.030 mM, 0.10 mM, or 0.30 mM. The DMpillar[5]arene-modified graphene substrates were then washed 3 times with small portions of the acetonitrile solvent to remove excess self-assembly solution.

Example 3: Surface Characterization of Graphene Modified with DMPillar[5]Arene X-ray photoelectron spectroscopy (XPS) spectra of bare graphene and graphene modified with DMpillar[5]arene were collected on a VersaProbe III Scanning XPS Microprobe (PHI 5000, 5 Physical Electronics, Chanhassen, MN). The results for the elemental surface composition of graphene modified with DMpillar[5]arene are shown in Table 1.

TABLE 1

Elemental surface composition of graphene modified with DMpillar[5]arene, as determined by XPS.

| DMpillar[5]arene Concentration (mM) in self-assembly solution | C % | Cu % | O % |
| --- | --- | --- | --- |
| 0 | 54.2 ± 0.4 | 6.7 ± 0.9 | 39.1 ± 0.8 |
| 0.0030 | 57.7 ± 1.8 | 7.0 ± 1.0 | 35.3 ± 2.0 |
| 0.010 | 56.3 ± 1.7 | 8.1 ± 0.5 | 35.6 ± 1.5 |
| 0.030 | 60.4 ± 1.8 | 8.1 ± 0.9 | 31.5 ± 1.4 |
| 0.10 | 65.8 ± 0.6 | 15.0 ± 0.6 | 19.3 ± 0.1 |
| 0.30 | 67.3 ± 2.6 | 15.7 ± 1.3 | 17.0 ± 1.3 |

The C %, O % and Cu % data were fitted simultaneously, as described above, to determine the equilibrium constant K. The equilibrium constant, K, and concentration of self-assembly solution needed for at least 90% monolayer formation with DMpillar[5]arene are shown in Table 2.

TABLE 2

Equilibrium constant and monolayer concentration for adsorption of DMpillar[5]arene to graphene.

| Self-Assembly Molecule | Log K (Log M$^{-1}$) | Self-assembly solvent | Concentration of self-assembly solution needed for 90% surface coverage (mM) |
| --- | --- | --- | --- |
| DMpillar[5]arene | 4.29 (4.14-4.40) | acetonitrile | 0.47 |

The Langmuir adsorption isotherm for the adsorption of graphene modified with DMpillar[5]arene is shown in FIG. 9. The figure shows the relative monolayer coverage (dots) along with a fit (solid line) based on Langmuir adsorption theory for the adsorption of graphene modified with DMpillar[5]arene, as determined by XPS data. The relative surface coverage for the adsorption of DMpillar[5]arene to graphene as a function of the logarithm of the DMpillar[5]arene concentration in the self-assembly solution is shown in FIG. 10.

Example 4: Graphene Surface Modification Through Self-Assembly of β-CDMe$_{21}$ Hexane was used as the self-assembly solvent. Graphene substrates were immersed overnight into β-CDMe$_{21}$ solutions at various concentrations, including 0 millimolar (mM), 0.0050 mM, 0.010 mM, 0.050 mM, 0.10 mM, or 0.50 mM. The β-CDMe$_{21}$-modified graphene substrates were then washed 3 times with small portions of the hexane solvent to remove excess self-assembly solution.

Example 5: Surface Characterization of Graphene Modified with β-CDMe$_{21}$

X-ray photoelectron spectroscopy (XPS) spectra of bare graphene and graphene modified with β-CDMe$_{21}$ were collected on a VersaProbe III Scanning XPS Microprobe (PHI 5000, 5 Physical Electronics, Chanhassen, MN). The results for the elemental surface composition of graphene modified with β-CDMe$_{21}$ are shown in Table 3.

TABLE 3

Elemental surface composition of graphene modified with β-CDMe$_{21}$, as determined by XPS.

| β-CDMe$_{21}$ Concentration (mM) in self-assembly solution | C % | Cu % | O % |
| --- | --- | --- | --- |
| 0 | 53.9 ± 0.5 | 15.5 ± 0.8 | 30.5 ± 0.8 |
| 0.0050 | 59.2 ± 1.7 | 14.8 ± 1.7 | 25.9 ± 1.1 |
| 0.010 | 60.3 ± 2.8 | 15.6 ± 2.0 | 24.1 ± 1.9 |
| 0.050 | 63.5 ± 1.0 | 16.0 ± 0.9 | 20.4 ± 1.4 |
| 0.10 | 63.2 ± 1.7 | 14.4 ± 1.9 | 22.5 ± 0.7 |
| 0.50 | 65.0 ± 1.1 | 14.5 ± 2.8 | 20.5 ± 2.8 |

The C %, O % and Cu % data were fitted simultaneously, as described above, to determine the equilibrium constant K. The equilibrium constant, K, and concentration of self-assembly solution needed for at least 90% monolayer formation with —CDMe$_{21}$ are shown in Table 4.

TABLE 4

Equilibrium constant and monolayer concentration for adsorption of β-CDMe$_{21}$ to graphene.

| Self-Assembly Molecule | Log K (Log M$^{-1}$) | Self-assembly solvent | Concentration of self-assembly solution needed for 90% surface coverage (mM) |
| --- | --- | --- | --- |
| β-CDMe$_{21}$ | 5.24 (5.15-5.31) | hexane | 0.052 |

Figure 11:
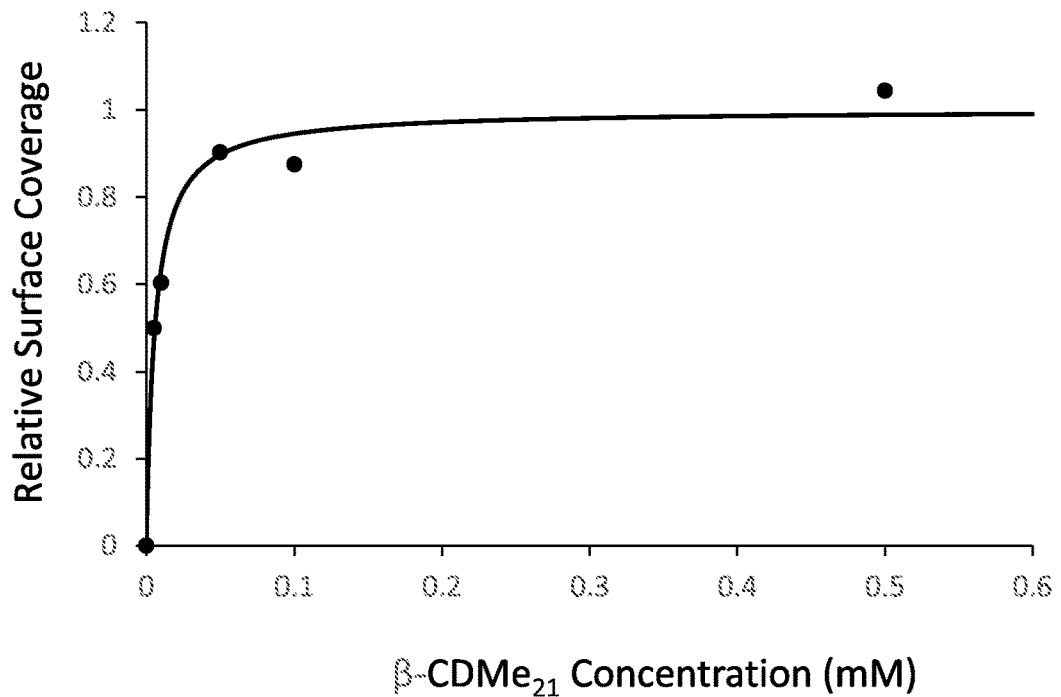
FIG. 11 is a representative plot of relative surface coverage as a function of concentration in accordance with various embodiments herein.
Figure 12:
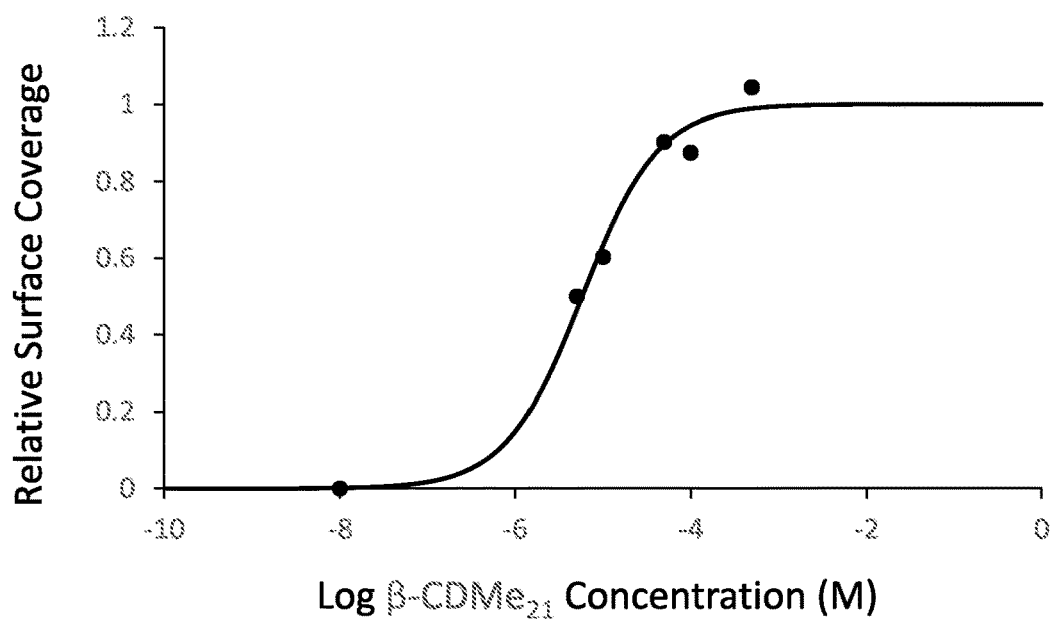
FIG. 12 is a representative plot of relative surface coverage as a function of the logarithm of concentration presented in FIG. 11, in accordance with various embodiments herein.

The Langmuir adsorption isotherm for the adsorption of graphene modified with β-CDMe$_{21}$ is shown in FIG. 11. The figure shows the relative monolayer coverage (dots) along with a fit (solid line) based on Langmuir adsorption theory for the adsorption of graphene modified with β-CDMe$_{21}$, as determined by XPS data. The relative surface coverage for the adsorption of β-CDMe$_{21}$ to graphene as a function of the logarithm of the β-CDMe$_{21}$ concentration in the self-assembly solution is shown in FIG. 12.

It should be noted that, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

As used herein, the recitation of numerical ranges by endpoints shall include all numbers subsumed within that range (e.g., 2 to 8 includes 2.1, 2.8, 5.3, 7, etc.).

The headings used herein are provided for consistency with suggestions under 37 CFR 1.77 or otherwise to provide organizational cues. These headings shall not be viewed to limit or characterize the invention(s) set out in any claims that may issue from this disclosure. As an example, although the headings refer to a "Field," such claims should not be limited by the language chosen under this heading to describe the so-called technical field. Further, a description of a technology in the "Background" is not an admission that technology is prior art to any invention(s) in this disclosure. Neither is the "Summary" to be considered as a characterization of the invention(s) set forth in issued claims.

The embodiments described herein are not intended to be exhaustive or to limit the invention to the precise forms disclosed in the following detailed description. Rather, the embodiments are chosen and described so that others skilled in the art can appreciate and understand the principles and practices. As such, aspects have been described with reference to various specific and preferred embodiments and techniques. However, it should be understood that many variations and modifications may be made while remaining within the spirit and scope herein.

The invention claimed is:

1. A medical device comprising:
   a graphene varactor comprising:
   a graphene layer;
   a self-assembled monolayer disposed on an outer surface of the graphene layer through non-covalent interactions between the self-assembled monolayer and a π-electron system of graphene; and
   wherein the self-assembled monolayer comprises one or more pillarenes, substituted pillarenes, calixarenes, substituted calixarenes, peralkylated cyclodextrins, or substituted peralkylated cyclodextrins.

2. The medical device of claim 1, wherein the self-assembled monolayer provides a Langmuir theta value of at least 0.9.

3. The medical device of claim 2, wherein the self-assembled monolayer provides a Langmuir theta value of at least 0.98.

4. The medical device of claim 2, wherein the self-assembled monolayer provides coverage over the graphene from 50% to 150% by surface area.

5. The medical device of claim 2, comprising a plurality of graphene varactors configured in an array on the medical device.

6. The medical device of claim 2, the self-assembled monolayer comprising substituted pillarenes comprising:

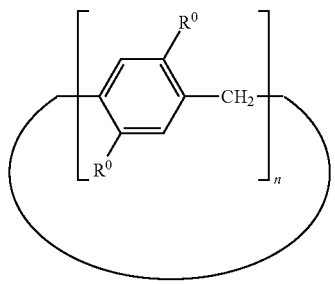

wherein each $R^0$ can independently comprise: $-R^1$, $-OR^1$, or $-SR^1$; and wherein each $R^1$ can independently comprise: $-H$; $-OH$; $=O$; any linear, branched, or cyclic $C_1$-$C_{20}$ alkyl, $C_1$-$C_{20}$ alkenyl, $C_1$-$C_{20}$ alkynyl, $C_1$-$C_{20}$ heteroalkyl, $C_1$-$C_{20}$ heteroalkenyl, $C_1$-$C_{20}$ heteroalkynyl, $C_1$-$C_{20}$ haloalkyl groups, $C_1$-$C_{20}$ haloalkenyl groups, $C_1$-$C_{20}$ haloalkynyl groups, $C_1$-$C_{20}$ halogenated heteroalkyl groups, $C_1$-$C_{20}$ halogenated heteroalkenyl groups, $C_1$-$C_{20}$ halogenated heteroalkynyl groups, or any combinations thereof; an aryl, heteroaryl, substituted aryl, substituted heteroaryl aryl, halogenated aryl, substituted halogenated aryl, a benzyl or a substituted benzyl, a biphenyl or substituted biphenyl, an aryloxy, arylthio, arylamine, or any substitutions thereof; $-R^2OH$, $-R^2C(O)OH$, $-R^2C(O)OR^2$, $-R^2OR^2$, $-R^2SR^2$, $-R^2CHO$, $-R^2X$ wherein X is a halogen atom, $-R^2C(O)NH_2$, $-R^2C(O)NR^2$, $-R^2NH_3+$, $-R^2NH_2$, $-R^2NO^2$, $-R^2NHR^2$, $-R^2NR^2R^2$, $-R^2N_3$, $-R^2OPO(OH)_2$, $-R^2OSO(OH)_2$, or any derivatives or combinations thereof;

wherein each $R^2$ can independently comprise any identical or different, linear, branched, or cyclic $C_1$-$C_{20}$ alkyl, $C_1$-$C_{20}$ alkenyl, $C_1$-$C_{20}$ alkynyl, $C_1$-$C_{20}$ heteroalkyl, $C_1$-$C_{20}$ heteroalkenyl, $C_1$-$C_{20}$ heteroalkynyl, $C_1$-$C_{20}$ haloalkyl groups, $C_1$-$C_{20}$ haloalkenyl groups, $C_1$-$C_{20}$ haloalkynyl groups, $C_1$-$C_{20}$ halogenated heteroalkyl groups, $C_1$-$C_{20}$ halogenated heteroalkenyl groups, $C_1$-$C_{20}$ halogenated heteroalkynyl groups, or any substitutions or combinations thereof; and wherein n is an integer from at least 5 to 15.

7. The medical device of claim 6, wherein at least some of the $R^0$ substituents differ from the other $R^0$ substituents.

8. The medical device of claim 2, the self-assembled monolayer comprising substituted pillarenes comprising:

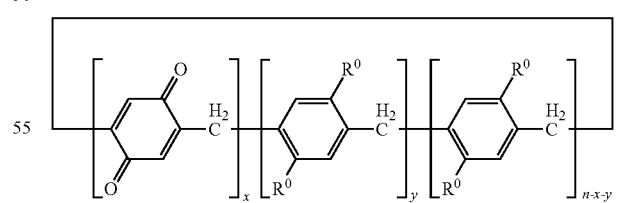

wherein each $R^0$ can independently comprise: $-R^1$, $-OR^1$, or $-SR^1$; and wherein each $R^1$ can independently comprise: $-H$; $-OH$; $=O$; any linear, branched, or cyclic $C_1$-$C_{20}$ alkyl, $C_1$-$C_{20}$ alkenyl, $C_1$-$C_{20}$ alkynyl, $C_1$-$C_{20}$ heteroalkyl, $C_1$-$C_{20}$ heteroalkenyl, $C_1$-$C_{20}$ heteroalkynyl, $C_1$-$C_{20}$ haloalkyl groups, $C_1$-$C_{20}$ haloalkenyl groups, $C_1$-$C_{20}$ haloalkynyl groups, $C_1$-$C_{20}$ halogenated heteroalkyl groups, $C_1$-$C_{20}$ halogenated heteroalkenyl groups, $C_1$-$C_{20}$ halogenated heteroalkynyl groups, or any combinations thereof; an aryl, heteroaryl, substituted aryl, substituted heteroaryl aryl, halogenated aryl, substituted halogenated aryl, a benzyl or a substituted benzyl, a biphenyl or substituted biphenyl, an aryloxy, arylthio, arylamine, or any substitutions thereof; —$R^2OH$, —$R^2C(O)OH$, —$R^2C(O)OR^2$, —$R^2OR^2$, —$R^2SR^2$, —$R^2CHO$, —$R^2X$ wherein X is a halogen atom, —$R^2C(O)NH_2$, —$R^2C(O)NR^2$, —$R^2NH_3+$, —$R^2NH_2$, —$R^2NO_2$, —$R^2NHR^2$, —$R^2NR^2R^2$, —$R^2N_3$, —$R^2OPO(OH)_2$, —$R^2OSO(OH)_2$, or any derivatives or combinations thereof;

wherein each $R^2$ can independently comprise any identical or different, linear, branched, or cyclic $C_1$-$C_{20}$ alkyl, $C_1$-$C_{20}$ alkenyl, $C_1$-$C_{20}$ alkynyl, $C_1$-$C_{20}$ heteroalkyl, $C_1$-$C_{20}$ heteroalkenyl, $C_1$-$C_{20}$ heteroalkynyl, $C_1$-$C_{20}$ haloalkyl groups, $C_1$-$C_{20}$ haloalkenyl groups, $C_1$-$C_{20}$ haloalkynyl groups, $C_1$-$C_{20}$ halogenated heteroalkyl groups, $C_1$-$C_{20}$ halogenated heteroalkenyl groups, $C_1$-$C_{20}$ halogenated heteroalkynyl groups, or any substitutions or combinations thereof; and wherein x is an integer from at least 0 to 15, y is an integer from at least 0 to 15, and n is an integer from at least 5 to 15.

9. The medical device of claim 2, the self-assembled monolayer comprising substituted calixarenes comprising any of:

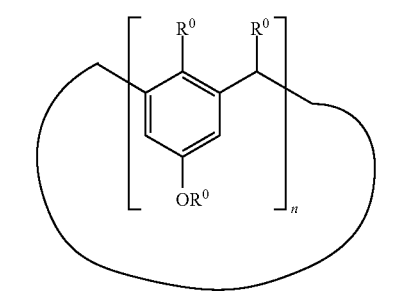

(a.)

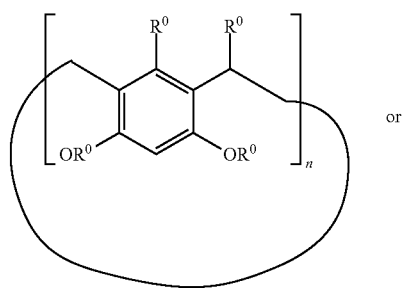

(b.)

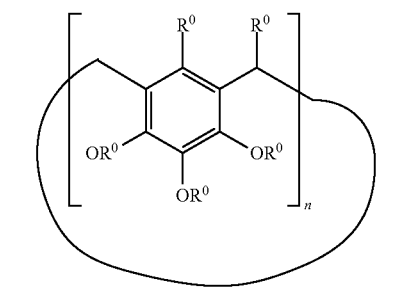

(c.)

wherein each $R^0$ can independently comprise: —$R^1$, —$OR^1$, or —$SR^1$; and wherein each $R^1$ can independently comprise: —H; —OH; any linear, branched, or cyclic $C_1$-$C_{20}$ alkyl, $C_1$-$C_{20}$ alkenyl, $C_1$-$C_{20}$ alkynyl, $C_1$-$C_{20}$ heteroalkyl, $C_1$-$C_{20}$ heteroalkenyl, $C_1$-$C_{20}$ heteroalkynyl, $C_1$-$C_{20}$ haloalkyl groups, $C_1$-$C_{20}$ haloalkenyl groups, $C_1$-$C_{20}$ haloalkynyl groups, $C_1$-$C_{20}$ halogenated heteroalkyl groups, $C_1$-$C_{20}$ halogenated heteroalkenyl groups, $C_1$-$C_{20}$ halogenated heteroalkynyl groups, or any combinations thereof; an aryl, heteroaryl, substituted aryl, substituted heteroaryl aryl, halogenated aryl, substituted halogenated aryl, a biphenyl or substituted biphenyl, an aryloxy, arylthio, arylamine, or any substitutions thereof; —$R^2OH$, —$R^2C(O)OH$, —$R^2C(O)OR^2$, —$R^2OR^2$, —$R^2SR^2$, —$R^2CHO$, —$R^2X$ wherein X is a halogen atom, —$R^2C(O)NH_2$, —$R^2C(O)NR^2$, —$R^2NH_3+$, —$R^2NH_2$, —$R^2NO_2$, —$R^2NHR^2$, —$R^2NR^2R^2$, —$R^2N_3$, —$R^2OPO(OH)_2$, —$R^2OSO(OH)_2$, or any derivatives or combinations thereof;

wherein each $R^2$ can independently comprise any identical or different, linear, branched, or cyclic $C_1$-$C_{20}$ alkyl, $C_1$-$C_{20}$ alkenyl, $C_1$-$C_{20}$ alkynyl, $C_1$-$C_{20}$ heteroalkyl, $C_1$-$C_{20}$ heteroalkenyl, $C_1$-$C_{20}$ heteroalkynyl, $C_1$-$C_{20}$ haloalkyl groups, $C_1$-$C_{20}$ haloalkenyl groups, $C_1$-$C_{20}$ haloalkynyl groups, $C_1$-$C_{20}$ halogenated heteroalkyl groups, $C_1$-$C_{20}$ halogenated heteroalkenyl groups, $C_1$-$C_{20}$ halogenated heteroalkynyl groups, or any substitutions or combinations thereof; and wherein n is an integer from at least 3 to 15.

10. The medical device of claim 2, the self-assembled monolayer comprising substituted peralkylated cyclodextrins comprising:

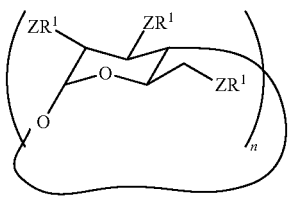

wherein each Z can independently comprise: —S or —O; and wherein each $R^1$ can independently comprise: —H; —OH; any linear, branched, or cyclic $C_1$-$C_{20}$ alkyl, $C_1$-$C_{20}$ alkenyl, $C_1$-$C_{20}$ alkynyl, $C_1$-$C_{20}$ heteroalkyl, $C_1$-$C_{20}$ heteroalkenyl, $C_1$-$C_{20}$ heteroalkynyl, $C_1$-$C_{20}$ haloalkyl groups, $C_1$-$C_{20}$ haloalkenyl groups, $C_1$-$C_{20}$ haloalkynyl groups, $C_1$-$C_{20}$ halogenated heteroalkyl groups, $C_1$-$C_{20}$ halogenated heteroalkenyl groups, $C_1$-$C_{20}$ halogenated heteroalkynyl groups, or any combinations thereof; an aryl, heteroaryl, substituted aryl, substituted heteroaryl aryl, halogenated aryl, substituted halogenated aryl, a benzyl or a substituted benzyl, a biphenyl or substituted biphenyl, an aryloxy, arylthio, arylamine, or any substitutions thereof; —$R^2OH$, —$R^2C(O)OH$, —$R^2C(O)OR^2$, —$R^2OR^2$, —$R^2SR^2$, —$R^2CHO$, —$R^2X$ wherein X is a halogen atom, —$R^2C(O)NH_2$, —$R^2C(O)NR^2$, —$R^2NH_3+$, —$R^2NH_2$, —$R^2NO_2$, —$R^2NHR^2$, —$R^2NR^2R^2$,—$R^2N_3$, —$R^2OPO(OH)_2$, —$R^2OSO(OH)_2$, or any derivatives or combinations thereof;

wherein each $R^2$ can independently comprise any identical or different, linear, branched, or cyclic $C_1$-$C_{20}$ alkyl, $C_1$-$C_{20}$ alkenyl, $C_1$-$C_{20}$ alkynyl, $C_1$-$C_{20}$ heteroalkyl, $C_1$-$C_{20}$ heteroalkenyl, $C_1$-$C_{20}$ heteroalkynyl, $C_1$-$C_{20}$ haloalkyl groups, $C_1$-$C_{20}$ haloalkenyl groups, $C_1$-$C_{20}$ haloalkynyl groups, $C_1$-$C_{20}$ halogenated heteroalkyl groups, $C_1$-$C_{20}$ halogenated heteroalkenyl groups, $C_1$-$C_{20}$ halogenated heteroalkynyl groups, or any substitutions or combinations thereof; and n is an integer from at least 5 to 10.

11. A method of modifying a surface of graphene, the method comprising:
   forming a self-assembled monolayer disposed on an outer surface of a graphene layer through non-covalent interactions between the self-assembled monolayer and a π-electron system of graphene;
   the self-assembled monolayer comprising one or more pillarenes, substituted pillarenes, calixarenes, substituted calixarenes, peralkylated cyclodextrins, or substituted peralkylated cyclodextrins; and
   quantifying an extent of surface coverage of the self-assembled monolayer using contact angle goniometry, Raman spectroscopy, or X-Ray photoelectron spectroscopy.

12. The method of claim 11, further comprising selecting derivatized graphene layers that exhibit a Langmuir theta value of at least 0.9.

13. The method of claim 11, further comprising selecting derivatized graphene layers that exhibit a Langmuir theta value of at least 0.98.

14. The method of claim 11, wherein the self-assembled monolayer comprising substituted pillarenes comprising:

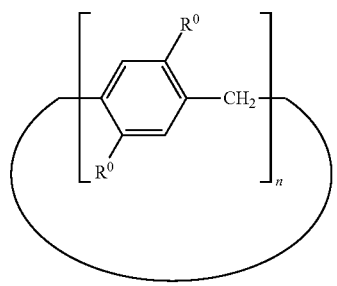

wherein each $R^0$ can independently comprise: —$R^1$, —$OR^1$, or —$SR^1$; and wherein each $R^1$ can independently comprise: —H; —OH; =O; any linear, branched, or cyclic $C_1$-$C_{20}$ alkyl, $C_1$-$C_{20}$ alkenyl, $C_1$-$C_{20}$ alkynyl, $C_1$-$C_{20}$ heteroalkyl, $C_1$-$C_{20}$ heteroalkenyl, $C_1$-$C_{20}$ heteroalkynyl, $C_1$-$C_{20}$ haloalkyl groups, $C_1$-$C_{20}$ haloalkenyl groups, $C_1$-$C_{20}$ haloalkynyl groups, $C_1$-$C_{20}$ halogenated heteroalkyl groups, $C_1$-$C_{20}$ halogenated heteroalkenyl groups, $C_1$-$C_{20}$ halogenated heteroalkynyl groups, or any combinations thereof; an aryl, heteroaryl, substituted aryl, substituted heteroaryl aryl, halogenated aryl, substituted halogenated aryl, a benzyl or substituted benzyl, a biphenyl or substituted biphenyl, an aryloxy, arylthio, arylamine, or any substitutions thereof; —$R^2OH$, —$R^2C(O)OH$, —$R^2C(O)OR^2$, —$R^2OR^2$, —$R^2SR^2$, —$R^2CHO$, —$R^2X$ wherein X is a halogen atom, —$R^2C(O)NH_2$, —$R^2C(O)NR^2$, —$R^2NH_3+$, —$R^2NH_2$, —$R^2NO_2$, —$R^2NHR^2$, —$R^2NR^2R^2$, —$R^2N_3$, —$R^2OPO(OH)_2$, —$R^2OSO(OH)_2$, or any derivatives or combinations thereof;

wherein each $R^2$ can independently comprise any identical or different, linear, branched, or cyclic $C_1$-$C_{20}$ alkyl, $C_1$-$C_{20}$ alkenyl, $C_1$-$C_{20}$ alkynyl, $C_1$-$C_{20}$ heteroalkyl, $C_1$-$C_{20}$ heteroalkenyl, $C_1$-$C_{20}$ heteroalkynyl, $C_1$-$C_{20}$ haloalkyl groups, $C_1$-$C_{20}$ haloalkenyl groups, $C_1$-$C_{20}$ haloalkynyl groups, $C_1$-$C_{20}$ halogenated heteroalkyl groups, $C_1$-$C_{20}$ halogenated heteroalkenyl groups, $C_1$-$C_{20}$ halogenated heteroalkynyl groups, or any substitutions or combinations thereof; and wherein n is an integer from at least 5 to 15.

15. The method of claim 11, wherein the self-assembled monolayer comprises substituted pillarenes comprising:

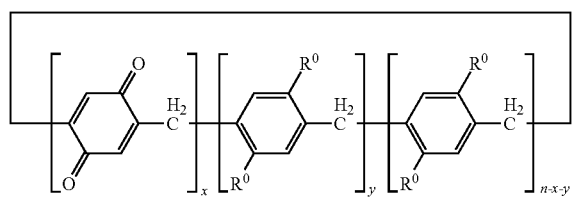

wherein each $R^0$ can independently comprise: —$R^1$, —$OR^1$, or —$SR^1$; and wherein each $R^1$ can independently comprise: —H; —OH; any linear, branched, or cyclic $C_1$-$C_{20}$ alkyl, $C_1$-$C_{20}$ alkenyl, $C_1$-$C_{20}$ alkynyl, $C_1$-$C_{20}$ heteroalkyl, $C_1$-$C_{20}$ heteroalkenyl, $C_1$-$C_{20}$ heteroalkynyl, $C_1$-$C_{20}$ haloalkyl groups, $C_1$-$C_{20}$ haloalkenyl groups, $C_1$-$C_{20}$ haloalkynyl groups, $C_1$-$C_{20}$ halogenated heteroalkyl groups, $C_1$-$C_{20}$ halogenated heteroalkenyl groups, $C_1$-$C_{20}$ halogenated heteroalkynyl groups, or any combinations thereof; an aryl, heteroaryl, substituted aryl, substituted heteroaryl aryl, halogenated aryl, substituted halogenated aryl, a benzyl or substituted benzyl, a biphenyl or substituted biphenyl, an aryloxy, arylthio, arylamine, or any substitutions thereof; —$R^2OH$, —$R^2C(O)OH$, —$R^2C(O)OR^2$, —$R^2OR^2$, —$R^2SR^2$, —$R^2CHO$, —$R^2X$ wherein X is a halogen atom, —$R^2C(O)NH_2$, —$R^2C(O)NR^2$, —$R^2NH_3+$, —$R^2NH_2$, —$R^2NO_2$, —$R^2NHR^2$, —$R^2NR^2R^2$, —$R^2N_3$, —$R^2OPO(OH)_2$, —$R^2OSO(OH)_2$, or any derivatives or combinations thereof;

wherein each $R^2$ can independently comprise any identical or different, linear, branched, or cyclic $C_1$-$C_{20}$ alkyl, $C_1$-$C_{20}$ alkenyl, $C_1$-$C_{20}$ alkynyl, $C_1$-$C_{20}$ heteroalkyl, $C_1$-$C_{20}$ heteroalkenyl, $C_1$-$C_{20}$ heteroalkynyl, $C_1$-$C_{20}$ haloalkyl groups, $C_1$-$C_{20}$ haloalkenyl groups, $C_1$-$C_{20}$ haloalkynyl groups, $C_1$-$C_{20}$ halogenated heteroalkyl groups, $C_1$-$C_{20}$ halogenated heteroalkenyl groups, $C_1$-$C_{20}$ halogenated heteroalkynyl groups, or any substitutions or combinations thereof; and wherein x is an integer from at least 0 to 15, y is an integer from at least 0 to 15, and n is an integer from at least 5 to 15.

16. The method of claim 11, wherein the self-assembled monolayer comprises substituted calixarenes comprising any of:

49

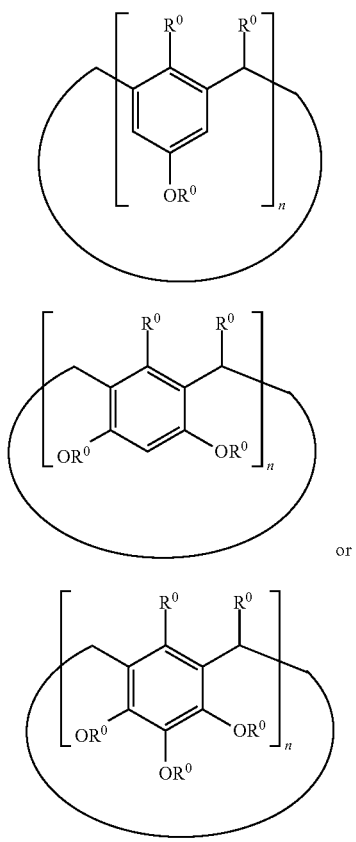

wherein each $R^0$ can independently comprise: —$R^1$, —$OR^1$, or —$SR^1$; and wherein each $R^1$ can independently comprise: —H; —OH; any linear, branched, or cyclic $C_1$-$C_{20}$ alkyl, $C_1$-$C_{20}$ alkenyl, $C_1$-$C_{20}$ alkynyl, $C_1$-$C_{20}$ heteroalkyl, $C_1$-$C_{20}$ heteroalkenyl, $C_1$-$C_{20}$ heteroalkynyl, $C_1$-$C_{20}$ haloalkyl groups, $C_1$-$C_{20}$ haloalkenyl groups, $C_1$-$C_{20}$ haloalkynyl groups, $C_1$-$C_{20}$ halogenated heteroalkyl groups, $C_1$-$C_{20}$ halogenated heteroalkenyl groups, $C_1$-$C_{20}$ halogenated heteroalkynyl groups, or any combinations thereof; an aryl, heteroaryl, substituted aryl, substituted heteroaryl aryl, halogenated aryl, substituted halogenated aryl, a benzyl or substituted benzyl, a biphenyl or substituted biphenyl, an aryloxy, arylthio, arylamine, or any substitutions thereof; —$R^2OH$, —$R^2C(O)OH$, —$R^2C(O)OR^2$, —$R^2OR^2$, —$R^2SR^2$, —$R^2CHO$, —$R^2X$ wherein X is a halogen atom, —$R^2C(O)NH_2$, —$R^2C(O)NR^2$, —$R^2NH_3+$, —$R^2NH_2$, —$R^2NO_2$, —$R^2NHR^2$, —$R^2NR^2R^2$, —$R^2N_3$, —$R^2OPO(OH)_2$, —$R^2OSO(OH)_2$, or any derivatives or combinations thereof;

wherein each $R^2$ can independently comprise any identical or different, linear, branched, or cyclic $C_1$-$C_{20}$ alkyl, $C_1$-$C_{20}$ alkenyl, $C_1$-$C_{20}$ alkynyl, $C_1$-$C_{20}$ heteroalkyl, $C_1$-$C_{20}$ heteroalkenyl, $C_1$-$C_{20}$ heteroalkynyl, $C_1$-$C_{20}$ haloalkyl groups, $C_1$-$C_{20}$ haloalkenyl groups, $C_1$-$C_{20}$ haloalkynyl groups, $C_1$-$C_{20}$ halogenated heteroalkyl groups, $C_1$-$C_{20}$ halogenated heteroalkenyl groups, $C_1$-$C_{20}$ halogenated heteroalkynyl groups, or any substitutions or combinations thereof; and wherein n is an integer from at least 3 to 15.

50

17. The method of claim 11, wherein the self-assembled monolayer comprises substituted peralkylated cyclodextrins comprising:

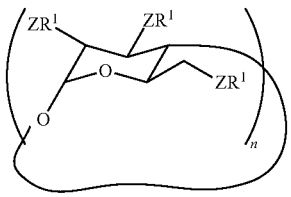

wherein each $R^0$ can independently comprise: —$R^1$, —$OR^1$, or —$SR^1$; and wherein each $R^1$ can independently comprise: —H; any linear, branched, or cyclic $C_1$-$C_{20}$ alkyl, $C_1$-$C_{20}$ alkenyl, $C_1$-$C_{20}$ alkynyl, $C_1$-$C_{20}$ heteroalkyl, $C_1$-$C_{20}$ heteroalkenyl, $C_1$-$C_{20}$ heteroalkynyl, $C_1$-$C_{20}$ haloalkyl groups, $C_1$-$C_{20}$ haloalkenyl groups, $C_1$-$C_{20}$ haloalkynyl groups, $C_1$-$C_{20}$ halogenated heteroalkyl groups, $C_1$-$C_{20}$ halogenated heteroalkenyl groups, $C_1$-$C_{20}$ halogenated heteroalkynyl groups, or any combinations thereof; an aryl, heteroaryl, substituted aryl, substituted heteroaryl aryl, halogenated aryl, substituted halogenated aryl, a benzyl or substituted benzyl, a biphenyl or substituted biphenyl, an aryloxy, arylthio, arylamine, or any substitutions thereof; —$R^2OH$, —$R^2C(O)OH$, —$R^2C(O)OR^2$, —$R^2OR^2$, —$R^2SR^2$, —$R^2CHO$, —$R^2X$ wherein X is a halogen atom, —$R^2C(O)NH_2$, —$R^2C(O)NR^2$, —$R^2NH_3+$, —$R^2NH_2$, —$R^2NO_2$, —$R^2NHR^2$, —$R^2NR^2R^2$,—$R^2N_3$, —$R^2OPO(OH)_2$, —$R^2OSO(OH)_2$, or any derivatives or combinations thereof;

wherein each $R^2$ can independently comprise any identical or different, linear, branched, or cyclic $C_1$-$C_{20}$ alkyl, $C_1$-$C_{20}$ alkenyl, $C_1$-$C_{20}$ alkynyl, $C_1$-$C_{20}$ heteroalkyl, $C_1$-$C_{20}$ heteroalkenyl, $C_1$-$C_{20}$ heteroalkynyl, $C_1$-$C_{20}$ haloalkyl groups, $C_1$-$C_{20}$ haloalkenyl groups, $C_1$-$C_{20}$ haloalkynyl groups, $C_1$-$C_{20}$ halogenated heteroalkyl groups, $C_1$-$C_{20}$ halogenated heteroalkenyl groups, $C_1$-$C_{20}$ halogenated heteroalkynyl groups, or any substitutions or combinations thereof; and wherein n is an integer from at least 5 to 10.

18. A method for detecting an analyte comprising:
collecting a gaseous sample;
contacting the gaseous sample with one or more graphene varactors, each of the one or more graphene varactors comprising:
   a graphene layer;
   a self-assembled monolayer disposed on an outer surface of the graphene layer through non-covalent interactions between the self-assembled monolayer and a π-electron system of graphene; and
wherein the self-assembled monolayer comprises at least one selected from the group consisting of pillarenes, substituted pillarenes, calixarenes, substituted calixarenes, peralkylated cyclodextrins, or substituted peralkylated cyclodextrins.

19. The method of claim 18, further comprising measuring a differential response in an electrical property of the one or more graphene varactors due to binding of one or more analytes present in the gaseous sample.

20. The method of claim 19, the electrical property selected from the group consisting of capacitance or resistance.

* * * * *